(12) United States Patent
Kusukame et al.

(10) Patent No.: US 10,624,581 B2
(45) Date of Patent: Apr. 21, 2020

(54) BIOLOGICAL INFORMATION ACQUISITION TERMINAL, INFORMATION MANAGEMENT METHOD, AND INFORMATION DISPLAY METHOD

(71) Applicant: Panasonic Intellectual Property Corporation of America, Torrance, CA (US)

(72) Inventors: Koichi Kusukame, Osaka (JP); Kazuki Funase, Osaka (JP); Masayuki Kozuka, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.

(21) Appl. No.: 16/132,897

(22) Filed: Sep. 17, 2018

(65) Prior Publication Data

US 2019/0015043 A1     Jan. 17, 2019

Related U.S. Application Data

(63) Continuation of application No. 14/360,748, filed as application No. PCT/JP2013/005308 on Sep. 6, 2013, now Pat. No. 10,098,586.

(Continued)

(30) Foreign Application Priority Data

Jun. 3, 2013    (JP) .................................. 2013-116827

(51) Int. Cl.
*A61B 5/00*        (2006.01)
*A61B 5/1455*    (2006.01)
(Continued)

(52) U.S. Cl.
CPC ................. *A61B 5/68* (2013.01); *A61B 5/00* (2013.01); *A61B 5/1455* (2013.01);
(Continued)

(58) Field of Classification Search
None
See application file for complete search history.

(56) References Cited

U.S. PATENT DOCUMENTS 4,036,211 A      7/1977   Veth et al.
5,331,549 A *   7/1994   Crawford, Jr. ......... G16H 40/63
                                                                              600/513
(Continued)

FOREIGN PATENT DOCUMENTS

CN         1451354       10/2003
CN      101193605       6/2008
(Continued)

OTHER PUBLICATIONS

Medgadget, "Visi Mobile System for Real Time Wireless In-Hospital Vital Signs Monitoring (video)", Aug. 21, 2012, URL: https://www.medgadget.com/2012/08/visi-mobile-systenn-for-real-time-wireless-in-hospital-vital-signs-monitoring-video.html (Year: 2012).*

(Continued)

*Primary Examiner* — David H Chu
(74) *Attorney, Agent, or Firm* — Wenderoth, Lind & Ponack, L.L.P.

(57) ABSTRACT

A bio-information acquiring terminal for acquiring bio-information includes a bath device. The bath device is provided with a bio-information measuring unit configured to measure bio-information of a user taking a bath, and a fingerprint authentication unit configured to specify the user.

(Continued)

According to the above configuration, it is possible to easily manage daily changes of the health condition of the user in his or her daily life.

4 Claims, 23 Drawing Sheets

Related U.S. Application Data

(60) Provisional application No. 61/721,523, filed on Nov. 2, 2012, provisional application No. 61/706,914, filed on Sep. 28, 2012.

(51) Int. Cl.
| | | |
|---|---|---|
| *A61B 5/1172* | (2016.01) | |
| *A61B 5/0402* | (2006.01) | |
| *A61B 5/08* | (2006.01) | |
| *A61B 5/01* | (2006.01) | |

(52) U.S. Cl.
CPC .......... *A61B 5/6891* (2013.01); *A61B 5/0088* (2013.01); *A61B 5/01* (2013.01); *A61B 5/0402* (2013.01); *A61B 5/0816* (2013.01); *A61B 5/1172* (2013.01); *A61B 5/14551* (2013.01); *A61B 5/4872* (2013.01); *A61B 2505/07* (2013.01)

(56) References Cited

U.S. PATENT DOCUMENTS

| 5,710,723 | A * | 1/1998 | Hoth .................. G01H 1/003 |
| | | | 702/181 |
| 5,974,615 | A | 11/1999 | Schwarz-Hartmann |
| 6,731,213 | B1 | 5/2004 | Smith |
| 7,386,333 | B1 | 6/2008 | Birecki |
| 2001/0029324 | A1 | 10/2001 | Walker et al. |
| 2003/0156119 | A1* | 8/2003 | Bonadio .................. G06F 3/0482 |
| | | | 345/589 |
| 2003/0190062 | A1 | 10/2003 | Noro et al. |
| 2004/0039601 | A1* | 2/2004 | Anderson .............. G06Q 50/22 |
| | | | 705/2 |
| 2004/0117212 | A1 | 6/2004 | Kong et al. |
| 2004/0148193 | A1* | 7/2004 | Blackburn ........... A61B 5/0002 |
| | | | 705/2 |
| 2006/0149597 | A1* | 7/2006 | Powell ................. G01D 21/00 |
| | | | 705/2 |
| 2006/0227123 | A1* | 10/2006 | Bychkov ............. H05K 5/0278 |
| | | | 345/204 |
| 2008/0060148 | A1 | 3/2008 | Pinyayev et al. |
| 2008/0146890 | A1* | 6/2008 | LeBoeuf ............. A61B 5/0059 |
| | | | 600/300 |
| 2008/0146892 | A1* | 6/2008 | LeBoeuf ................ G16H 50/30 |
| | | | 600/300 |
| 2008/0200774 | A1* | 8/2008 | Luo ...................... A61B 5/0002 |
| | | | 600/301 |
| 2008/0255432 | A1 | 10/2008 | Nielsen et al. |
| 2009/0169078 | A1 | 7/2009 | Ozawa |
| 2009/0241278 | A1 | 10/2009 | Lemchen |
| 2009/0307783 | A1* | 12/2009 | Maeda ................ G06F 11/3648 |
| | | | 726/30 |
| 2010/0094107 | A1* | 4/2010 | Lamego ................. A61B 5/061 |
| | | | 600/322 |
| 2010/0121220 | A1 | 5/2010 | Nishtala |
| 2010/0191147 | A1 | 7/2010 | Miyoshi et al. |
| 2011/0145894 | A1* | 6/2011 | Garcia Morchon ....................... |
| | | | G06F 19/3418 |
| | | | 726/4 |
| 2011/0296643 | A1 | 12/2011 | Shepherd |
| 2015/0164345 | A1 | 6/2015 | Nielsen et al. |

FOREIGN PATENT DOCUMENTS

| CN | 101312686 | 11/2008 |
| CN | 201431451 | 3/2010 |
| CN | 101791214 | 8/2010 |
| CN | 102024093 | 4/2011 |
| CN | 202015167 | 10/2011 |
| CN | 102597725 | 7/2012 |
| JP | 51-124080 | 10/1976 |
| JP | 7-100118 | 4/1995 |
| JP | 7-100218 | 4/1995 |
| JP | 8-29139 | 3/1996 |
| JP | 2000-504605 | 4/2000 |
| JP | 2002-83055 | 3/2002 |
| JP | 2003-225276 | 8/2003 |
| JP | 2003-260032 | 9/2003 |
| JP | 2004-102863 | 4/2004 |
| JP | 2004-130142 | 4/2004 |
| JP | 2005-291755 | 10/2005 |
| JP | 2005-331341 | 12/2005 |
| JP | 3150643 | 5/2009 |
| JP | 2009-183418 | 8/2009 |
| JP | 2010-530056 | 9/2010 |
| JP | 2011-234842 | 11/2011 |
| WO | 97/29714 | 8/1997 |
| WO | 2009/016844 | 2/2009 |

OTHER PUBLICATIONS

Office Action dated Jan. 21, 2016 in U.S. Appl. No. 14/360,748.
Final Rejection dated Sep. 20, 2016 in U.S. Appl. No. 14/360,748.
Office Action dated May 30, 2017 in U.S. Appl. No. 14/360,748.
International Search Report dated Oct. 29, 2013 in International (PCT) Application No. PCT/JP2013/005308.

* cited by examiner

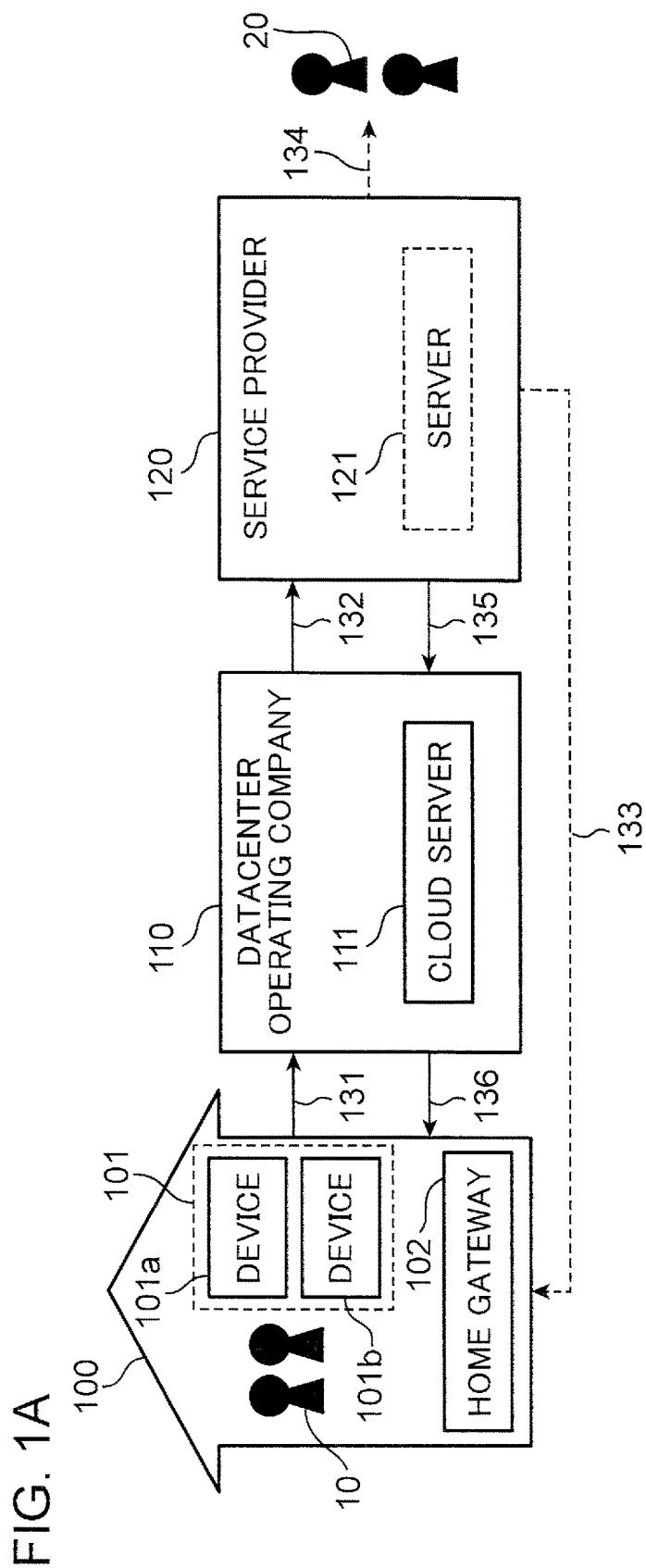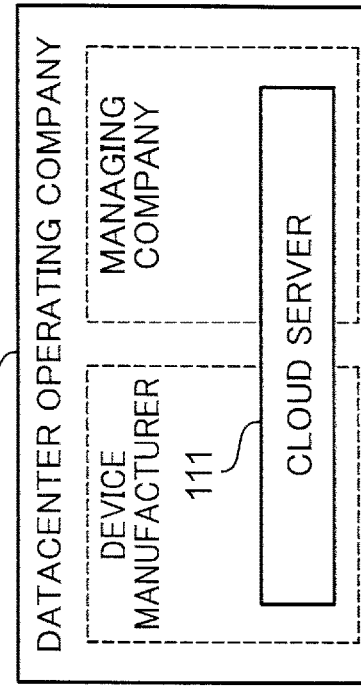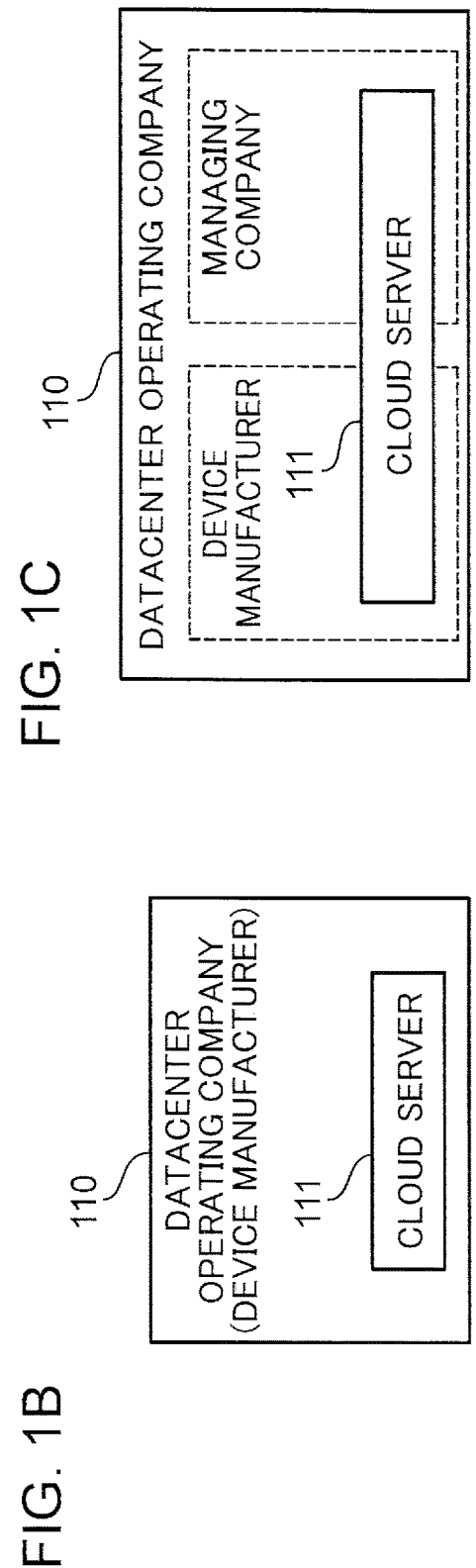

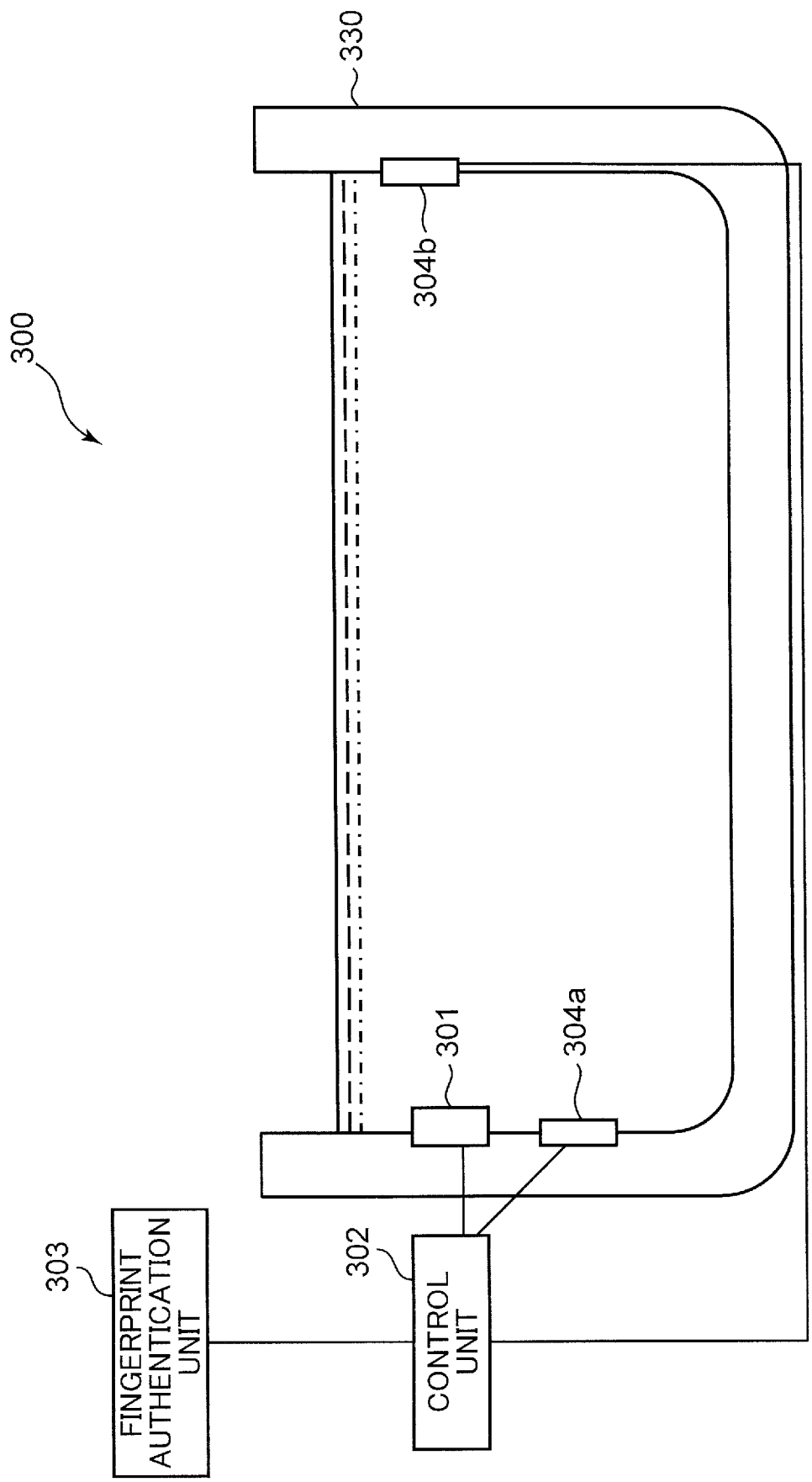

BIOLOGICAL INFORMATION ACQUISITION TERMINAL, INFORMATION MANAGEMENT METHOD, AND INFORMATION DISPLAY METHOD

TECHNICAL FIELD

The present invention relates to a bio-information acquiring terminal for acquiring bio-information, an information managing method using the bio-information acquiring terminal, and an information display method for displaying information to be generated based on collected bio-information on a display device.

BACKGROUND ART

In recent years, patients suffering from diabetes, myocardial infarction, cerebral infarction, or a kidney disease such as a chronic renal failure because of a life style such as an excessive salt intake, obesity, lack of exercise, aging, or stress are increasing, and preventive medical care at home is gathering attention.

For instance, even if part of the tissues of kidney is damaged, another part may immediately act for the damaged tissues. Therefore, a subjective symptom of a disease is less likely to appear. It is often the case that the disease may progress considerably when a subjective symptom such as high blood pressure symptoms or anorexia appears. In view of the above, it is desirable to periodically perform a screening test or the like.

Further, when the chronic renal failure progresses and an end-stage renal failure appears, the function of kidneys may be extremely lowered, and in a worse case, life support may be difficult or impossible. As a result, periodical dialysis or a kidney transplant may be necessary. In view of the above, prognostic management (medical follow-up) after detection of a renal failure is also important.

In view of the above, for instance, as disclosed in patent literature 1, in a medical institution or a like institution, there is carried out an inspection of calculating creatinine clearance based on the serum creatinine concentration from a sensor for measuring the serum creatinine concentration, and the urine creatinine concentration from a sensor for measuring the urine creatinine concentration in order to perform a screening test or medical follow-up on a renal failure.

However, the aforementioned inspection for health management is performed in a specific place such as a medical institution, and may be inappropriate for managing daily changes of the health condition.

CITATION LIST

Patent Literature

Patent literature 1: JP (Tokuhyo) 2010-530056A

SUMMARY OF INVENTION

In view of the above, an object of the invention is to provide a bio-information acquiring terminal, an information managing method, and an information display method that enable to easily manage daily changes of the health condition in a daily life.

A bio-information acquiring terminal according to an aspect of the invention is a bio-information acquiring terminal for acquiring bio-information. The bio-information acquiring terminal includes a bath device, and is provided with a bio-information measuring unit configured to measure bio-information of a user taking a bath, and a user specifying unit configured to specify the user.

According to the invention, it is possible to easily manage daily changes of the health condition of the user in his or her daily life, using the measured bio-information.

BRIEF DESCRIPTION OF DRAWINGS

FIG. 1A is a diagram illustrating an overview of services to be provided by an information managing system in an embodiment of the invention, FIG. 1B is a diagram illustrating an example, in which a device manufacturer corresponds to a datacenter operating company, and FIG. 1C is a diagram, in which both of or one of a device manufacturer and a managing company corresponds to a datacenter operating company;

FIG. 2 is a schematic diagram illustrating an example of a bio-information acquiring terminal according to a first embodiment of the invention;

DESCRIPTION OF EMBODIMENTS

Figure 3:
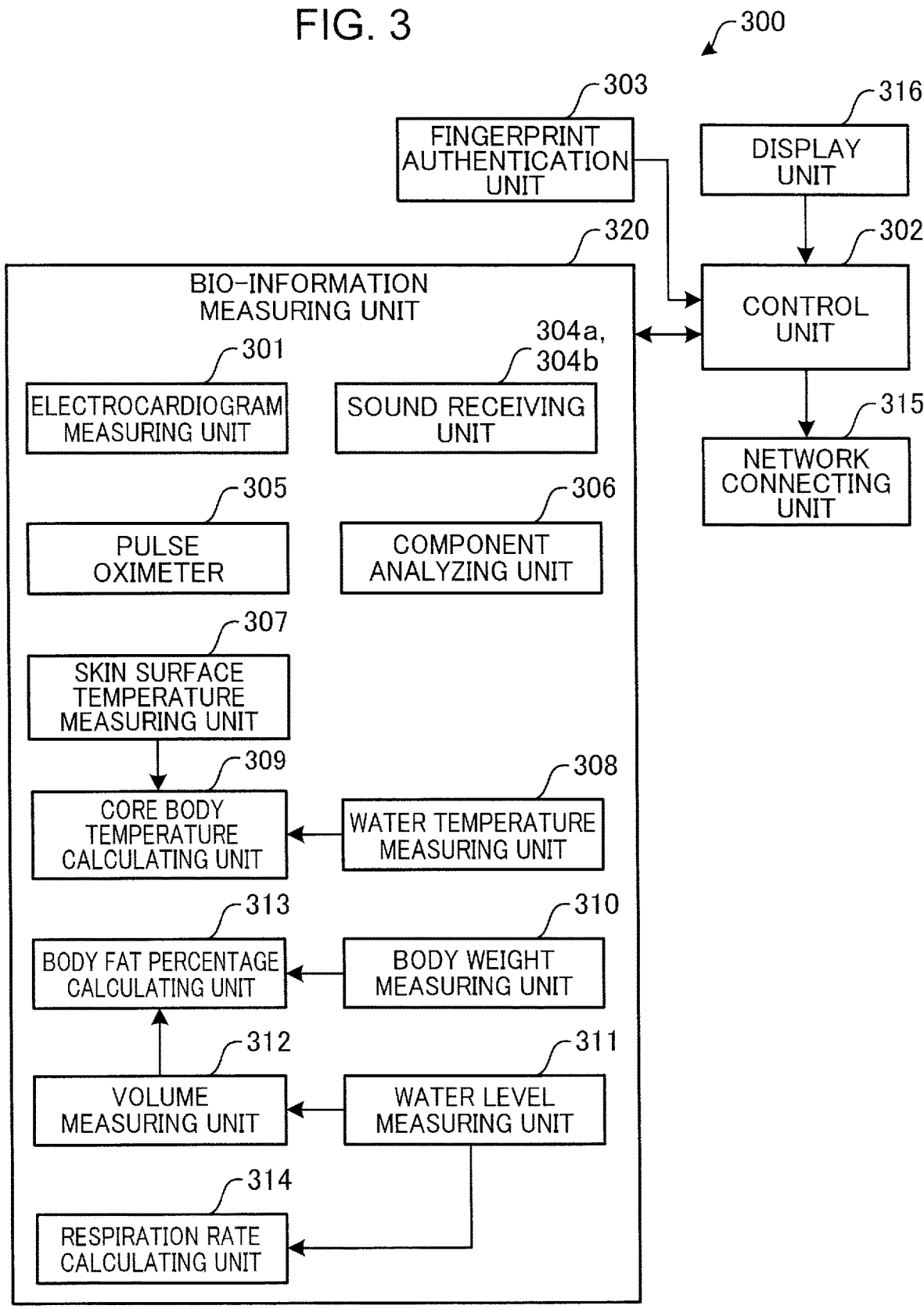
FIG. 3 is a block diagram illustrating a configuration of a bath device in the first embodiment.

In view of the foregoing, a bio-information acquiring terminal of the invention is a bio-information acquiring terminal for acquiring bio-information. The bio-information acquiring terminal includes a bath device. The bio-information acquiring terminal is provided with a bio-information measuring unit configured to measure bio-information of a user taking a bath, and a user specifying unit configured to specify the user.

According to the above configuration, it is possible to easily manage daily changes of the health condition of the user in his or her daily life, using the measured bio-information.

Further, the bio-information measuring unit may include an electrocardiogram measuring unit disposed in a bathtub and configured to measure an electrocardiogram of the user.

Further, the bio-information measuring unit may include a heart sound measuring unit disposed in a bathtub and configured to measure a heart sound of the user.

Further, the bio-information measuring unit may include a pulse oximeter disposed in a bathtub and configured to measure an oxygen saturation degree in blood of the user or a pulse rate of the user.

Further, the bio-information measuring unit may include a component analyzing unit disposed in a bathtub and configured to analyze a component of sweat of the user contained in water in the bathtub.

Further, the bio-information measuring unit may include a skin surface temperature measuring unit configured to measure a skin surface temperature of the user at a time before the user takes a bath and at a time after the user takes a bath.

Further, the bio-information measuring unit may include a water temperature measuring unit configured to measure a temperature of water in the bathtub at a time before the user takes a bath and at a time after the user takes a bath; and a core body temperature calculating unit configured to calculate a core body temperature of the user, based on a change in temperature of the water in the bathtub measured by the water temperature measuring unit at the time before the user takes a bath and at the time after the user takes a bath, a heat capacity of the user, and the skin surface temperature measured by the skin surface temperature measuring unit at the time before the user takes a bath.

Further, the bio-information measuring unit may include a body weight measuring unit configured to measure a weight of the user.

Further, the bio-information measuring unit may include a body volume measuring unit configured to measure a body volume of the user; and a body fat percentage calculating unit configured to calculate a body density of the user based on the body volume of the user measured by the body volume measuring unit and the weight of the user measured by the body weight measuring unit, and to calculate a body fat percentage from the body density of the user.

Further, the bio-information measuring unit may include a water level measuring unit configured to measure a change in water level in a bathtub for a predetermined time in a state that the user is in the bathtub; and a respiration rate calculating unit configured to calculate a respiration rate of the user for the predetermined time, based on the change in water level for the predetermined time measured by the water level measuring unit.

Further, as another aspect, there is provided an information managing method in an information managing system for managing bio-information collected from a bio-information acquiring terminal via a network. The bio-information acquiring terminal may include a bath device. The method may include collecting the bio-information of the user taking a bath, and user specifying information for specifying the user from the bio-information acquiring terminal via the network; and storing the bio-information and the user specifying information collected from the bio-information acquiring terminal in association with each other.

Further, as another aspect, there is provided an information displaying method for displaying, on a display device, information to be generated based on bio-information collected in a service providing system configured such that a service provider collects the bio-information from a plurality of bio-information acquiring terminals via a network and provides a service based on the collected bio-information. The method may include displaying on the display device of one or more of the bio-information acquiring terminals owned by the user; (i) displaying each of the bio-information collected by the bio-information acquiring terminals in association with each of the bio-information acquiring terminals, and (ii) displaying by changing a display method depending on whether the bio-information is to be disclosed to the service provider.

Further, as another aspect, the information display method may be further provided with displaying by changing the display method depending on whether each of the bio-information is to be stored in the bio-information acquiring terminal.

In the following, embodiments of the invention are described referring to the drawings. The following embodiments are merely an example of the invention, and do not limit the technical scope of the invention.

(Overview of Services to be Provided)

First of all, an overview of services to be provided by an information managing system in an embodiment is described.

FIG. 1A is a diagram illustrating an overview of services to be provided by the information managing system in the embodiment. The information managing system is provided with a group 100, a datacenter operating company 110, and a service provider 120.

The group 100 is, for instance, a company, a party, or a home. The scale of the group 100 does not matter. The group 100 is provided with a number of devices 101 including a device 101*a* and a device 101*b*, and a home gateway 102. The devices 101 include devices (e.g. a smartphone, a personal computer (PC) or a TV receiver) connectable to the Internet, and devices (e.g. an illumination device, a washing machine, or a refrigerator) incapable of being connected to the Internet by themselves. The devices 101 may include devices which are not connectable to the Internet by themselves, but are connectable to the Internet via the home gateway 102. Users 10 use the devices 101 within the group 100.

The datacenter operating company 110 is provided with a cloud server 111. The cloud server 111 is a virtual server connectable to a variety of devices via the Internet. The cloud server 111 mainly manages big data, which is difficult to be handled by an ordinary database management tool or a like tool. The datacenter operating company 110 manages data, manages the cloud server 111, and operates a datacenter which performs these services. The details of the services to be provided by the datacenter operating company 110 will be described later.

The datacenter operating company 110 is not limited to a company which manages data or manages the cloud server 111. For instance, as illustrated in FIG. 1B, in the case where a device manufacturer which develops or manufactures one of the devices 101 manages data or manages the cloud server 111, the device manufacturer corresponds to the datacenter operating company 110. Further, the number of datacenter operating companies is not limited to one. For instance, as illustrated in FIG. 1C, in the case where a device manufacturer and a managing company jointly or sharingly manage data or manage the cloud server 111, both or one of the device manufacturer and the managing company corresponds to the datacenter operating company 110.

The service provider 120 is provided with a server 121. The scale of the server 121 does not matter. For instance, the server 121 includes a memory in a PC for personal use. Further, the service provider 120 may not be provided with the server 121.

In the aforementioned information managing system, the home gateway 102 is not an essential element. For instance, in the case where the cloud server 111 manages all the data, the home gateway 102 is not necessary. Further, in the case where all the devices in a home are connected to the Internet, a device incapable of being connected to the Internet by itself may not exist.

Next, a flow of information in the information managing system is described.

The device 101a or the device 101b in the group 100 individually transmits log information thereof to the cloud server 111 in the datacenter operating company 110. The cloud server 111 accumulates the log information of the device 101a or the device 101b (see the arrow 131 in FIG. 1A). The log information is information indicating e.g. operation conditions or operation dates and times of the devices 101. For instance, the log information includes a viewing history of TV, video recording reservation information in a recorder, an operation date and time of a washing machine, a quantity of laundry, an opening/closing date and time of a refrigerator, or the number of times of opening/closing a refrigerator. The log information is not limited to these information, and may include a variety of information acquirable from a variety of devices. The log information may be directly provided from the devices 101 themselves to the cloud server 111 via the Internet. Further, the log information may be temporarily accumulated in the home gateway 102 from the devices 101, and may be provided from the home gateway 102 to the cloud server 111.

Next, the cloud server 111 in the datacenter operating company 110 provides the accumulated log information to the service provider 120 by a unit. The unit may be the amount of information, by which the datacenter operating company 110 can organize the accumulated information and provide to the service provider 120, or may be the amount of information required from the service provider 120. In the embodiment, information is provided by a unit. Alternatively, the amount of information to be provided may vary depending on a condition, in place of a unit. The log information is stored in the server 121 owned by the service provider 120, as necessary (see the arrow 132 in FIG. 1A).

The service provider 120 organizes the log information into information appropriate for the service to be provided to the user, and provides the organized information to the user. The user to whom information is provided may be a user 10 who uses the devices 101, or may be an external user 20. The information providing method to the users 10 and 20 may be such that information is directly provided to the users 10 and 20 from the service provider 120 (see the arrows 133 and 134 in FIG. 1A). Further, the information providing method to the user 10 may be such that information is provided to the user 10 via the cloud server 111 in the datacenter operating company 110 (see the arrows 135 and 136 in FIG. 1A). Further, the cloud server 111 in the datacenter operating company 110 may organize the log information into information appropriate for the service to be provided to the user, and may provide the organized information to the service provider 120.

The user 10 may be identical to or different from the user 20.

The information managing system in the embodiment of the invention is provided with a bio-information acquiring terminal provided with a bio-information acquiring unit.

In the following, embodiments of the invention will be described referring to the drawings.

In the first to third embodiments, a bio-information acquiring terminal is described, and in the fourth embodiment, an information managing system using the bio-information acquiring terminal described in the first to third embodiments is described.

It should be noted that the same constituent elements throughout the drawings are indicated with the same numerals, and repeated description thereof may be omitted.

First Embodiment

FIG. 2 is a schematic diagram illustrating an example of a bio-information acquiring terminal according to the first embodiment.

In the first embodiment, a bath device 300 is an example of a bio-information acquiring terminal provided with a bio-information acquiring unit. In this embodiment, an electrocardiogram measuring unit 301 measures an electrocardiogram of a user taking a bath. Further, sound receiving units 304a and 304b measure the heart sound of the user taking a bath.

The user takes a bath on the daily basis with use of the bath device 300. In taking a bath, the electrocardiogram measuring unit 301 measures an electrocardiogram of the user. Information relating to the acquired electrocardiogram is stored in a control unit 302 provided with a memory unit. Further, the sound receiving units 304a and 304b measure the heart sound of the user. Information relating to the acquired heart sound is stored in the control unit 302 provided with a memory unit.

In the following, the details of the bio-information acquiring terminal in the embodiment is described.

FIG. 3 is a block diagram illustrating a configuration of the bath device in the first embodiment.

The bath device 300 is provided with a bio-information measuring unit 320, the control unit 302, a fingerprint authentication unit 303, a network connecting unit 315, and a display unit 316. The bio-information measuring unit 320 is configured to measure bio-information of the user taking a bath. The bio-information measuring unit 320 is provided with the electrocardiogram measuring unit 301, the sound receiving units 304a, 304b, a pulse oximeter 305, a component analyzing unit 306, a skin surface temperature measuring unit 307, a water temperature measuring unit 308, a core body temperature measuring unit 309, a body weight measuring unit 310, a water level measuring unit 311, a body volume measuring unit 312, a body fat rate calculating unit 313, and a respiration rate calculating unit 314.

FIG. 2 and FIG. 3 are an example of the embodiment. All the constituent elements illustrated in FIG. 2 and FIG. 3 are not essential elements, and each of the constituent elements exhibits the following effect, even in the case where the bath device is not provided with some of the constituent elements.

In the embodiment, the electrocardiogram measuring unit 301 is constituted of electrodes, and measures an electrocardiogram of the user taking a bath. For instance, the electrocardiogram measuring unit 301 is disposed inside a bathtub 330, more specifically, is disposed at such a position that the back of the user comes into contact with when the user takes a bath. Further, the electrocardiogram measuring unit 301 may measure the pulse wave of the user. It is possible to perform a screening test for arteriosclerosis of the user from the waveform of the pulse wave measured by the electrocardiogram measuring unit 301.

In the case of measuring an electrocardiogram, the control unit 302 may perform frequency separation with respect to an electrical signal of an electrocardiogram acquired by the electrocardiogram measuring unit 301. By performing the above operation, even in the case where plural users take a bath in the bathtub 330 at the same time, it is possible to separate the electrocardiographic waveforms of the users from each other, utilizing a heart rate difference between the users, whereby it is possible to manage the health condition of each of the users.

Further, in the foregoing example, an electrocardiogram of the user taking a bath is measured. In the embodiment, the bio-information measuring unit 320 may be provided with a measuring unit configured to measure another bio-information, or may be provided with plural measuring units.

As illustrated in FIG. 2, the sound receiving unit 304a, 304b is constituted of a microphone incorporated with a movable coil and a magnet, a capacitor microphone, or a piezoelectric element. The sound receiving units 304a and 304b are configured to measure the heart sound of the user taking a bath. For instance, the sound receiving units 304a and 304b are disposed inside the bathtub 330. With use of the sound receiving units 304a and 304b, it is possible to detect a change in heart rate of the user at a low cost. The sound receiving units 304a and 304b correspond to an example of a heart sound measuring unit.

As described above, the bath device 300 is provided with the sound receiving units 304a and 304b disposed at different positions from each other. According to this configuration, even in the case where plural users take a bath in the bathtub 330 at the same time, it is possible to separate the heart sounds of the users from each other, and to individually detect the heart sounds, because a time required for a sound wave to reach from the heart of each of the users to the sound receiving unit 304a, 304b differs due to a difference in the distance between the heart of each of the users and the sound receiving unit 304a, 304b. This makes it possible to manage the health condition of each of the users.

It is desirable to install the sound receiving units 304a and 304b respectively on two surfaces of the inner side surfaces of the bathtub 330 away from each other by a largest distance. This makes it possible to detect a heart sound of each of the users with high precision.

Further, the bath device 300 may be provided with three or more sound receiving units. Installing the sound receiving units at three or more positions makes it possible to detect a heart sound of each of the users with high precision, no matter where the users are located.

Further, providing three or more sound receiving units makes it possible to grasp the distance between the heart of the user to the sound receiving units. This makes it possible to measure the magnitude of the heart sound (a sound pressure) of the user. This is desirable because it is possible to predict the health condition of the user from many aspects.

Further, it is desirable to install the sound receiving units 304a and 304b at a position lower than the water level. In the case where the water level is lower than the sound receiving units 304a and 304b, the bath device 300 may be provided with an alarm device configured to alert the user that the water level is lowered to such a level that it is impossible to measure the heart sound. Further, in the case where the water level is lower than the sound receiving units 304a and 304b, the bath device 300 may be provided with a notification unit configured to notify a message that "the water level is lowered to such a level that it is impossible to measure the heart sound" with use of a display unit or a sound output unit. The above configuration makes it possible to measure the heart sound with high sensitivity, and makes it easy to measure the heart sound, even if the user watches TV (installed in a bathroom) with a large sound volume while taking a bath.

Further, the sound receiving units 304a and 304b may measure the pulmonary sound of the user. The above configuration also makes it possible to measure the pulmonary sound of the user by the sound receiving units 304a and 304b as well as the above configuration. This is advantageous in early detection of an asthma attack.

Further, in the embodiment, the bio-information measuring unit 320 is provided with the two sound receiving units 304a and 304b. The invention is not specifically limited to the above. The bio-information measuring unit 320 may be provided with only one sound receiving unit 304a.

It is desirable to use an electrocardiogram in order to perform a screening test for arteriosclerosis. This is advantageous in performing a screening test for arteriosclerosis with high precision.

Further, the bath device 300 may be provided with the pulse oximeter 305, in addition to the electrocardiogram measuring unit 301, and the sound receiving units 304a and 304b. The pulse oximeter 305 is configured to measure the oxygen saturation degree in the user's blood or the pulse rate of the user.

The electrocardiogram measuring unit 301, and the sound receiving units 304a and 304b are advantageous in measuring the user's heart rate at a low cost, as compared with the pulse oximeter 305. However, the pulse oximeter 305 is capable of measuring an oxygen saturation level, in addition to a heart rate. Accordingly, the aforementioned combination is a desirable configuration for the purpose of monitoring the fatigue of the user.

Further, the bio-information measuring unit 320 may be provided with a plurality of pulse oximeters 305 in the bathtub 330. In the case where a plurality of users take a bath, it is possible to measure the heart rate of each of the users by utilizing the pulse oximeters 305 different from each other. Further, the pulse oximeter 305 may be provided with an authentication unit capable of fingerprint authentication or finger vein authentication. This is advantageous in easily monitoring the heart rate of each of the users.

Further, the bio-information measuring unit 320 may be provided with a conductivity measuring unit configured to measure the conductivity of water in the bathtub when the user is taking a bath. The control unit 302 is configured to calculate the amount of sweat of the user taking a bath, based on the conductivity of water in the bathtub measured by the conductivity measuring unit. The amount of sweat is useful, as one of the bio-information, in grasping the health condition of the user such as thermoregulation of the user. Accordingly, the above configuration is advantageous in grasping the condition of a disease in a wide range.

Further, the bio-information measuring unit 320 may be provided with a component analyzing unit 306 configured to analyze the components of water in the bathtub, in which the user is taking a bath. The component analyzing unit 306 is configured to analyze the components of sweat of the user contained in water in the bathtub. This makes it possible to analyze the components of sweat contained in water in the bathtub. This is advantageous in grasping the condition of a disease in a wide range, because the number of kinds of bio-information to be obtained increases as well as the above configuration.

The component analyzing unit 306 may be an absorption spectrum measuring unit configured to measure the absorption spectrum of near infrared light or far infrared light from a test substance, an optical rotation measuring unit configured to measure the optical rotation of a test substance, an optical rotatory dispersion measuring unit configured to measure the optical rotatory dispersion spectrum of a test substance, or a Raman spectroscopic measuring unit configured to measure the scattering spectrum of Raman scattering light from a test substance. In any of these configurations, it is possible to acquire bio-information at a low cost without expendable supplies.

The bath device 300 in the embodiment is desirable as a bio-information acquiring terminal, because it is possible to control the body temperature of the user with high precision. The bath device 300 makes it possible to measure daily changes of the health condition by the body temperature. Accordingly, it is possible to measure the health condition with high precision.

Further, the bio-information measuring unit 320 may be configured to measure bio-information a number of times while the user is taking a bath. This makes it possible to measure a change in bio-information due to a change in body temperature of the user.

For instance, it is desirable for the electrocardiogram measuring unit 301 to measure both of an electrocardiographic waveform immediately after the user takes a bath, and an electrocardiographic waveform at a point of time upon lapse of a certain time after taking a bath is designated. It is possible to estimate a thermoregulatory state of the user by comparing between these electrocardiographic waveforms.

Further, it is possible to estimate a temperature at which the user starts to perspire based on a time required for the user to start perspiring after the user takes a bath by measuring the amount of sweat a number of times. This also makes it possible to estimate a thermoregulatory state of the user as well as the above configuration.

Further, the bio-information measuring unit 320 may be provided with a skin surface temperature measuring unit 307 configured to measure the skin surface temperature of the user. The skin surface temperature measuring unit 307 is configured to measure the skin surface temperature of the user before and after the user takes a bath. This makes it possible to reduce an influence (noise) resulting from a body temperature at a measurement time in recording daily changes of the health condition. This is advantageous in grasping the health condition of the user with high precision.

Figure 4:
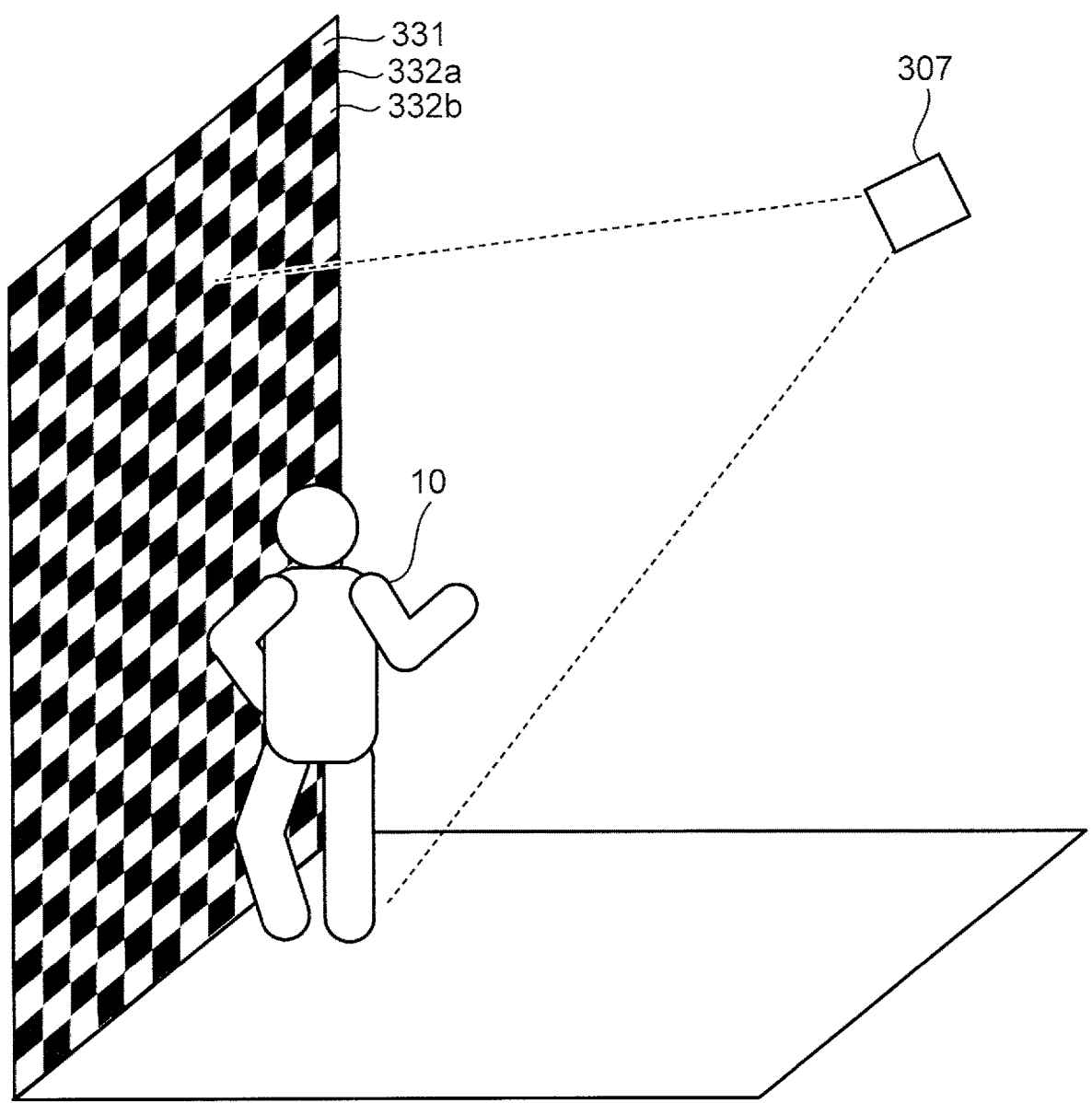
FIG. 4 is a diagram illustrating a configuration of a skin surface temperature measuring unit in the first embodiment.

FIG. 4 is a diagram illustrating a configuration of the skin surface temperature measuring unit in the first embodiment. The skin surface temperature measuring unit 307 is constituted of a thermography device, for instance.

Further, it is desirable to form a wall surface 331 within an imaging area of the skin surface temperature measuring unit 307 which is configured to measure the skin surface temperature of the user, of a plurality of members having emissivities different from each other. As illustrated in FIG. 4, the wall surface 331 is constituted of first members 332a, and second members 332b whose emissivity is different from the emissivity of the first members 332a. The first members 332a and the second members 332b are disposed in a lattice pattern. According to this configuration, in the case where the user 10 is present between the wall surface 331 and the skin surface temperature measuring unit 307, it is possible to accurately measure the skin surface temperature of the user 10 even if the skin surface temperature of the user 10 becomes substantially equal to the surface temperature of the wall surface 331, because the boundary between the wall surface 331 and the user 10 is clear. Specifically, the skin surface temperature measuring unit 307 is capable of recognizing the pattern of the wall surface 331 constituted of the first member 332a and the second member 332b having emissivities different from each other. Accordingly, it is possible to discriminate an image representing the user 10, and an image representing the wall surface 331 from each other.

Further, it is desirable to form the back portion (an outer portion of the bathroom) of the wall surface 331 of a metal (copper or aluminum) having a high thermal conductivity or of a graphite sheet. This is advantageous in setting the temperatures of the members constituting the wall surface 331 made of different materials to be substantially equal to each other, whereby it is possible to clarify the pattern of the wall surface 331. This makes it possible to clarify the boundary between the wall surface 331 and the user 10. This is advantageous in measuring a skin surface temperature of the user 10 with high precision.

Further, it is desirable to form the first members 332a and the second members 332b constituting the wall surface 331 such that the surface of the first members 332a and the surface of the second members 332b have water repellencies different from each other. This makes it possible to dry the inside of the bathroom. This is advantageous in preventing lowering of measurement precision of a measuring device resulting from growth of mold or the like. Further, water droplets may remain on a member having low water repellency, and heat of vaporization is continued to be deprived of from the member. As a result, the surface temperature of the member having low water repellency is lower than the surface temperature of a member having high water repellency. In view of the above, constituting the wall surface 331 of the first members 332a and the second members 332b having water repellencies different from each other makes it possible to discriminate an image representing the user 10, and an image representing the wall surface 331 from each other.

Further, at least a part of the wall surface 331 disposed within the imaging area of the skin surface temperature measuring unit 307 may be made of a metal having a small emissivity (e.g. 0.5 or less). This makes it possible to detect whether water droplets remain on the wall surface 331 due to a difference in emissivity between the wall surface 331 and water droplets. This is advantageous in accurately grasping a dry state of the bathroom, and in suppressing growth of mold.

Further, the skin surface temperature measuring unit 307 may be desirably provided with a heating unit configured to heat a member such as a lens or a window member for use in receiving infrared rays radiated from a human body. Heating the lens or the window member makes it possible to prevent dew condensation, whereby it is possible to measure the skin surface temperature of the user with high precision.

Further, a result of a unique investigation by the inventors reveals that the skin surface temperature of an internal body part rich in fat is low, and the skin surface temperature of an internal body part rich in muscle is high. In view of the above, the control unit 302 is capable of grasping the amount of muscle, the amount of fat, or a distribution of fat, based on the skin surface temperature distribution of the user measured by the skin surface temperature measuring unit 307. Further, the control unit 302 is capable of calculating a metabolic syndrome index or a locomotive syndrome index, based on the amount of muscle or the amount of fat, whereby it is possible to use the calculation result for health management.

Further, the skin surface temperature measuring unit 307 may be configured to measure the skin surface temperature a number of times, for instance, at a time before the user takes a bath, at a time immediately after the user takes a bath, and at a time after lapse of several minutes after the user takes a bath. It is possible to estimate a blood circulation state or the amount of cellulite, based on a time constant of a temperature change of each of the body parts of the user, whereby it is possible to use the estimation amount for health management.

Likewise, performing health management based on a change in bio-information due to a change in body temperature as described above is also desirable for high precision measurement.

The skin surface temperature measuring unit 307 may be desirably a non-contact temperature measuring unit composed of a thermopile or a bolometer disposed on the outside of the bathroom and configured to measure the skin surface temperature of the user before the user takes a bath. This makes it possible to measure the skin surface temperature of the user at a low cost.

Further, the skin surface temperature measuring unit 307 may be desirably configured to measure the skin surface temperature of the user taking a bath. This is advantageous in accurately recording daily changes of the bio-information.

Further, the bio-information measuring unit 320 may be further provided with a water temperature measuring unit 308 configured to measure the temperature of hot water in the bathtub before the user takes a bath, measure the temperature of hot water in the bathtub after the user takes a bath, and measure a change in hot water temperature in the bathtub before and after the user takes a bath. The water temperature measuring unit 308 may be configured to store a measured temperature change. Further, the bio-information measuring unit 320 may be provided with a core body temperature calculating unit 309 configured to calculate a core body temperature of the user, based on a change in hot water temperature measured by the water temperature measuring unit 308, a pre-stored heat capacity of the user, and a skin surface temperature measured by the skin surface temperature measuring unit 307 before the user takes a bath.

More specifically, the core body temperature calculating unit 309 is configured to calculate a heat capacity (hot water temperature×heat capacity of hot water) of the inside of the bathtub before the user takes a bath, and a heat capacity (hot water temperature×heat capacity of hot water+hot water temperature×heat capacity of user) of the inside of the bathtub when the user is taking a bath. Calculating a difference between the two values yields a quantity of heat (heat capacity of user×average internal body temperature of user) of the user before the user takes a bath. A core body temperature is estimated by performing backward calculation with use of an average temperature and a skin surface temperature by means of measuring the skin surface temperature of the user. In order to perform accurate calculation, it is desirable to use a database of each of the users regarding a relationship between an average internal body temperature, a skin surface temperature, and a core body temperature. For instance, it is possible to implement a formula: an average internal body temperature×2−skin surface temperature=core body temperature. Performing the calculation as described above makes it possible to calculate a core body temperature of the user. Since there is no or less likelihood that the heat capacity of the user greatly changes on the daily basis, comparing a change in hot water temperature of the inside of the bathtub on the daily basis makes it possible to calculate an internal body temperature (a core body temperature) of the user.

Measuring an internal body temperature allows for early detection of a cold or influenza.

As will be described later in the fourth embodiment, for instance, it is possible to manage the condition of a disease of each of the users such as a cold by connecting the bath device 300 to a network and by causing a processing server to collect information relating to an average value of internal body temperatures of each of the users at each home. Further, it is desirable for the processing server to collect a change in internal body temperature of inhabitants (users) area by area in order to grasp the incidence rate of influenza area by area. For this purpose, the processing server may collect information as to whether the inhabitants (users) take a bath area by area. This makes it possible to use information as to whether the users take a bath area by area in order to grasp the incidence rate of a cold or influenza area by area.

Further, the bath device 300 may be desirably provided with an agitation unit configured to agitate hot water in the bathtub. This makes it possible to make the hot water temperature in the bathtub to be uniform, whereby it is possible to accurately measure a change in hot water temperature in the bathtub. In other words, this is advantageous in accurately obtaining an internal body temperature of the user.

Further, it is desirable to automatically make the hot water temperature in the bathtub to be uniform by the agitation unit when the user is taking a bath. This is advantageous in reducing cumbersomeness involved in health management of the user. In view of the above, the bath device 300 may be desirably provided with a bath detection unit configured to detect whether the user is taking a bath, and the agitation unit may be configured to agitate hot water in the bathtub every predetermined time interval, after the bath detection unit detects that the user is taking a bath.

Further, the water temperature measuring unit 308 may be configured to measure the temperature of hot water a number of times when the user is taking a bath. This makes it possible to measure a change in hot water temperature over time. This is advantageous in separately calculating a heat capacity of the user's body and an internal body temperature of the user from each other.

Further, the agitation unit may be desirably configured to agitate hot water in the bathtub a number of times. This makes it possible to enhance the measurement precision, in the case where the temperature of hot water is measured a number of times when the user is taking a bath.

Further, the bio-information measuring unit 320 may be further provided with a water surface temperature measuring unit configured to measure the surface temperature of hot water in the bathtub. The water surface temperature measuring unit is disposed within the bathroom, and is constituted of a thermography device, for instance. This makes it possible to measure heat radiation from the hot water surface. This is advantageous in accurately calculating an internal body temperature of the user.

Further, a combined use of the water surface temperature measuring unit configured to measure the surface temperature of hot water in the bathtub, and the skin surface temperature measuring unit 307 configured to measure the skin surface temperature of the user makes it possible to calculate a core body temperature of the user. This is desirable for grasping the health condition of the user with high precision.

Further, it is desirable to dispose a water supply port through which hot water is supplied into the bathtub, and a water drainage port through which waste water is discharged from the bathtub at positions away from each other. For instance, it is desirable to form a water supply port and a water drainage port in inner surfaces of the bathtub facing each other. Alternatively, it is desirable to dispose a water supply port and a water drainage port at positions away from each other by one meter or longer. This is advantageous in measuring a core body temperature with high precision, even in the case where the bath device 300 is not provided with an agitation unit.

Further, the bath device 300 may be provided with a hot water replenishment unit configured to replenish the bathtub with hot water in order to prevent lowering of the hot water temperature in the bathtub when the user is taking a bath.

Further, the bio-information measuring unit 320 may be provided with a replenished hot water temperature measuring unit configured to measure the temperature of hot water to be replenished by the hot water replenishment unit. According to this configuration, dividing the quantity of heat of hot water replenished into the bathtub by a change in quantity of heat in the bathtub between before the user takes a bath and when the user is taking a bath makes it possible to calculate a quantity of heat of the user before the user takes a bath and when the user is taking a bath with high precision, even in the case where hot water is replenished. This is advantageous in measuring the core body temperature.

Further, the bath device 300 may be desirably provided with a hot water reservation tank configured to store hot water in order to enhance the measurement precision of a temperature of hot water to be replenished. The replenished hot water temperature measuring unit may be configured to measure the temperature of hot water stored in the hot water reservation tank. This is advantageous in measuring the temperature of hot water to be replenished with high precision, whereby it is possible to measure the core body temperature with high precision.

Further, a degree of thermal conductivity from an internal deep part of a living body to the skin surface of the living body varies depending on the blood flow rate. Accordingly, the bio-information measuring unit 320 may be configured to acquire bio-information which depends on the blood flow rate, such as a heart sound, a pulse wave, or an electrocardiogram. About 90% of thermal conductivity of a living body is performed by blood flow. Accordingly, the degree of thermal conductivity greatly changes by a blood flow rate. In view of the above, measuring in advance a relationship (a function) between the blood flow rate and the degree of thermal conductivity of each of the users, and storing the relationship as a function makes it possible to calculate a degree of thermal conductivity of the user's inner body when the user is taking a bath. This is advantageous in obtaining an internal body temperature of the user before the user takes a bath with high precision.

Further, the bio-information measuring unit 320 may be provided with a room temperature measuring unit configured to measure the room temperature of the bathroom, a humidity measuring unit configured to measure the humidity of the bathroom, or an atmospheric pressure measuring unit configured to measure the atmospheric pressure of the bathroom. In this configuration, it is possible to calculate a vapor pressure of the hot water surface from the room temperature, the humidity, and the atmospheric pressure of the bathroom, and to calculate the amount of evaporation and the heat of vaporization of hot water. This makes it possible to accurately calculate a change in quantity of heat within the bathtub between before the user takes a bath and after the user takes a bath, from a change in hot water temperature in the bathtub between before and after the user takes a bath; and to calculate a core body temperature of the user.

Further, the bath device 300 may be desirably configured to make the temperature of the bathroom to be close to the temperature of the bathtub in order to increase the humidity of the bathroom. This makes it possible to reduce an influence of a change in hot water temperature due to heat of vaporization, whereby it is possible to accurately calculate an internal body temperature of the user.

Further, the bath device 300 may be provided with an illumination adjusting unit configured to adjust the color of illumination of the bathroom. Adjusting the color of illumination of the bathroom into a color capable of providing an enhanced relaxation effect by the illumination adjusting unit makes it possible to promote recovery of the physical condition of the user.

Further, the bio-information measuring unit 320 may be provided with a body weight measuring unit 310 configured to measure the weight of the user. The body weight measuring unit 310 is configured to measure the weight of the bathtub, for instance. The body weight measuring unit 310 is configured to measure the weight of the bathtub before the user takes a bath in the bathtub, measure the weight of the bathtub when the user is taking a bath, and measure the weight of the user from a change in measured weight of the bathtub. Further, the body weight measuring unit 310 is capable of measuring a change in user's weight over time when the user is taking a bath.

Further, the bio-information measuring unit 320 may be provided with a water level measuring unit 311 configured to measure the water level of water in the bathtub, and a body volume measuring unit 312 configured to measure the body volume of the user based on a change in water level measured by the water level measuring unit 311. Further, the bio-information measuring unit 320 may be provided with a body fat percentage calculating unit 313 configured to calculate a body density of the user based on the body volume of the user measured by the body volume measuring unit 312, and based on the weight of the user measured by the body weight measuring unit 310, and to calculate a body fat percentage from the calculated body density of the user. It is possible to estimate a body fat percentage, because the body density of the user is calculated from the weight and the body volume of the user.

Further, it is possible to use the body volume of the user for personal authentication. For instance, the bath device 300 may be configured to store in advance the body volume of the user, and user information relating to the user such as the user's name in association with each other, and to specify the user corresponding to the body volume measured by the body volume measuring unit 312 when the user takes a bath.

Further, measuring the weight and the body volume of the user also makes it possible to detect that a plurality of users are taking a bath at the same time. This is advantageous in accurately measuring bio-information of each of the users.

The body volume measuring unit 312 is configured to measure the body volume of the user by detecting the amount of change in water level between before and after the user takes a bath, and by multiplying the detected change amount with the surface area of the water surface. The body fat percentage calculating unit 313 is configured to calculate a body fat percentage, based on the body volume measured by the body volume measuring unit 312. Further, it is possible to measure the volume of the head part, which is supposed to be above the water surface when the user is taking a bath. Further, the control unit 302 may be configured to store the body volume of the user measured in advance, and personal authentication information of the user in association with each other.

Further, the bio-information measuring unit 320 may be provided with a posture instructing unit configured to instruct the user taking a bath to take a certain posture by way of sound or character. Instructing the user taking a bath to take a certain posture by the posture instructing unit makes it possible to change the posture of the user taking a bath, whereby it is possible to measure the volume of a specific body part of the user under the water surface. For instance, the body volume measuring unit 312 is configured to calculate the volume of the arms by measuring the amount of change in water level between a state that the arms are under the water surface and a state that the arms are above the water surface, and by multiplying the measured change amount with the surface area of the water surface. It is needless to say that the body volume measuring unit 312 is capable of calculating a volume of any body part such as the right arm, the left arm, or the upper half of the body including the arm(s). In this way, the above configuration is advantageous in accurately estimating the amount of body fat of each of the body parts of the user.

Further, the bio-information measuring unit 320 may be desirably provided with a plurality of electrodes within the bathtub in order to measure the conductivity distribution of the internal body of the user. Using a measured conductivity of each of the body parts, and information relating to the volume of each of the body parts is advantageous in accurately estimating the amount of body fat of each of the body parts.

Further, the bath device 300 may be provided with a respiration instructing unit configured to instruct the user taking a bath of a certain respiration state. For instance, the body volume measuring unit 312 is capable of accurately measuring the body volume without an influence of the quantity of air within the lungs by measuring the body volume of the user in a state that the user has completely exhaled, and the body fat percentage calculating unit 313 is capable of accurately estimating a body fat percentage, based on the body volume measured by the body volume measuring unit 312.

Further, the body volume measuring unit 312 is also capable of measuring the lung capacity of the user by measuring the body volume of the user in a state that the user has completely exhaled and in a state that the user has inhaled. This makes it possible to measure the progress of COPD (chronic obstructive pulmonary disease).

Further, the body volume measuring unit 312 may be configured to measure the average quantity of air in the lungs and the quantity of incoming/outgoing air at the time of respiration, based on an average body volume and a fluctuation range of the body volume at the time of respiration, by measuring a change in body volume over time in a state that the user is breathing. This makes it possible to memorize the average quantity of air in the lungs and the quantity of incoming/outgoing air at the time of respiration on the daily basis.

Further, the water level measuring unit 311 may be configured to measure a change in water level in the bathtub for a predetermined time in a state that the user is in the bathtub. Further, the bio-information measuring unit 320 may be provided with a respiration rate calculating unit 314 configured to calculate a respiration rate of the user for a predetermined time, based on a change in water level measured by the water level measuring unit 311 for the predetermined time.

Further, the bathtub may be provided with a plurality of seating platforms whose distances from the water surface differ from each other. This allows for the user to easily reproduce different postures when the user is seated on the seating platforms within the bathtub. This is advantageous in acquiring bio-information (volume) of each of the body parts with high precision.

Further, the bathtub may be provided with a plurality of arm rests on which the user's arms are rested, or a plurality of foot rests on which the user's feet are rested. This allows for the user to easily reproduce different postures. This is advantageous in acquiring bio-information (volume) of each of the body parts with high precision.

Further, the body volume measuring unit 312 may be configured to measure the body volume of the user by changing the water level by supply or discharge of hot water. This makes it possible to calculate the volume of each of the body parts of the user, without forcing the user to change his or her posture.

For instance, the bath device 300 may be desirably provided with a mode at which the body volume of the user is measured in a state that the user submerges his or her whole body in hot water in the bathtub. This is advantageous in measuring the volume of the whole body of the user with high precision, and in accurately estimating the body fat percentage of the user.

Further, the bath device 300 may be desirably provided with a mode at which the body volume of the user is measured in a state that the water surface is substantially flush with the vicinity of the user's neck. It is possible to measure the volume of the user's neck whose sectional area is relatively small with high precision, even in the case where the water surface level fluctuates due to a slight difference of the user's posture on the daily basis.

Further, the bath device 300 may be desirably provided with a mode at which the body volume of the user is measured in a state that the water surface is substantially flush with the vicinity of the user's waist. This makes it possible to avoid that fluctuations in the quantity of air in the lungs by respiration may affect the measurement precision of the body volume. This is advantageous in measuring only the body volume or the body fat percentage of the lower half of the body with high precision.

Likewise, it is desirable to obtain a heat capacity, a thermal conductivity, and an internal body temperature of each of the body parts of the user in order to obtain a heat capacity, a thermal conductivity, and an internal body temperature of the user. This makes it possible to acquire bio-information of each of the body parts of the user. As well as the aforementioned body volume measurement, the water temperature measuring unit 308 may be configured to measure a change in hot water temperature by instructing the user to change his or her posture in such a manner that bio-information of an intended body part can be measured.

Further, the skin surface temperature measuring unit 307 may be configured to detect each of the body parts by e.g. pattern matching, and to measure the skin surface temperature of each of the detected body parts.

Measuring a heat capacity, a thermal conductivity, a skin surface temperature, and an internal body temperature of each of the body parts makes it possible to grasp the muscular fatigue or the blood flow rate of each of the body parts of the user. Accordingly, as will be described in the fourth embodiment, it is possible to present, via a net work, an apparatus such as a massage chair for promoting recovery from fatigue after the user takes a bath, with a body part mostly requiring massage. This allows for efficient recovery from fatigue.

Further, the bio-information measuring unit 320 may be provided with a sound velocity measuring unit configured to measure the sound velocity of each of the body parts. This makes it possible to measure the core body temperature of each of the internal body parts of the user, and to grasp a thermal state of each of the internal body parts of the user. This makes it possible to present an apparatus such as as a massage chair for promoting recovery from fatigue after the user takes a bath, with a body part mostly requiring massage. This allows for efficient recovery from fatigue.

The sound velocity measuring unit includes a sound source disposed on an inner side surface of the bathtub and configured to generate a sound wave toward a part of the user's body, a sound receiving unit disposed on an inner side surface of the bathtub at such a position as to face the sound source and configured to receive the sound wave generated by the sound source, and a sound velocity calculating unit configured to measure the time from the point of time when the sound wave is generated in the sound source to the point of time when the sound wave is received by the sound receiving unit for measuring a sound velocity. Different core body temperatures result in different sound velocities. Accordingly, the core body temperature calculating unit is stored in advance with a table, in which sound velocities and core body temperatures are correlated to each other, and a core body temperature corresponding to a sound velocity calculated by the sound velocity calculating unit is read from the table.

In the above configuration, the sound source and the sound receiving unit do not have to be in contact with the user's body. The sound velocity calculating unit may be configured to measure a sound wave propagation time required for a sound wave to propagate from the sound source to the sound receiving unit via a part of the user's body.

Further, the bio-information measuring unit 320 may be provided with a light absorption rate measuring unit configured to measure the light absorption rate of each of the internal body parts of the user. This makes it possible to measure the core body temperature of each of the internal body parts of the user, and to grasp a thermal state of each of the internal body parts of the user.

The light absorption rate measuring unit includes a light source disposed on an inner side surface of the bathtub and configured to emit light toward a part of the user's body, a light receiving unit disposed on an inner side surface of the bathtub at such a position as to face the light source and configured to receive the light emitted from the light source, and a light absorption rate calculating unit configured to calculate a light absorption rate of a part of the user's body from the intensity of light received by the light receiving unit. The light absorption rate calculating unit is stored in advance with intensities of light that does not transmit through a part of the user's body; and is configured to calculate a light absorption rate of a part of the user's body, based on the intensity of light transmitted through the part of the user's body, and based on the pre-stored intensity of light that does not transmit through the part of the user's body.

Different core body temperatures result in different light absorption rates. Accordingly, the core body temperature calculating unit is stored in advance with a table, in which light absorption rates and core body temperatures are correlated to each other, and a core body temperature corresponding to a light absorption rate calculated by the light absorption rate calculating unit is read from the table.

A light absorption rate differs depending on a component of the body. Accordingly, it is possible to measure a component of the user's body, based on a light absorption rate.

Further, the bath device 300 in the embodiment may be provided with a bathroom cleaning unit configured to clean the entirety of the inside of the bathroom. This makes it possible to clean each of the sensors configured to acquire bio-information of the user. This allows for high precision measurement and more appropriate health management.

Further, the bath device 300 may be provided with a light source configured to emit ultraviolet light toward the inside of the bathroom. This makes it possible to sterilize the inside of the bathroom. Accordingly, this allows for high precision measurement and more appropriate health management.

Further, the bath device 300 may be provided with a bathroom dryer unit configured to dry the inside of the bathroom, or a bathroom ventilator unit configured to ventilate the inside of the bathroom in order to prevent propagation of germs.

Further, the bath device 300 may be provided with an electric power supply unit configured to wirelessly supply electric power to the devices within the bathroom by magnetic resonance or electromagnetic induction. This makes it possible to wirelessly supply electric power to the devices within the bathroom.

Further, the electric power supply unit may desirably include a coil wound around the entirety of the bathroom. This makes it possible to supply electric power to the devices, no matter where the devices are installed in the bathroom.

Further, a rate of change in sound velocity due to a temperature change differs between fat and muscle. Accordingly, a combined use of a core body temperature calculating unit configured to calculate a core body temperature of the user and a sound velocity measuring unit configured to measure a sound velocity makes it possible to measure a body fat percentage of the user. Further, measuring the body fat percentage of each of the body parts of the user allows for the user to diet mostly on a body part having a high body fat percentage, with use of a diet machine using vibration or electromagnetic wave after the user takes a bath. This is advantageous in health improvement by efficient dieting.

Further, the bath device 300 is provided with a personal authentication unit configured to authenticate the user by fingerprint, iris, or vein. Personal authentication information obtained by the personal authentication unit is stored in the control unit 302 together with bio-information such as electrocardiograms. This makes it possible to specify the user even in the case where a plurality of users use the bath device 300. This is advantageous in performing health management of each of the users.

Referring to FIG. 2 and FIG. 3, the bath device 300 is provided with a fingerprint authentication unit 303 as an example of the personal authentication unit. The fingerprint authentication unit 303 is disposed on a door knob of the bathroom, on a wall surface of the bathtub 330, or on a wall surface of the bathroom, for instance. The fingerprint authentication unit 303 is configured to specify the user by the fingerprint. This makes it possible not only to reduce cumbersomeness involved in health management of the user but also to securely acquire fingerprint information. The fingerprint authentication unit 303 corresponds to an example of a user specifying unit.

Further, the bath device 300 may be provided with a user verification unit configured to verify whether an authenticated user and the user taking a bath are identical to each other. The user verification unit is constituted of a user interface configured to verify the user taking a bath by sound or character. This is advantageous in accurately performing health management of each of the users.

Further, the bath device 300 may be provided with a user number detecting unit configured to detect the number of users within the bathroom or within the bathtub. This makes it possible to prevent erroneous collection of bio-information of a user other than an authenticated user.

Further, the bath device 300 may be provided with a network connecting unit 315 configured to be connected to a network such as the Internet. The advantages of the above configuration will be described in the fourth embodiment. Further, the bath device 300 (a bio-information acquiring terminal) in the embodiment may be provided with the network connecting unit 315, or may be provided with the control unit 302. This makes it possible to reduce the amount of information to be transmitted, whereby it is possible to select a more inexpensive network connecting unit.

Further, the bath device 300 may be provided with the display unit 316 configured to display various information.

Figure 5:
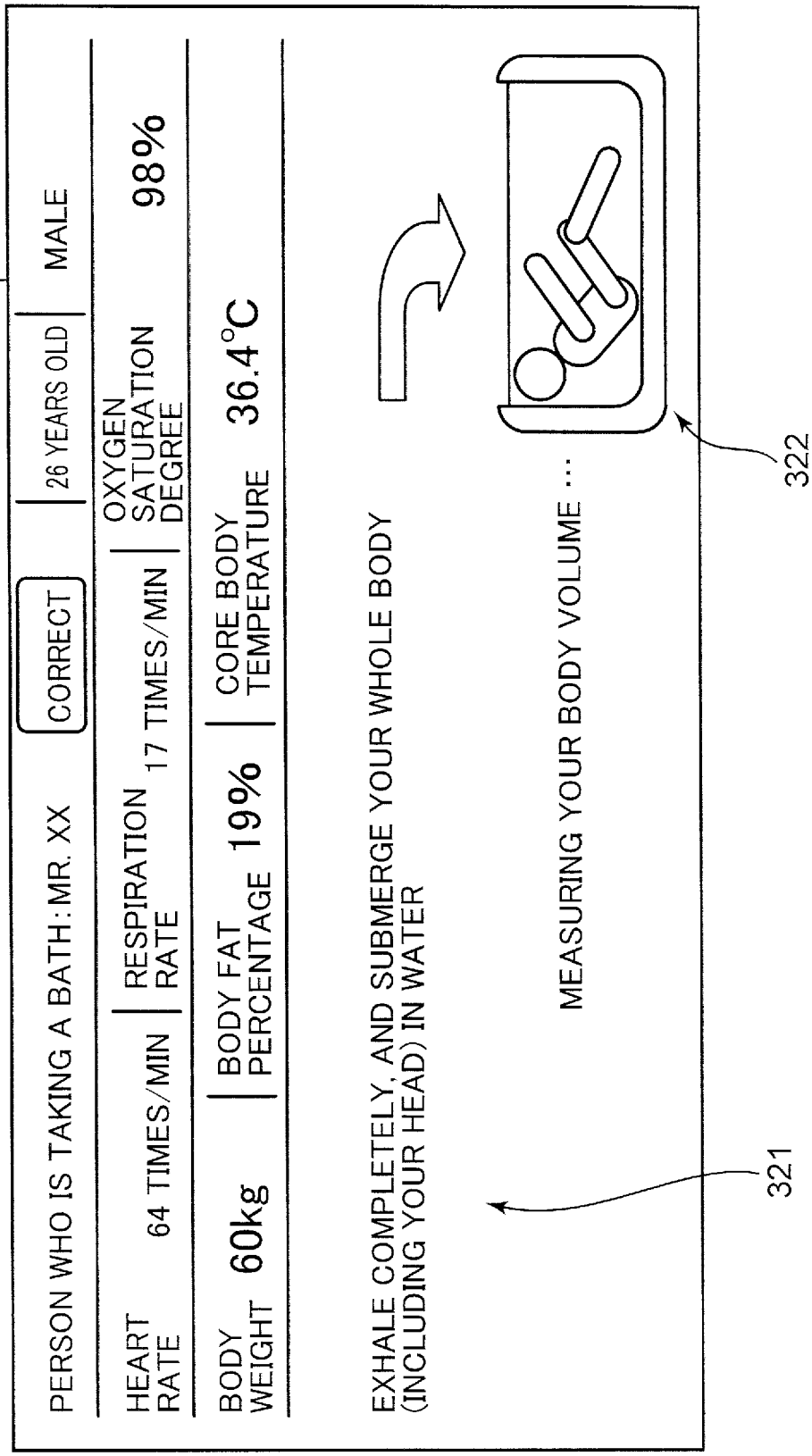
FIG. 5 is a diagram illustrating an example of a display screen to be displayed on a display unit of the bath device.

FIG. 5 is a diagram illustrating an example of a display screen to be displayed on the display unit of the bath device. As illustrated in FIG. 5, the display unit 316 is configured to display the name, the age, and the sex of the user taking a bath. Information relating to the name, the age, and the sex of the user taking a bath is input and stored in advance by the user.

Further, the display unit 316 is configured to display bio-information of the user taking a bath. In FIG. 5, the display unit 316 displays the heart rate, the respiration rate, the oxygen saturation degree, the weight, the body fat percentage, and the core body temperature as bio-information. The bio-information illustrated in FIG. 5 is an example. Bio-information other than the heart rate, the respiration rate, the oxygen saturation degree, the weight, the body fat percentage, and the core body temperature may be displayed.

Further, the display unit 316 is configured to display an instruction to be presented to the user taking a bath. For instance, in FIG. 5, the display unit 316 displays character information 321 indicating "COMPLETELY EXHALE, AND SUBMERGE YOUR WHOLE BODY (INCLUDING YOUR HEAD) IN WATER", and posture information 322 illustrating the posture of a user submerging his or her whole body in water in order to measure the body volume of the user.

In the case where daily changes of the health condition are measured with use of the bath device 300 in the embodiment, it is preferable to measure in a same condition each time measurement is performed. Specifically, a configuration such that the head part is not submerged in water at a certain measurement time, and the upper part of the body including the chest is not submerged in water at another measurement time is not preferable in the aspect of measurement of daily changes of the health condition. In view of the above, as illustrated in FIG. 5, displaying a screen to instruct the user to take a specific posture at a measurement time makes it possible to perform measurement in a fixed measurement condition (e.g. a state that the whole body of the user is submerged in water). This is advantageous in enhancing measurement precision of a change in health condition.

A measurement condition may be adjusted each time measurement is performed by a display method other than the display method illustrated in FIG. 5. For instance, a measurement condition may be adjusted each time measurement is performed by fixing the body volume of the user who is submerged in water each time measurement is performed. The display unit 316 is configured to display an image representing an instruction to the user to submerge himself or herself in water to such a depth that the body volume to be measured by the body volume measuring unit 312 is equal to a predetermined fixed value. This makes it possible to adjust the body volume of the user who is submerged in water each time measurement is performed.

In the above configuration, the bath device 300 may be provided with an instruction information output unit (not illustrated) other than the display unit 316, and the instruction information output unit may be configured to instruct the user of a depth to which the user should submerge himself or herself. For instance, the instruction information output unit may include an instruction light output unit configured to output instruction light (visible light) at a predetermined height position within the bathtub. In this configuration, the display unit 316 may display a pictorial image indicating "SUBMERGE YOURSELF SO THAT WATER SURFACE IS FLUSH WITH LIGHT LEVEL" or "GET OUT OF WATER SO THAT WATER SURFACE IS FLUSH WITH LIGHT LEVEL" during a time period from the point of time when the user takes a bath to the point of time when the instruction light level is flush with the water surface level. The display unit 316 may be configured to display a pictorial image indicating "MEASUREMENT STARTS IN THIS CONDITION. DO NOT MOVE YOUR BODY" when the instruction light level is flush with the water surface level, and the instruction information output unit may be configured to change the color of instruction light or to stop outputting instruction light. Thereafter, the bio-information measuring unit 320 may be configured to start measuring bio-information (body volume).

Further, an instruction to the user or a state presentation as described above is not limited by indication using the display unit 316, but may be performed by way of sound using a sound output unit (not illustrated).

Second Embodiment

Figure 6:
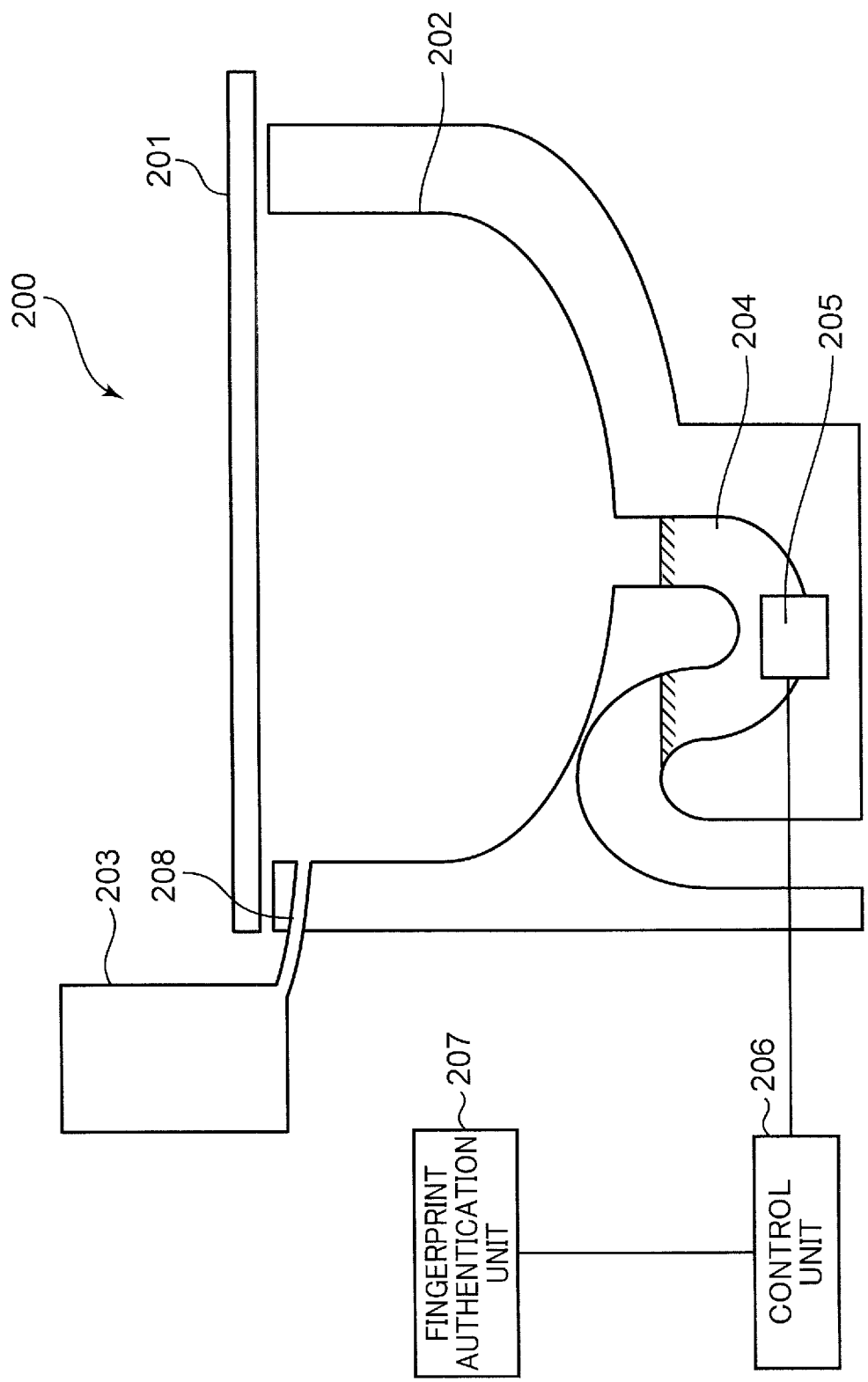
FIG. 6 is a schematic diagram illustrating an example of a bio-information acquiring terminal according to a second embodiment of the invention.

FIG. 6 is a schematic diagram illustrating an example of a bio-information acquiring terminal according to the second embodiment.

In the second embodiment, a toilet device 200 is an example of a bio-information acquiring terminal provided with a bio-information acquiring unit. In the embodiment, for instance, a waste component measuring unit 205 is configured to measure the amount of components or the concentration of components of the wastes.

The user uses the toilet device 200 for discharging the wastes. When the user uses the toilet device 200, the waste component measuring unit 205 is configured to measure the amount of components or the concentration of components of the wastes. The acquired information relating to the component amount or the component concentration of the wastes is stored in a control unit 206 provided with a storing unit.

In the following, the details of the bio-information acquiring terminal in the embodiment is described.

Figure 7:
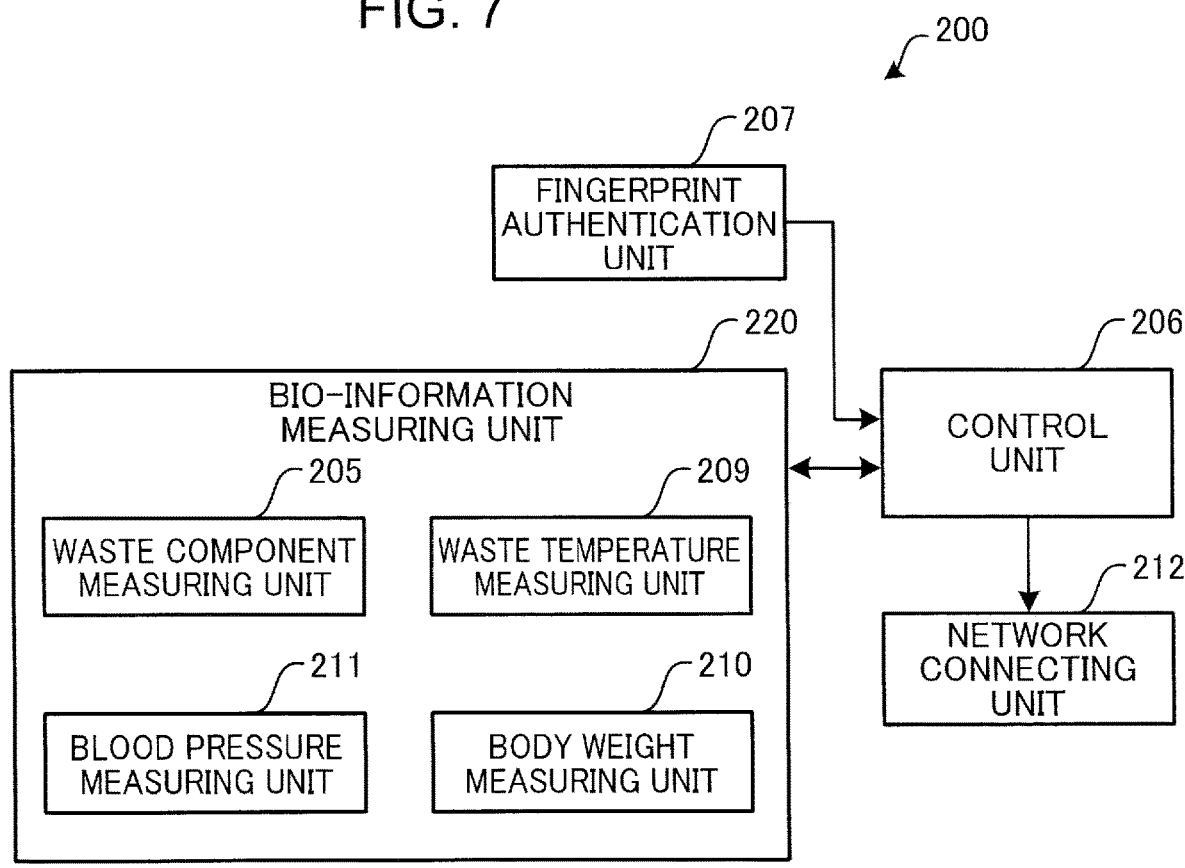
FIG. 7 is a block diagram illustrating a configuration of a toilet device in the second embodiment.

FIG. 7 is a block diagram illustrating a configuration of the toilet device in the second embodiment.

The toilet device 200 is provided with a bio-information measuring unit 220, the control unit 206, a fingerprint authentication unit 207, and a network connecting unit 212. The bio-information measuring unit 220 is configured to measure bio-information of the user from the wastes of the user. The bio-information measuring unit 220 is provided with a waste component measuring unit 205, a waste temperature measuring unit 209, a body weight measuring unit 210, and a blood pressure measuring unit 211. Further, the toilet device 200 is provided with a toilet bowl 202 configured to receive the wastes of the user, and a drainage pipe 204 configured to convey the wastes received by the toilet bowl 202 to the waste component measuring unit 205.

The waste component measuring unit 205 is disposed in the inside of the drainage pipe 204 which is configured to convey the wastes received by the toilet bowl 202, and to measure the components of the wastes. The waste component measuring unit 205 is configured to measure urinary sugar or urinary protein contained in the wastes. The waste component measuring unit 205 is also configured to measure the blood component contained in the wastes.

The waste component measuring unit 205 is configured to measure the amount or the concentration of the components contained in the wastes such as urine or feces. For instance, the waste component measuring unit 205 is configured to irradiate near infrared light or far infrared light toward the discharged urine or feces, and to measure the absorption spectrum for analyzing the component concentration of the wastes. This makes it possible to analyze multiple components without the need of expendable supplies, and to manage the conditions of many diseases easily.

Further, the waste component measuring unit 205 may be configured to measure the optical rotation or the optical rotatory dispersion of urine with use of near infrared light for analyzing the component concentration of the wastes, as well as the aforementioned configuration. This makes it possible to measure the concentration of an organic component such as urinary sugar or urinary protein with high precision, without the need of expendable supplies, whereby it is possible to enhance the precision of a screening test or prognostic management of diabetes, kidney diseases, or the like.

Further, the waste component measuring unit 205 may be configured to measure the component concentration of the wastes with use of Raman spectroscopic analysis technology. This makes it possible to measure the component concentrations of components of many kinds, whereby it is possible to check the conditions of diseases of many kinds.

Further, the waste component measuring unit 205 may be configured to detect a component concentration with use of at least an optical rotation of the wastes, and infrared spectroscopy or Raman spectroscopy. Detection of an optical rotation makes it possible to obtain the concentration of the components including urinary sugar and urinary protein contained in urine, and performing infrared spectroscopy or Raman spectroscopy makes it possible to isolate urinary sugar and urinary protein from each other.

In a component analysis using a principle such as absorption spectrum, optical rotation, optical rotatory dispersion, or Raman spectroscopy, noise is generated in a measurement result due to a temperature change. In view of the above, the bio-information measuring unit 220 may be provided with a pipe temperature measuring unit configured to measure the temperature of the inside of the drainage pipe 204. This makes it possible to measure the component concentration with high precision.

Further, the bio-information measuring unit 220 may be provided with a temperature calculating unit configured to calculate the temperature of the wastes or the internal body temperature of the user, based on a change in temperature of the inside of the drainage pipe 204 before and after the user uses the toilet, which is measured by the pipe temperature measuring unit. Further, the toilet device 200 may be provided with a presentation unit configured to present the calculated waste temperature or the calculated internal body temperature of the user. This makes it possible to easily manage the internal body temperature of the user on the daily basis. The presentation unit may preferably be a display unit such as a liquid crystal monitor.

Further, examples of the pipe temperature measuring unit are a thermistor and a thermocouple.

Further, the bio-information measuring unit 220 may be provided with a waste temperature measuring unit 209 configured to measure the temperature of the wastes being discharged in a non-contact manner by measuring infrared light of a wavelength of 5 μm to 20 μm in the inside of the toilet bowl 202. The waste temperature measuring unit 209 is configured to measure the temperature of the wastes. Measuring the temperature of the wastes makes it possible to estimate the rectal temperature of the user. This method costs high, as compared with a method for measuring the temperature of the inside of the drainage pipe 204 before and after the user uses the toilet. However, this method is advantageous in accurately measuring the rectal temperature, and is advantageously used for health management of the user.

Examples of the waste temperature measuring unit 209 are a thermopile, a bolometer, and a photodiode.

Further, the bio-information measuring unit 220 may be provided with a waste discriminating unit configured to discriminate the wastes such as solid feces, feces of ordinary softness, or loose feces from each other. This makes it possible to grasp the bowel condition of each of the users such as constipation or diarrhea, and to record the cycle of evacuating the bowels.

Further, the bio-information measuring unit 220 may be provided with a toilet seat temperature measuring unit disposed on a toilet seat 201 and configured to measure the temperature of the thighs of the user. This makes it possible to measure the temperature of the thighs of the user. Accordingly, it is possible to estimate the condition of blood circulation of the user by detecting a temperature difference between the body temperature and the thigh temperature.

Further, the toilet device 200 may be provided with a heater configured to irradiate far infrared light toward the thighs for warming the thighs, in the case where the temperature of the thighs is lower than a predetermined temperature.

Further, a component analysis using a principle such as absorption spectrum, optical rotation, optical rotatory dispersion, or Raman spectroscopy also makes it possible to acquire a component concentration of saliva, expired air, sweat, or blood, in addition to the wastes. In view of the above, the waste component measuring unit 205 may be configured to perform component analysis of saliva, expired air, sweat, or blood, in addition to the wastes. This makes it possible to provide health management on the conditions of many diseases at a low cost.

For instance, a cell unit configured to store saliva, expired air, sweat, or blood, other than the wastes may be inserted in the waste component measuring unit 205, and the waste component measuring unit 205 may be configured to measure the components such as saliva, expired air, sweat, or blood stored in the cell unit.

Further, the waste component measuring unit 205 may be configured to employ a biochemical approach such as an oxygen method or an ion-selective electrode method. This makes it possible to acquire bio-information at a low cost.

Further, the waste component measuring unit 205 may be constituted of electrodes, and may be configured to measure the concentration of salt contained in the wastes. This makes it possible to manage the concentration of salt contained in the wastes, which is advantageously used for prevention or prognostic management of high blood pressure symptoms.

Further, in the embodiment, the bio-information measuring unit 220 may be provided with a waste volume measuring unit configured to measure the volume of the wastes. Further, the bio-information measuring unit 220 may be provided with a waste mass measuring unit configured to measure the mass of the wastes. This makes it possible to calculate the amounts of various components in cooperation with the waste component measuring unit 205, whereby it is possible to monitor the conditions of many diseases. For instance, information relating to the volume of urine as the wastes is necessary in order to calculate creatinine clearance used in screening or prognostic management of kidney diseases to be described later. In view of the above, measuring the volume of the wastes makes it possible to perform screening or prognostic management of kidney diseases.

In the case where a salt concentration is measured by the waste component measuring unit 205, it is possible to calculate the amount of salt in the wastes for 24 hours by measuring the volume and the mass of the wastes. This makes it possible to manage the amount of salt contained in the wastes. This is advantageous in providing a bio-information acquiring terminal useful for prevention or prognostic management of high blood pressure symptoms.

The waste volume measuring unit can calculate the volume of the wastes by measuring the water level in the case where the wastes are present in water in the inside of the drainage pipe 204, and in the case where the wastes are not present in water in the inside of the drainage pipe 204. Further, the waste volume measuring unit may be configured to measure the volume of the wastes, based on a fluid rate measured by a fluid meter provided in the inside of the drainage pipe 204. The above configuration makes it possible to obtain the volume of the wastes with high precision. Further, the toilet device 200 may be provided with a water expelling unit configured to expel water and the like from the inside of the drainage pipe 204 before the user uses the toilet. The above configuration makes it possible to measure the volume of the wastes with high precision.

Further, the waste mass measuring unit is configured to measure the mass of the wastes by monitoring a change in total mass of the toilet device 200. Further, the waste mass measuring unit may be configured to measure the mass of the wastes by measuring the weight of the user before and after the user uses the toilet. The method for monitoring a change in total mass of the toilet device 200 is desirable because it is possible to measure the mass of the wastes with high precision. Further, the method for measuring the weight of the user before and after the user uses the toilet is desirable, because it is possible to use information relating to the user's weight as bio-information for health management, or to use information relating to the user's weight for personal authentication to be described later.

In the embodiment, the waste component measuring unit 205 may be configured to detect occult blood in the wastes. This is applicable to screening of malignant tumors in the urinary system. Further, as described above, the waste component measuring unit 205 may be desirably configured to measure the concentration of urinary sugar, which is applicable to screening of diabetes. Further, the waste component measuring unit 205 may be desirably configured to measure the concentration of urinary protein, which is applicable to screening of kidney diseases such as renal failures.

Further, the toilet device 200 may be provided with the toilet seat 201 on which the user is seated. This makes it possible for the user to use the toilet in a relaxed posture.

Further, the bio-information measuring unit 220 may be provided with the body weight measuring unit 210 configured to measure the weight of the user. The body weight measuring unit 210 is provided on the toilet seat 201 on which the user is seated. The body weight measuring unit 210 is configured to measure the weight of the user from a force exerted on the toilet seat 201 before and after the user uses the toilet. This configuration makes it possible to obtain the user's weight with high precision, as compared with a configuration, in which the user's weight is measured in a standing posture. Further, it is possible to measure the weight of the wastes by subtracting the user's weight after the user uses the toilet, from the user's weight before the user uses the toilet.

In view of the above, the toilet seat 201 may be desirably designed to such a height that the user's feet are above the toilet floor when the user is seated on the toilet seat 201. This makes it possible to accurately measure the user's weight.

Further, the toilet seat 201 may be desirably provided with a body temperature measuring unit configured to measure the body temperature of the user. This makes it possible to record daily changes of the body temperature of the user.

Further, the bio-information measuring unit 220 may be provided with a blood pressure measuring unit 211 configured to measure the blood pressure of the user when the user uses the toilet. This makes it possible to prevent the user from suffering from hemorrhoids due to overstrain.

An example of the blood pressure measuring unit 211 is a sound receiving unit disposed on the toilet seat 201, for instance. Measuring the magnitude of the heart sound by the sound receiving unit makes it possible to estimate the blood pressure.

Further, the bio-information measuring unit 220 may be provided with a blood flow rate measuring unit configured to measure the blood flow rate of the user. An example of the blood flow rate measuring unit is a pulse oximeter constituted of a light source and a light receiving unit. This makes it possible to calculate the pressure of vein in the vicinity of the anus, whereby it is possible to prevent the user from suffering from hemorrhoids, as well as the aforementioned configuration.

Further, the blood pressure measuring unit 211 or the blood flow rate measuring unit are usable in separately detecting occult blood in the wastes, and bleeding of hemorrhoids.

Further, the toilet device 200 may be provided with a washing function of washing the toilet bowl 202. This makes it possible to inspect the components of the wastes with high precision, whereby it is possible to monitor the health condition with high precision.

As an example of the washing function, there is used a water supply unit constituted of a water supply tank 203 for storing water, and a water feeding pipe 208 configured to feed water from the water supply tank 203 to the toilet bowl 202. Using tap water as water in the water supply tank 203 and feeding the water to the toilet bowl 202 through the water feeding pipe 208 after the user uses the toilet makes it possible to wash the toilet bowl 202 at a low cost.

Further, the toilet device 200 may be provided with a personal authentication unit configured to authenticate the user by fingerprint, iris, or vein. Personal authentication information obtained by the personal authentication unit is stored in the control unit 206 together with bio-information such as the component concentration of the wastes. This makes it possible to specify the user even in the case where a plurality of users use the toilet device 200. This is advantageous in providing health management of each of the users.

In FIG. 6 and FIG. 7, the toilet device 200 is provided with the fingerprint authentication unit 207 as an example of the personal authentication unit. The fingerprint authentication unit 207 is disposed on a door knob of the toilet, or on a water supply switch with which the user is allowed to supply water from the water supply tank 203 to the toilet bowl 202. The fingerprint authentication unit 207 is configured to specify the user by the fingerprint. This makes it possible not only to reduce cumbersomeness involved in health management of the user but also to securely acquire fingerprint information. The fingerprint authentication unit 207 corresponds to an example of a user specifying unit.

Further, the personal authentication unit may be configured to authenticate the user in a non-contact manner e.g. by way of iris authentication, retinal authentication, or face authentication. This makes it possible to perform personal authentication without annoying users, even in the case a plurality of users utilize the personal authentication unit. In particular, iris authentication makes it possible to accurately authenticate the users.

Further, the toilet device 200 may be provided with a user number detecting unit configured to detect the number of users within the toilet. This makes it possible to prevent erroneous collection of bio-information of users other than the authenticated users.

Further, the toilet device 200 may be provided with the network connecting unit 212 configured to be connected to a network such as the Internet. The advantages of the above configuration will be described in the fourth embodiment. Further, the toilet device 200 (a bio-information acquiring terminal) in the embodiment may be provided with the network connecting unit 212, or may be provided with the control unit 206. This makes it possible to reduce the amount of information to be transmitted, whereby it is possible to select a more inexpensive network connecting unit.

Third Embodiment

Figure 8:
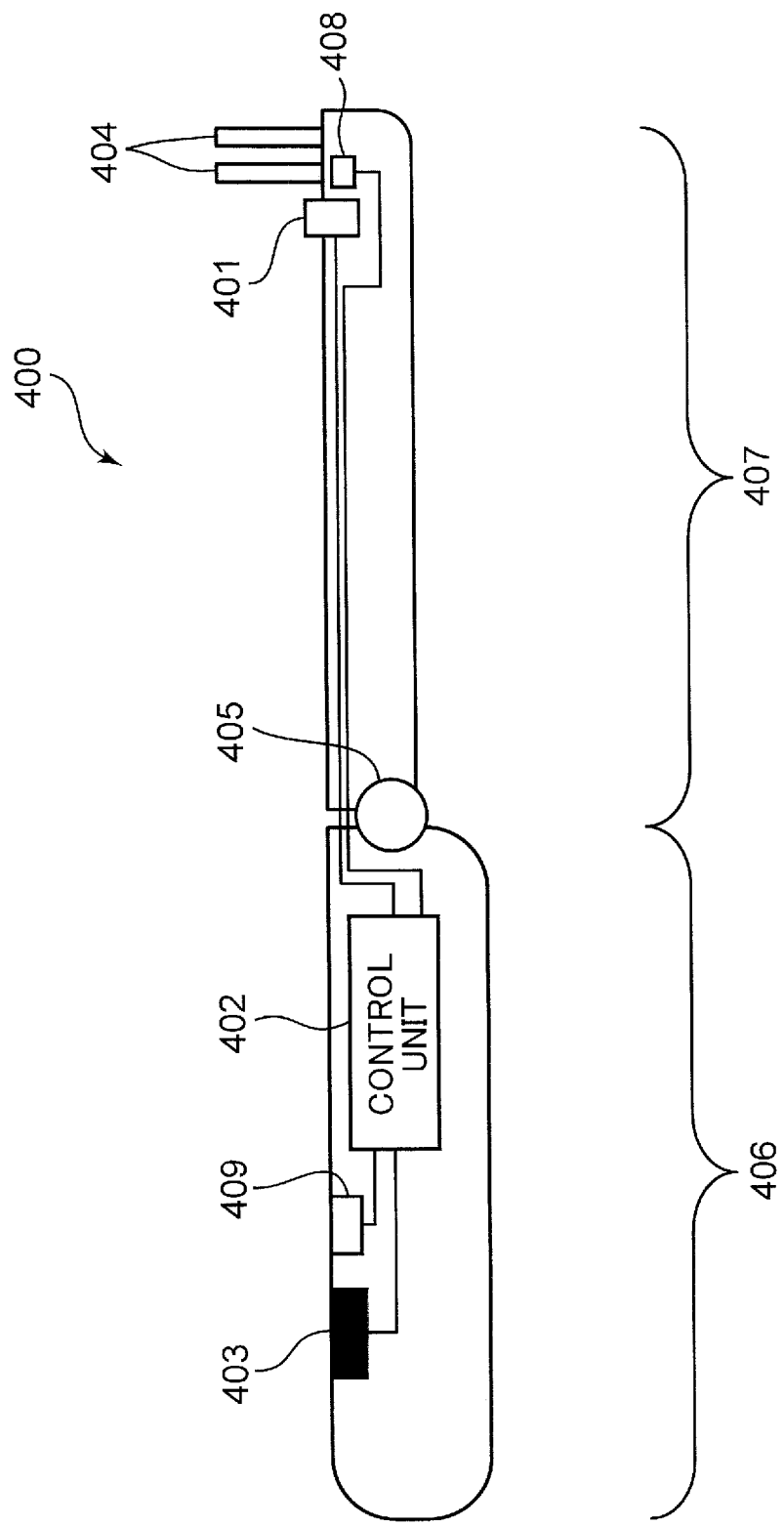
FIG. 8 is a schematic diagram illustrating an example of a bio-information acquiring terminal according to a third embodiment of the invention.

FIG. 8 is a schematic diagram illustrating an example of a bio-information acquiring terminal according to the third embodiment.

In the third embodiment, an oral cavity inspection terminal 400 is an example of a bio-information acquiring terminal provided with a bio-information acquiring unit. In the embodiment, a body fluid component measuring unit 401 is configured to measure the component concentration of body fluid of the oral cavity. The oral cavity inspection terminal 400 is provided with a grip part 406 and an oral cavity insertion part 407. The grip part 406 is held by the user. The oral cavity insertion part 407 is connected to an end of the grip part 406, and is configured to be inserted into the oral cavity. The body fluid component measuring unit 401 is disposed on the oral cavity insertion part 407.

In the embodiment, the body fluid component measuring unit 401 is configured to be inserted into the oral cavity of the user, and to measure the components of body fluid in the oral cavity. The body fluid component measuring unit 401 may be configured to measure e.g. the components such as saliva or gingival fluid from the gingival sulcus. The acquired information relating to the body fluid components is stored in a control unit 402 provided with a storing unit.

Further, the oral cavity inspection terminal 400 may be provided with a personal authentication unit such as a fingerprint authentication unit 403, as well as the foregoing embodiments. The fingerprint authentication unit 403 is configured to specify the user by the fingerprint. The control unit 402 makes it possible to manage the health condition of each of the users by storing personal authentication information and bio-information in association with each other, even in the case where a plurality of users use the oral cavity inspection terminal 400. The fingerprint authentication unit 403 corresponds to an example of a user specifying unit.

Figure 9:
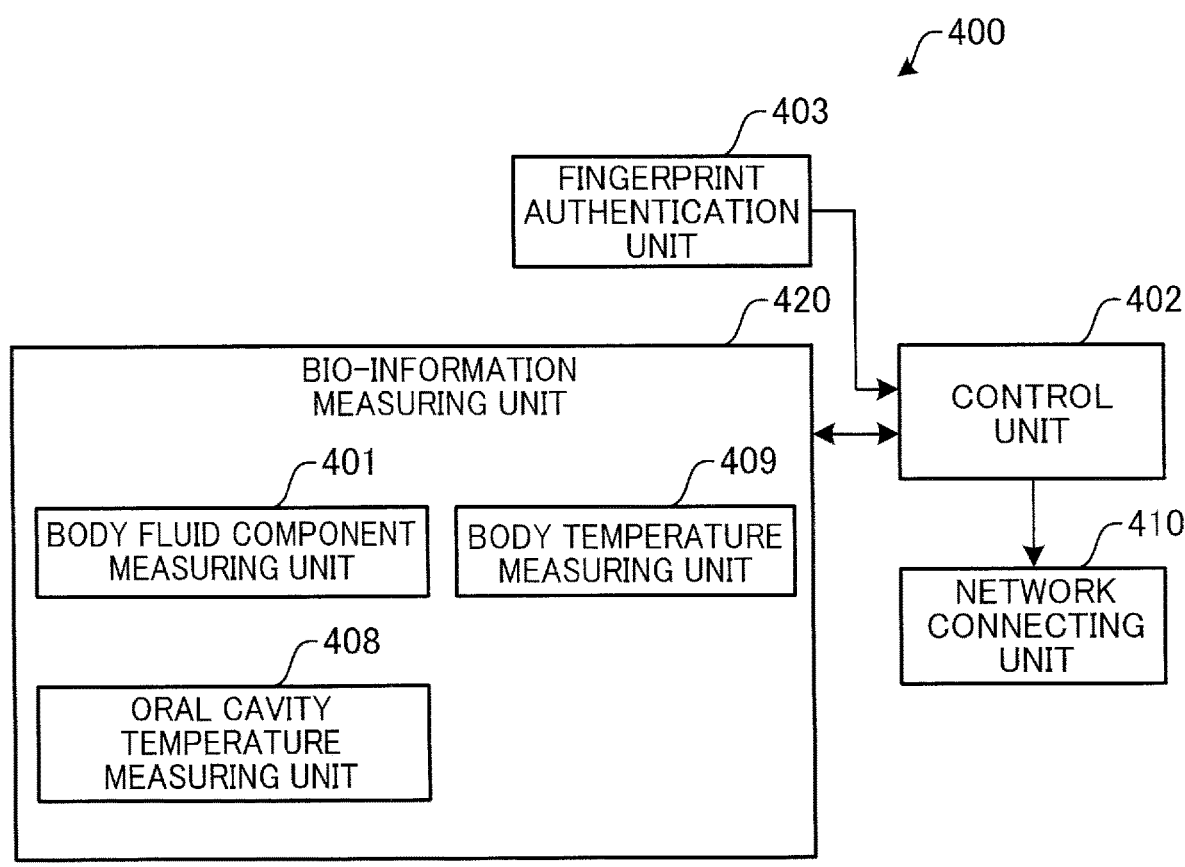
FIG. 9 is a block diagram illustrating a configuration of an oral cavity inspection terminal in the third embodiment.

FIG. 9 is a block diagram illustrating a configuration of an oral cavity inspection terminal in the third embodiment.

The oral cavity inspection terminal 400 is provided with a bio-information measuring unit 420, the control unit 402, the fingerprint authentication unit 403, and a network connecting unit 410. The bio-information measuring unit 420 is configured to measure bio-information of the user in the oral cavity of the user. The bio-information measuring unit 420 is provided with the body fluid component measuring unit 401, an oral cavity temperature measuring unit 408, and a body temperature measuring unit 409.

Further, the body fluid component measuring unit 401 may be configured to measure the component concentration of blood in the oral cavity. This makes it possible to perform health management of the conditions of many diseases.

Further, the oral cavity inspection terminal 400 may be provided with at least one protrusion 404. Forming at least one protrusion 404 makes it possible to cause bleeding in the oral cavity. This makes it possible to measure the component concentration of blood in the oral cavity with high precision.

Further, the protrusion 404 may have flexibility. This is advantageous in alleviating the pain accompanied by bleeding.

Further, the oral cavity inspection terminal 400 may be provided with a plurality of protrusions 404. This makes it possible to cause bleeding in a plurality of positions of the oral cavity. This is advantageous in measuring the component concentration of blood in a short time with high sensitivity.

Further, the oral cavity inspection terminal 400 may be provided with a driving unit 405 configured to give kinetic energy such as vibrations to the protrusion 404. The driving unit 405 is configured to vibrate the protrusion 404 formed on the oral cavity insertion part 407 by vibrating the oral cavity insertion part 407. This makes it possible to promote bleeding in the oral cavity in a short time, whereby it is possible to measure the component concentration of blood in a short time.

Further, the oral cavity inspection terminal 400 may be provided with a suppressing unit configured to suppress a force applied to a connection part connecting between the oral cavity insertion part 407 and the grip part 406 in order to suppress application of an excessive force to the protrusion 404 in contact with the oral cavity. This makes it possible to prevent damage of the oral cavity more than required.

An example of the suppressing unit is a member having flexibility. Further, the suppressing unit may be configured to alert the user, in the case where a force over a predetermined force is applied to the connection part.

Further, the driving unit 405 may be configured to stop a driving operation thereof, in the case where a force over a predetermined force is applied to the connection part. This makes it possible to prevent damage of the oral cavity more than required.

Further, the oral cavity inspection terminal 400 in the embodiment may be formed with protrusions 404 so that the protrusions 404 function as a toothbrush for cleaning the oral cavity by removing food remnants from the surfaces of the teeth. This makes it possible to clean the oral cavity and to inspect the components of body fluid in the oral cavity at the same time. This is advantageous in reducing cumbersomeness involved in health management of the user.

Further, the oral cavity inspection terminal 400 in the embodiment may be formed with a protrusion 404 so that the protrusion 404 functions as an interdental brush for cleaning the space between the adjacent teeth by inserting the protrusion 404 in the space between the adjacent teeth. This makes it possible to analyze the components of blood with high sensitivity.

Further, in the embodiment, the body fluid component measuring unit 401 is disposed on the oral cavity insertion part 407. The body fluid component measuring unit 401 may not be disposed on the oral cavity insertion part 407. For instance, the user may insert the oral cavity insertion part 407 into the oral cavity, and take out the oral cavity insertion part 407 from the oral cavity, and thereafter, may use the body fluid component measuring unit 401 installed at a place different from the installation place of the oral cavity insertion part 407. The body fluid component measuring unit 401 may be configured to inspect the components of body fluid adhered to the oral cavity insertion part 407. This makes it possible to make the oral cavity insertion part 407 lightweight.

Further, the grip part 406 of the oral cavity inspection terminal 400 may be configured to be detachably attachable to the oral cavity insertion part 407. This makes it possible to share the grip part 406 between the users. This is advantageous in providing a more inexpensive bio-information acquiring terminal.

Further, as described in the first and second embodiments, the body fluid component measuring unit 401 may be an absorption spectrum measuring unit configured to measure the absorption spectrum of a test substance, may be an optical rotation measuring unit configured to measure the optical rotation of a test substance, or may be a Raman spectroscopic measuring unit configured to measure the scattering spectrum of Raman scattering light from a test substance. In any of these configurations, it is possible to eliminate the need of expendable suppliers and to measure the component concentration at a low cost.

Further, in the case where the oral cavity insertion part 407 and the grip part 406 are configured to be detachably attachable to each other, the oral cavity insertion part 407 may be provided with a light source and a light receiving unit. This is advantageous in performing high-sensitivity measurement, because there is no need of joining a light guiding path for guiding light in the connection part connecting between the grip part 406 and the oral cavity insertion part 407.

Further, the grip part 406 may be provided with a light source or a light receiving unit. This is advantageous in configuring a compact oral cavity insertion part 407 at a low cost.

Further, the light source or the light receiving unit may be disposed on the outside of the oral cavity insertion part 407, and may be configured to guide light to the oral cavity insertion part 407 by a light guiding unit such as an optical fiber. This makes it possible to configure a compact oral cavity inspection terminal. Accordingly, this is advantageous in reducing the burden of the user's arm.

Further, the light source may be a laser light source or a super luminescent diode. This makes it possible to miniaturize the light source. Further, use of an optical fiber makes it possible to transmit light with high efficiency. This is advantageous in saving the electric power.

Further, the light source may be a wavelength variable light source. This is advantageous in implementing a compact oral cavity inspection terminal capable of analyzing the body fluid components of many kinds.

Further, the light source may be desirably a broadband light source configured to emit light of different wavelengths, and the light receiving unit may be desirably provided with a spectral unit configured to diffract light according to the wavelength. This is advantageous in implementing an oral cavity inspection terminal capable of analyzing the body fluid components of many kinds.

Further, in the case where the grip part 406 is provided with a light source or a light receiving unit, the grip part 406 and the oral cavity insertion part 407 are configured to be detachably attachable to each other, and bleeding in the oral cavity is promoted by vibrating the protrusion 404 by the driving unit 405, the driving unit 405 may be desirably provided with a vibration stopping period of stopping vibrations, and the body fluid component measuring unit 401 may be configured to measure the component concentration of body fluid in the oral cavity during the vibration stopping period.

This makes it possible to measure the component concentration of body fluid in the oral cavity with high precision, whereby it is possible to perform more appropriate heath management.

Further, in the configuration of irradiating light from a light source in the oral cavity through an optical fiber, the light may be emitted from the tip of at least one protrusion 404. This makes it possible to analyze the body fluid components with high precision.

Further, in the case where after the irradiated light is scattered in the oral cavity, the light is incident in the optical fiber provided in the oral cavity insertion part 407, and is guided to the light receiving unit, it is desirable to guide the light from the tip of the protrusion 404 as well as the aforementioned configuration. This makes it possible to analyze the body fluid components with high precision.

In the case where the oral cavity inspection terminal 400 is used for cleaning the oral cavity on the daily basis as a toothbrush, at least one of the protrusions 404 may be an optical fiber. This makes it possible to acquire bio-information with high sensitivity on the daily basis.

Further, in the case where at least one of the protrusions 404 is an optical fiber, the optical fiber may be a plastic fiber. This makes it possible to implement an oral cavity inspection terminal having enhanced durability.

Further, the protrusions 404 may be desirably configured to irradiate light from the tips thereof, or to receive light from the tips thereof. This makes it possible to implement an oral cavity inspection terminal having enhanced durability Further, in the case where the oral cavity inspection terminal 400 is used for cleaning the oral cavity as a toothbrush, the protrusions 404 may be desirably optical fibers, and the optical fibers may be plastic fibers. This is advantageous in enhancing the durability, and in acquiring bio-information with high sensitivity.

Further, in the case where the oral cavity inspection terminal 400 is used for cleaning the oral cavity as a toothbrush, a protrusion 404 as an optical fiber may be desirably shorter than the other protrusions 404, which are not an optical fiber. This is advantageous in implementing an oral cavity inspection terminal having enhanced durability.

Further, in the case where the oral cavity inspection terminal 400 is used for cleaning the oral cavity as a toothbrush, a protrusion 404 as an optical fiber may have the same length as the other protrusions 404, which are not an optical fiber, or may have a longer length than the other protrusions 404, which are not an optical fiber. This makes it possible to inspect the oral cavity with high sensitivity.

Further, the body fluid component measuring unit 401 may be configured to measure the amount of light to be received by the light receiving unit by causing the light source to emit the light in a state that the oral cavity insertion part 407 is not inserted in the oral cavity. This makes it possible to check whether sufficient sensitivity is obtained, to obtain a transmittance of the optical path in the oral cavity inspection terminal 400, and to check the wavelength dependency of transmittance.

Further, the oral cavity inspection terminal 400 may be provided with a replacement notifying unit configured to prompt the user to clean the optical path or to replace the oral cavity insertion part 407, in the case where the sensitivity or transmittance of the optical path to be obtained in a state that the oral cavity insertion part 407 is not inserted in the oral cavity is lower than a predetermined threshold value. The replacement notifying unit is configured to notify the user by way of light or sound. This makes it possible to inspect the oral cavity with high sensitivity.

Further, the oral cavity inspection terminal 400 may be provided with a blood component analysis completion notifying unit configured to notify the user of completion of blood component analysis. This makes it possible to suppress the user from bleeding more than required for blood component analysis.

The blood component analysis completion notifying unit may be constituted of a light emitting unit such as an LED (Light Emitting Diode) disposed on the grip part 406, or a sound output unit disposed on the handle part 406 and configured to output sound. Further, the bio-information measuring unit 420 may be provided with a detecting unit configured to detect that blood component analysis has been completed. In this configuration, the detecting unit detects that blood component analysis has been completed by detecting that the concentration of a component that is not contained in saliva but is contained only in blood is not lower than a predetermined threshold value. The detecting unit is capable of determining that blood component analysis has been completed, in the case where the concentration of hemoglobin contained in the red blood cells is not lower than a predetermined threshold value, for instance.

Further, in the case where the oral cavity inspection terminal 400 is used for cleaning the oral cavity, the oral cavity inspection terminal 400 may be provided with a cleaning completion notifying unit configured to notify the user that oral cavity cleaning has been completed. This allows for the user to complete oral cavity cleaning in a short time. The cleaning completion notifying unit may be configured to notify the user by way of light or sound, as well as the blood component analysis completion notifying unit as described above.

The cleaning completion notifying unit may be configured to detect the amount of plaque in the oral cavity, may determine that oral cavity cleaning has been completed in the case where the detected amount of plaque is not larger than a predetermined threshold value, and may notify the user of completion of oral cavity cleaning. The cleaning completion notifying unit may be configured to determine that cleaning has been completed in the case where a blood component in the oral cavity is detected, and to notify the user that oral cavity cleaning has been completed.

Further, the oral cavity inspection terminal 400 may be provided with a saliva component analysis completion notifying unit configured to notify the user that saliva component analysis has been completed. This makes it possible to analyze the components of saliva in a short time.

Further, in measuring the component concentration of blood with use of the body fluid component measuring unit 401, the body fluid measuring unit 401 may be configured to measure the concentration of a target component in comparison with the concentration of hemoglobin. This makes it possible to accurately measure the component concentration of blood. For instance, in the case where the concentration of glucose contained in blood is measured, the body fluid component measuring unit 401 compares between the concentration of hemoglobin and the concentration of glucose. The concentration of hemoglobin is substantially constant in the blood. Accordingly, comparing between the concentration of hemoglobin and the concentration of glucose makes it possible to analyze the concentration of glucose with high precision.

Further, the body fluid component measuring unit 401 may be configured to measure the concentration of a target component (e.g. glucose) before bleeding, detect bleeding, and measure the concentration of the target component at the time of bleeding. This makes it possible to measure the concentration of the target component contained in saliva, and the concentration of the target component contained in blood separately.

Further, the bio-information measuring unit 420 may be provided with the oral cavity temperature measuring unit 408 disposed on the oral cavity insertion part 407 and configured to measure the temperature of the oral cavity.

This makes it possible to measure the temperature of the oral cavity on the daily basis, and to record the body temperature on the daily basis. The oral cavity temperature measuring unit 408 is constituted of a thermistor, a thermocouple, a thermopile, a bolometer, or a photodiode, for instance. A thermistor is desirable because it is inexpensive. Further, a thermopile, a bolometer, or a photodiode made of indium antimony is desirable because they are capable of performing high-speed measurement.

Further, the bio-information measuring unit 420 may be provided with the body temperature measuring unit 409 disposed at such a position as to touch the finger of the user when the user grips the grip part 406, and configured to measure the temperature of the finger of the user. Measuring and comparing the temperature of the oral cavity and the temperature of the finger makes it possible to grasp the blood flow rate or the degree of sensitivity to the cold from the trunk to a distal part of the user's body.

Further, in the oral cavity inspection terminal 400, it is desirable to dispose the fingerprint authentication unit 403 on the grip part 406. This makes it possible to automatically specify the user during use of the oral cavity inspection terminal 400. Accordingly, this is advantageous in acquiring personal authentication information of the user with enhanced probability.

Further, the oral cavity inspection terminal 400 may be provided with a vein authentication unit disposed on the grip part 406 and configured to authenticate the user by vein. In the case where the fingerprint authentication unit 403 or the vein authentication unit is provided on the grip part 406 as described above, the shape of the grip part 406 may be such that the user is guided to grip the grip part 406 in a specific manner.

Further, the personal authentication unit such as the vein authentication unit or the fingerprint authentication unit 403 may be provided on the outside of the grip part 406 and the oral cavity insertion part 407. The personal authentication unit may be disposed on a storage stand configured to store the oral cavity inspection terminal 400 or on a charging stand configured to charge the oral cavity inspection terminal 400. This makes it possible to miniaturize the oral cavity inspection terminal 400.

Further, in the case where the oral cavity insertion part 407 and the grip part 406 are configured to be detachably attachable to each other, identification information (ID) may be provided for each of the oral cavity insertion parts 407, and the identification information and the users may be registered in association with each other. This makes it possible to specify the user at the same time when the oral cavity insertion part 407 is detachably attached to the grip part 406.

Further, the oral cavity inspection terminal 400 may be desirably provided with a user verifying unit configured to verify that the user of the oral cavity insertion part 407 is a user registered in advance. For instance, the user verifying unit is configured to output the name of the user registered in advance by sound and to receive a user's operation of pressing a button for verification. Use of the user verifying unit as described above is advantageous in accurately acquiring bio-information of each of the users.

Further, the oral cavity inspection terminal 400 may be provided with the network connecting unit 410 configured to be connected to a network such as the Internet. The advantages of providing the network connecting unit 410 will be described in the fourth embodiment. Further, the network connecting unit 410 may be disposed on a storage stand configured to store the oral cavity inspection terminal 400 or on a charging stand configured to charge the oral cavity inspection terminal 400. Further, the the oral cavity inspection terminal (a bio-information acquiring terminal) in the embodiment may be provided with the network connecting unit 410, or may be provided with the control unit 402. This makes it possible to reduce the amount of information to be transmitted, whereby it is possible to select a more inexpensive network connecting unit.

Further, in the embodiment, the body fluid component measuring unit 401 is configured to measure the component concentration of blood in the oral cavity of the user. The body fluid component measuring unit 401 may be configured to measure the component concentration of blood in the wastes of the user, or to measure the component concentration of blood on a shaver. Using the toilet or shaving has a purpose of implementation other than the purpose for health management. Accordingly, the above configuration is advantageous in reducing cumbersomeness involved in health management of the user.

A bio-information acquiring terminal also capable of cleaning the oral cavity is desirable, because the above configuration makes it possible to measure the component concentration of blood with enhanced frequency. Further, a bio-information acquiring terminal configured to measure the component concentration of blood in the wastes is desirable as a bio-information acquiring terminal capable of measuring the concentrations of the components of many kinds such as urine, feces, and blood. A health management system provided with the bio-information acquiring terminal is also desirable because it is possible to configure the system at a low cost.

The bio-information acquiring terminal in the embodiment may be configured to record the health condition of the user, manage the health condition of the user, present the user of the health condition, and advise the user of the points to be improved on the health condition. Even a bio-information acquiring terminal which is not connected to a network is capable of recording the health condition of the user, managing the health condition of the user, presenting the user of the health condition, and advising the user of the points to be improved on the health condition.

However, it is desirable that the bio-information acquiring terminal be connected to a network as described in the embodiment. Configuring the bio-information acquiring terminal to be connected to a network makes it possible to implement the advantages as described in the fourth embodiment.

Fourth Embodiment

Figure 10:
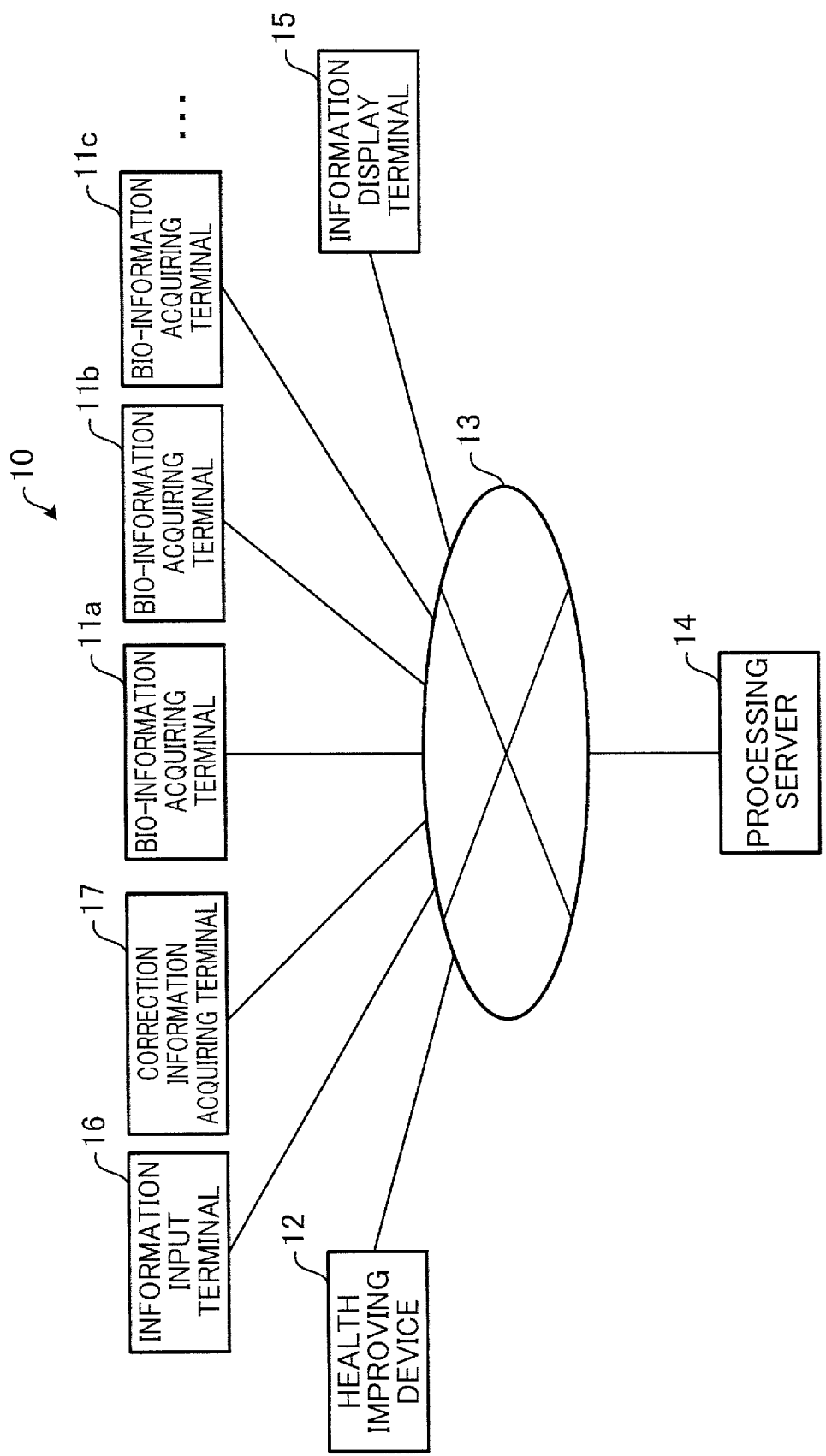
FIG. 10 is a schematic diagram illustrating an example of a health management system according to a fourth embodiment of the invention.

FIG. 10 is a schematic diagram illustrating an example of a health management system according to the fourth embodiment of the invention.

A health management system 1 according to the embodiment is such that a bio-information acquiring terminal 11a is connected to a processing server 14 via a network 13. Bio-information and personal authentication information acquired by the bio-information acquiring terminal 11a is transmitted and stored in the processing server 14 via the network 13.

The health management system 1 is provided with bio-information acquiring terminals 11a, 11b, 11c, a health improving device 12, the processing server 14, an information display terminal 15, an information input terminal 16, and a correction information acquiring terminal 17. The bio-information acquiring terminals 11a, 11b, 11c, the health improving device 12, the information display terminal 15, the information input terminal 16, and the correction information acquiring terminal 17 are communicatively connected to the processing server 14 via the network 13, respectively. The network 13 is e.g. the Internet.

The bio-information acquiring terminals 11a, 11b, 11c are configured to acquire bio-information and personal authentication information of the user, and to transmit the acquired bio-information and personal authentication information to the processing server 14. The bio-information acquiring terminal 11*a*, 11*b*, 11*c* is e.g. the bath device 300 in the first embodiment, the toilet device 200 in the second embodiment, or the oral cavity inspection terminal 400 in the third embodiment.

The information input terminal 16 is configured to receive input of bio-information and personal authentication information by the user. The information input terminal 16 is configured to transmit the received bio-information to the processing server 14 together with the personal authentication information. The information input terminal 16 is e.g. a mobile communication terminal such as a mobile phone, a tablet computer, or a personal computer.

The correction information acquiring terminal 17 is configured to acquire correction information for use in correcting bio-information acquired by the bio-information acquiring terminals 11*a*, 11*b*, 11*c*. The correction information acquiring terminal 17 is configured to transmit the acquired correction information to the processing server 14 together with the personal authentication information. The correction information acquiring terminal 17 is a device configured to measure the quantity of activity of muscle such as an activity meter or a pediometer; a device capable of estimating a wake-up time and a bedtime of the user such as a thermometer, a hygrometer, an illumination device or an illuminometer; or a position information acquiring device configured to acquire position information of the user such as a GPS (Global Positioning System).

The processing server 14 is configured to receive bio-information and personal authentication information transmitted from the bio-information acquiring terminal 11*a*, 11*b*, 11*c*, and to store the received bio-information in association with each of the users. Further, the processing server 14 is configured to generate control information for use in controlling an operation of the health improving device 12 in such a manner that the health condition of the user is improved based on the received bio-information of the user, and to transmit the generated control information to the health improving device 12.

Further, the processing server 14 is configured to receive, from the information display terminal 15, a request of acquiring a display screen for displaying bio-information, to generate a display screen for displaying bio-information of the user in accordance with the received acquisition request, and to transmit the generated display screen to the information display terminal 15.

Further, the processing server 14 is configured to receive bio-information and personal authentication information transmitted from the information input terminal 16, and to store the received bio-information in association with each of the users.

Further, the processing server 14 is configured to receive correction information and personal authentication information transmitted from the correction information acquiring terminal 17, and to correct the bio-information based on the received correction information.

The processing server 14 is e.g. the cloud server 111 or the server 121 illustrated in FIG. 1.

The health improving device 12 is configured to receive control information transmitted from the processing server 14, and to operate in accordance with the received control information. The health improving device 12 is e.g. a massage device.

The information display terminal 15 is configured to transmit a request of acquiring a display screen for displaying bio-information of the user to the processing server 14, to receive the display screen for displaying bio-information of the user from the processing server 14, and to display the received display screen. The information display terminal 15 is e.g. a mobile communication terminal such as a mobile phone, a tablet computer, or a personal computer.

The health management system 1 may not be provided with all the devices i.e. the health improving device 12, the information display terminal 15, the information input terminal 16, and the correction information acquiring terminal 17. Further, the health management system 1 may be provided with at least one of the health improving device 12, the information display terminal 15, the information input terminal 16, and the correction information acquiring terminal 17.

Figure 11:
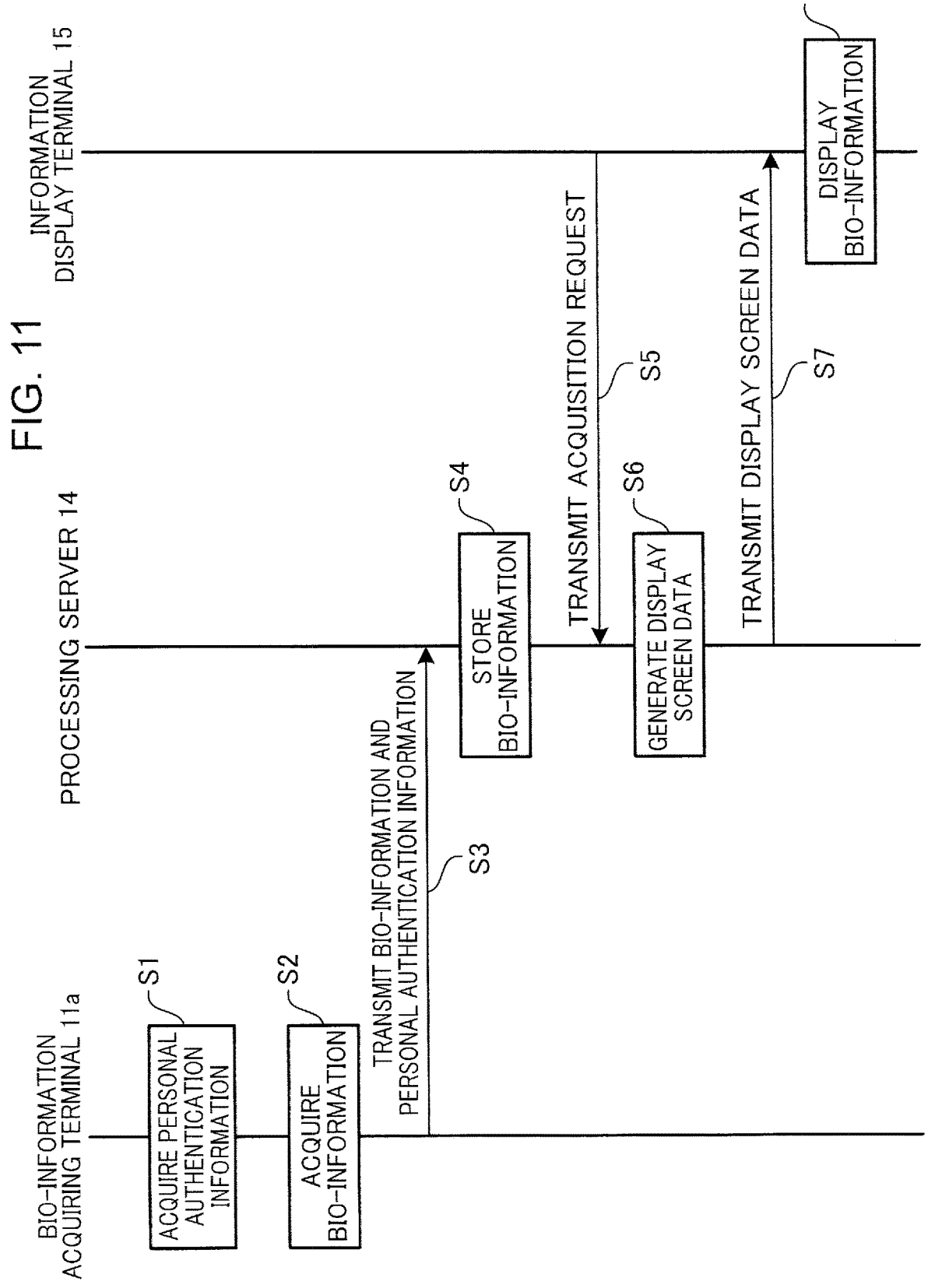
FIG. 11 is a sequence diagram illustrating a flow of processing of the health management system according to the fourth embodiment.

In the following, a flow of processing of the health management system 1 according to the fourth embodiment is described. FIG. 11 is a sequence diagram illustrating a flow of processing of the health management system according to the fourth embodiment. FIG. 11 illustrates the processing of the bio-information acquiring terminal 11*a*, the processing server 14, and the information display terminal 15. Referring to FIG. 11, description is made based on the premise that the bio-information acquiring terminal 11*a* is the bath device 300 illustrated in FIG. 3.

In Step S1, the fingerprint authentication unit 303 of the bio-information acquiring terminal 11*a* (bath device 300) authenticates the user, and acquires personal authentication information for specifying the user.

In Step S2, the bio-information measuring unit 302 measures bio-information of the user.

In Step S3, the network connecting unit 315 transmits the personal authentication information acquired by the fingerprint authentication unit 303 and the bio-information measured by the bio-information measuring unit 320 to the processing server 14, and the processing server 14 receives the personal authentication information and the bio-information transmitted from the bio-information acquiring terminal 11*a*.

In Step S4, the processing server 14 stores the received bio-information in a storing unit in association with the received personal authentication information.

In Step S5, the information display terminal 15 transmits, to the processing server 14, a request of acquiring a display screen for displaying bio-information, and the processing server 14 receives the acquisition request transmitted from the information display terminal 15. The acquisition request includes information for specifying the user.

In Step S6, the processing server 14 generates a display screen for displaying bio-information of the user in accordance with the received acquisition request. The processing server 14 reads, from the storing unit, bio-information corresponding to the information for specifying the user, which is included in the acquisition request, and generates display screen data for displaying the read bio-information.

In Step S7, the processing server 14 transmits the generated display screen data to the information display terminal 15, and the information display terminal 15 receives the display screen data transmitted from the processing server 14.

In Step S8, the information display terminal 15 displays the bio-information, based on the received display screen data.

In the health management system 1 according to the embodiment, the processing server 14 is not an essential element, but the processing server 14 connected to the network 13 may record the health condition (bio-information) of the user. This makes it possible to display the health condition (bio-information) of the user on the information display terminal 15 connected to the network 13, and to check the health condition (bio-information) of the user.

Further, it is desirable that not only the user checks his or her own health condition with use of the information display terminal 15, but also the staff in a hospital, a care facility, or a health facility checks the health condition of the user with use of the information display terminal 15. This allows for the staff in a hospital, a care facility, or a health facility to check the condition of a disease of the user.

Further, it is desirable that the family of the user checks the health condition of the user with use of the information display terminal 15. Using the information display terminal 15 connected to the network 13 allows for the family of the user living in a remote place to easily check the health condition of the user.

Further, allowing a specific company to collect bio-information of a number of users via the network 13 makes it possible to utilize the collected group of bio-information as big data.

The bio-information acquiring terminal 11a in the health management system 1 of the invention may be the toilet device 200 as described in the second embodiment. This makes it possible to manage the health condition of the user based on the components of the wastes. As described in the second embodiment, for instance, allowing the toilet device 200 to acquire the concentration of urinary protein as bio-information makes it possible to perform early detection and prognostic management of kidney diseases. Further, for instance, allowing the toilet device 200 to acquire the concentration of urinary sugar as bio-information makes it possible to perform early detection of diabetes, and allowing the toilet device 200 to acquire the amount of salt contained in urine as bio-information makes it possible to perform prognostic management of high blood pressure symptoms.

Further, the bio-information acquiring terminal 11a may be the bath device 300 as described in the first embodiment. For instance, allowing the bath device 300 to acquire an electrocardiogram as bio-information makes it possible to perform screening for arteriosclerosis. Further, allowing the bath device 300 to acquire a change in internal body temperature as bio-information makes it possible to perform early detection of the condition of a disease of the user such as a cold.

Further, the bio-information acquiring terminal 11a may be the oral cavity inspection terminal 400 as described in the third embodiment. For instance, allowing the oral cavity inspection terminal 400 to acquire a value of neutral fat, a value of LDL cholesterol, or a value of HDL cholesterol contained in blood as bio-information makes it possible to perform prognostic management of hyperlipidemia. Further, allowing the oral cavity inspection terminal 400 to acquire a blood-sugar level or a HbA1c value as bio-information makes it possible to perform prognostic management of diabetes. Further, allowing the oral cavity inspection terminal 400 to acquire a PSA (prostate-specific antibody) value as bio-information makes it possible to perform early detection of a prostatic cancer.

Further, although not described in the first to third embodiments, the bio-information acquiring terminal 11a may be an inspection terminal configured to inspect the concentration of components contained in tears. The component concentration of tears and the component concentration of blood are similar to each other. In view of the above, measuring the component concentration of tears makes it possible to estimate the aforementioned component concentrations contained in blood. Measurement precision of blood by tears is low, as compared with a configuration of directly measuring blood. However, the above measurement is advantageous in easily performing non-invasive measurement of bio-information.

Further, although not described in the first to third embodiments, the bio-information acquiring terminal 11a may be an activity meter, a body composition meter, a clinical thermometer, a blood-pressure meter, or a pulse oximeter; and bio-information which changes over time day by day, month by month, or year by year may be acquired with respect to each of the users.

As described in the first to third embodiments, the bio-information acquiring terminal 11a may be desirably a daily-use device to be used when the user uses a toilet, takes a bath, or cleans the oral cavity (brushes the teeth). This makes it possible to reduce cumbersomeness involved in health management of the user.

Further, the health management system 1 according to the embodiment may be provided with a plurality of bio-information acquiring terminals 11a, 11b, 11c, . . . to be connected via the network 13.

For instance, the bio-information acquiring terminal 11a may be a toilet device installed in the user's house, the bio-information acquiring terminal 11b may be a toilet device installed in the user's working place, and the bio-information acquiring terminal 11c may be a toilet device installed in a convenience store. In this configuration, the health management system 1 may be desirably constituted of a plurality of toilet devices installed in different places. Each of the toilet devices may transmit obtained bio-information and personal authentication information to the processing server 14.

The above configuration eliminates the need of inspecting the components of the wastes only in the toilet device of the user's house. Thus, the above configuration is advantageous in reducing cumbersomeness involved in health management. Further, the above configuration makes it possible to acquire bio-information (waste components) with enhanced frequency. This allows for more appropriate health management.

In particular, the health management system 1 may be desirably provided with a plurality of bio-information acquiring terminals installed in different places. This makes it possible to measure the discharge amount of salt for 24 hours. This is advantageous in performing appropriate management of the intake amount of salt by the user, and in encouraging the user to limit the intake amount of salt.

Further, for instance, the bio-information acquiring terminal 11a may be a blood-pressure meter installed in the user's house, the bio-information acquiring terminal 11b may be a blood-pressure meter installed in the user's working place, and the bio-information acquiring terminal 11c may be a blood-pressure meter installed in a restaurant. In this configuration, the health management system 1 may be desirably constituted of a plurality of blood-pressure meters installed in different places. Each of the blood-pressure meters may be configured to transmit obtained bio-information and personal authentication information to the processing server 14.

The above configuration eliminates the need of user's measuring the blood pressure only by the blood-pressure meter installed in the user's house. This is advantageous in reducing cumbersomeness involved in health management. Further, the above configuration makes it possible to acquire bio-information (blood pressure) with enhanced frequency. This allows for more appropriate health management.

In particular, measuring the blood pressure at a wake-up time, at a bedtime, at a time before lunch, and at a time after lunch makes it possible to grasp a daily variation of the user's blood pressure. This is advantageous in appropriately performing early detection and prognostic management of cardiovascular diseases.

Further, the health management system 1 according to the embodiment may be provided with a plurality of bio-information acquiring terminals 11a, 11b, 11c, . . . configured to acquire bio-information of different kinds, respectively.

For instance, the bio-information acquiring terminal 11a may be a blood component measuring terminal (oral cavity inspection terminal 400) configured to measure the blood components, and the bio-information acquiring terminal 11b may be a waste component measuring terminal (toilet device 200) configured to measure the components of the wastes. In this configuration, it is possible to grasp both of the blood component and the urinary component of the user, whereby it is possible to manage the health condition of the user in detail. Obtaining both of bio-information relating to the urinary component and the blood component makes it possible to calculate creatinine clearance by comparing between the urine creatinine concentration and the serum creatinine concentration. Creatinine clearance CrCl is calculated by the following formula.

$$CrCl = CrU \times VolU / CrB$$

In the above formula, CrCl denotes creatinine clearance [ml/min], CrU denotes a urine creatinine concentration [mg/dl], VolU denotes a volume [ml/min] of urine per unit time, and CrB denotes a serum creatinine concentration [ml/dl].

As described above, calculating creatinine clearance makes it possible to perform screening or prognostic management of kidney diseases.

Further, for instance, the bio-information acquiring terminal 11a may be an electrocardiogram measuring terminal (bath device 300) configured to measure an electrocardiogram, and the bio-information acquiring terminal 11b may be a blood component measuring terminal (oral cavity inspection terminal 400) configured to measure the blood components. This makes it possible to monitor both of cardiac troponin and H-FABP (human heart-derived fatty acid-binding protein) to be measured by the blood component measuring unit, and an electrocardiographic waveform to be measured by the electrocardiogram measuring terminal. This makes it possible to comprehensively perform early detection of acute myocardial infarction and chronic myocardial infarction, or to grasp the conditions of these diseases.

Further, for instance, the bio-information acquiring terminal 11a may be a tear component measuring terminal configured to measure the components contained in tears, and the bio-information acquiring terminal 11b may be a blood component measuring terminal (oral cavity inspection terminal 400) configured to measure the components contained in blood.

In the case where blood component information is not obtained from the blood component measuring unit, the processing server 14 may use tear component information obtained from the tear component measuring terminal, as substitute bio-information for the blood component information. For instance, in the case where the component concentration of glucose contained in blood is not obtained, the processing server 14 may use the component concentration of glucose contained in tears as substitute bio-information.

Further, for instance, the bio-information acquiring terminal 11a may be a waste component measuring terminal (toilet device 200) configured to measure the components of the wastes, and the bio-information acquiring terminal 11b may be a blood component measuring terminal (oral cavity inspection terminal 400) configured to measure the components contained in blood. In the case where urinary component information is not obtained from the waste component measuring terminal, the processing server 14 may use blood component information obtained from the blood component measuring terminal as substitute bio-information for the urinary component information.

Further, each of the oral cavity inspection terminal, the bath device, the toilet device, and the body composition meter used by a certain user may be provided with a network connecting unit to be connected to the network 13, and a temperature measuring unit configured to measure the temperature of each of the body parts. This allows for the processing server 14 to store the oral cavity temperature and the hand temperature measured by the oral cavity inspection terminal, the core body temperature measured by the bath device, the rectal temperature and the thigh temperature measured by the toilet device, and the sole temperature measured by the body composition meter in association with each other.

The above configuration makes it possible to accurately grasp the body temperature distribution, the condition of blood circulation in the body, the degree of sensitivity to the cold, and the like.

As described above, in the case where there is bio-information unobtainable from a bio-information acquiring terminal, bio-information obtained from another bio-information acquiring terminal may be used as substitute bio-information for the unobtainable bio-information. This is advantageous in monitoring the health condition based on sufficient bio-information.

It is needless to say that the health management system 1 provided with a plurality of bio-information acquiring terminals as described above may be provided with a bio-information acquiring terminal other than the aforementioned bio-information acquiring terminals. This allows for more appropriate health management by a larger number of bio-information acquiring terminals.

In the following, an example of a display screen to be displayed on the information display terminal 15 in the fourth embodiment is described referring to FIG. 12 to FIG. 19.

Figure 12:
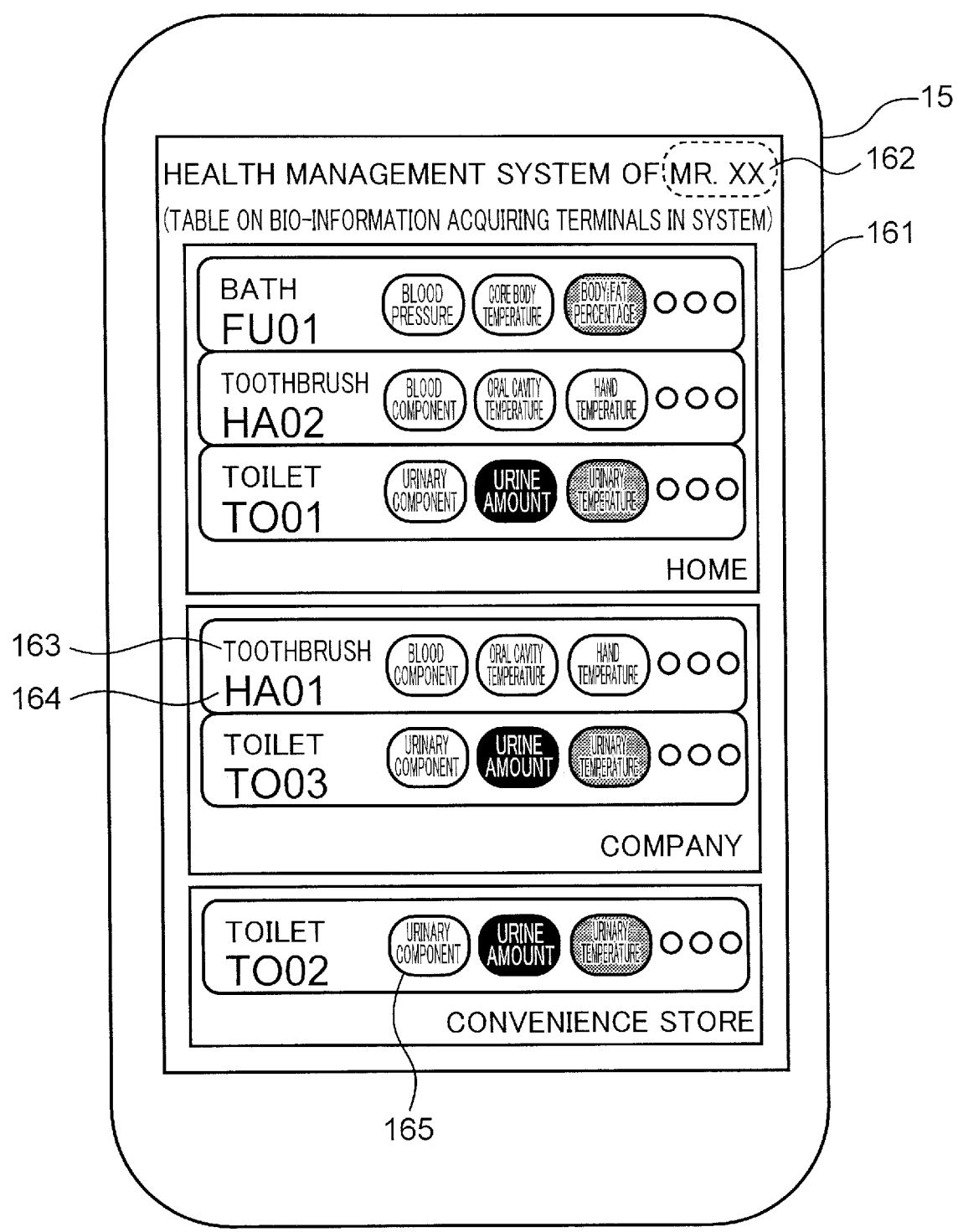
FIG. 12 is a diagram illustrating an example of a first display screen to be displayed on an information input terminal.

FIG. 12 is a diagram illustrating an example of a first display screen to be displayed on the information display terminal. The information display terminal 15 is provided with a display unit 161. The display unit 161 is configured to display a user name 162 for specifying the user, a device name 163 for specifying the bio-information acquiring terminal, a device ID 164, and bio-information 165 acquired by the bio-information acquiring terminal. The device name 163, the device ID 164, and the bio-information 165 are displayed with respect to each of the bio-information acquiring terminals, and are displayed with respect to each of the installation places of the bio-information acquiring terminals.

Referring to FIG. 12, information acquired from a plurality of bio-information acquiring terminals 11 is displayed on the information display terminal 15 with respect to each of the installation places of the bio-information acquiring terminals 11. This allows for the user to easily check the devices and bio-information used for his or her health management.

Further, the information display terminal 15 is configured to receive, via the screen illustrated in FIG. 12, an input relating to information disclosure restriction as to whether each of the bio-information 165 acquired by the bio-information acquiring terminals 11 is to be provided to the service provider 120. The input relating to information disclosure restriction received by the bio-information acquiring terminals 11 is displayed on the information display terminal 15 in different colors. For instance, in the case where providing bio-information to the service provider 120 is permitted, the bio-information 165 is displayed in white. In the case where a measurement result is kept without providing bio-information to the service provider 120, the bio-information 165 is displayed in gray. In the case where bio-information is not provided to the service provider 120, and a measurement result is not kept, the bio-information 165 is displayed in black. In this way, the bio-information 165 is displayed in different colors in accordance with the information disclosure restriction.

Thus, the user is allowed to check the bio-information 165 acquired from the bio-information acquiring terminal of his/her own, and from each of the other bio-information acquiring terminals 11 in the form of a table. Further, it is possible to easily check and manage whether the bio-information 165 is to be provided to the service provider 120, or whether a measurement result is to be kept. Alternatively, it is possible to display, on the information display terminal 15, a service providable out of the bio-information 165 currently provided to the service provider 120.

Figure 13:
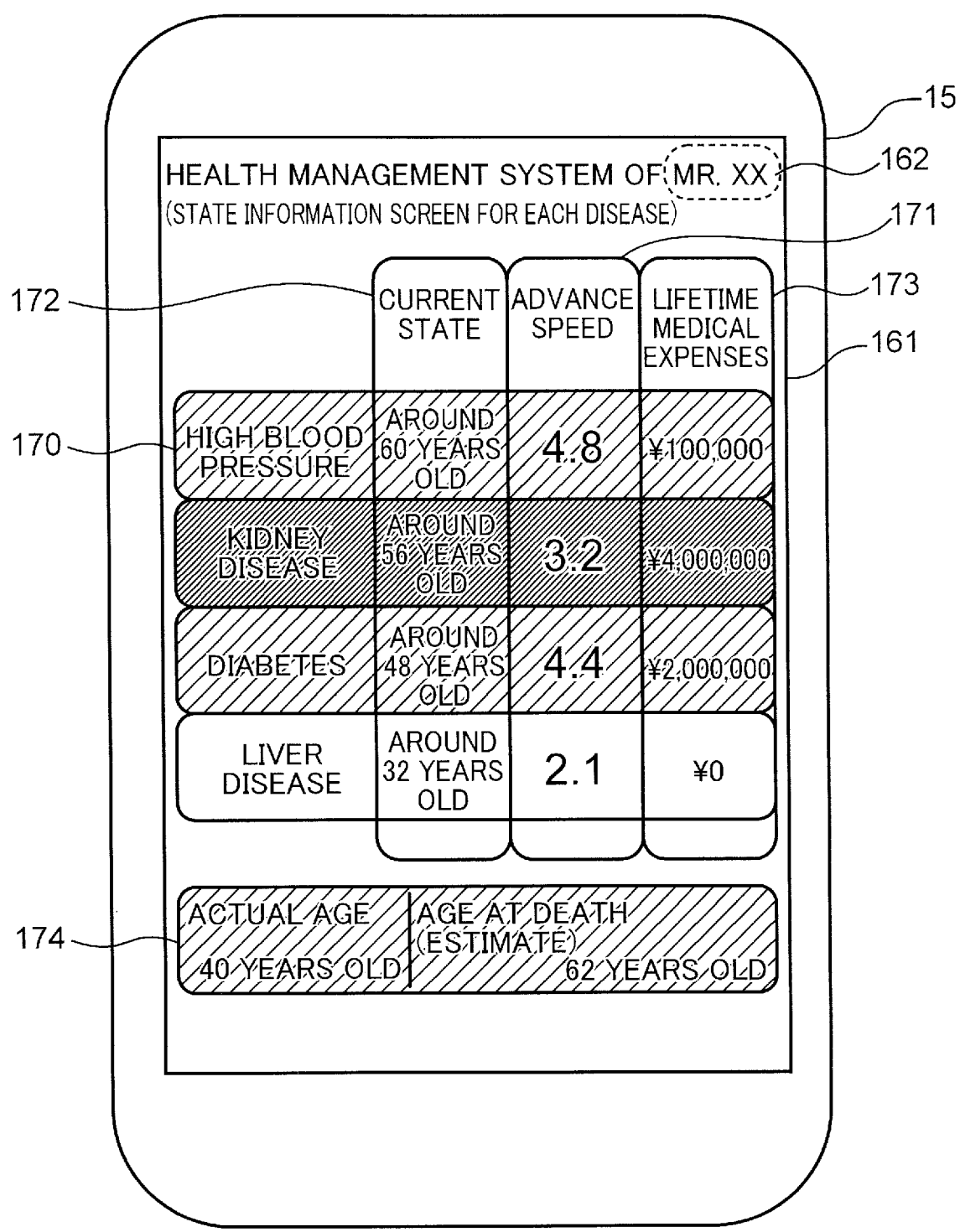
FIG. 13 is a diagram illustrating an example of a second display screen to be displayed on the information input terminal.

FIG. 13 is a diagram illustrating an example of a second display screen to be displayed on the information display terminal. The information display terminal 15 is provided with the display unit 161.

Referring to FIG. 13, the information display terminal 15 is configured such that a predicted disease or diseases are displayed on a dedicated page of the user, based on the bio-information acquired from a plurality of bio-information acquiring terminals 11. In Step S6 of FIG. 11, the processing server 14 of the service provider 120 analyzes the information to be presented to the user based on the bio-information acquired in Step S2, and generates display data illustrated in FIG. 13.

Referring to FIG. 13, there are displayed disease names 170 indicating the names of predicted diseases. Further, speeds of advance 171 of the predicted diseases are displayed in the form of scores. The speed of advance 171 in FIG. 13 indicates a speed of deterioration of a condition for the past one month, and is indicated by the point out of 5 points. Further, there are displayed ages 172, each of which corresponds to the virtual age of the user suffering from the predicted disease. This allows for the user to grasp the current condition, and to compare with the actual age. The age corresponding to the condition of the predicted disease may be the information obtained by the processing server 14 by accumulating a large amount of information acquired from the information display terminals 15 of the other users in the past, and by calculating the accumulated large amount of information.

Further, there are calculated and displayed lifetime medical expenses 173 which are expected to cost in the future, based on the conditions of the predicted diseases. This makes it possible to enhance the user's motivation for health improvement. Further, the display unit 161 is configured to display a life expectancy result 174 calculated based on the condition of the predicted disease. Further, as the degree of severity of the disease increases, the disease is displayed in a dark background color.

Figure 14:
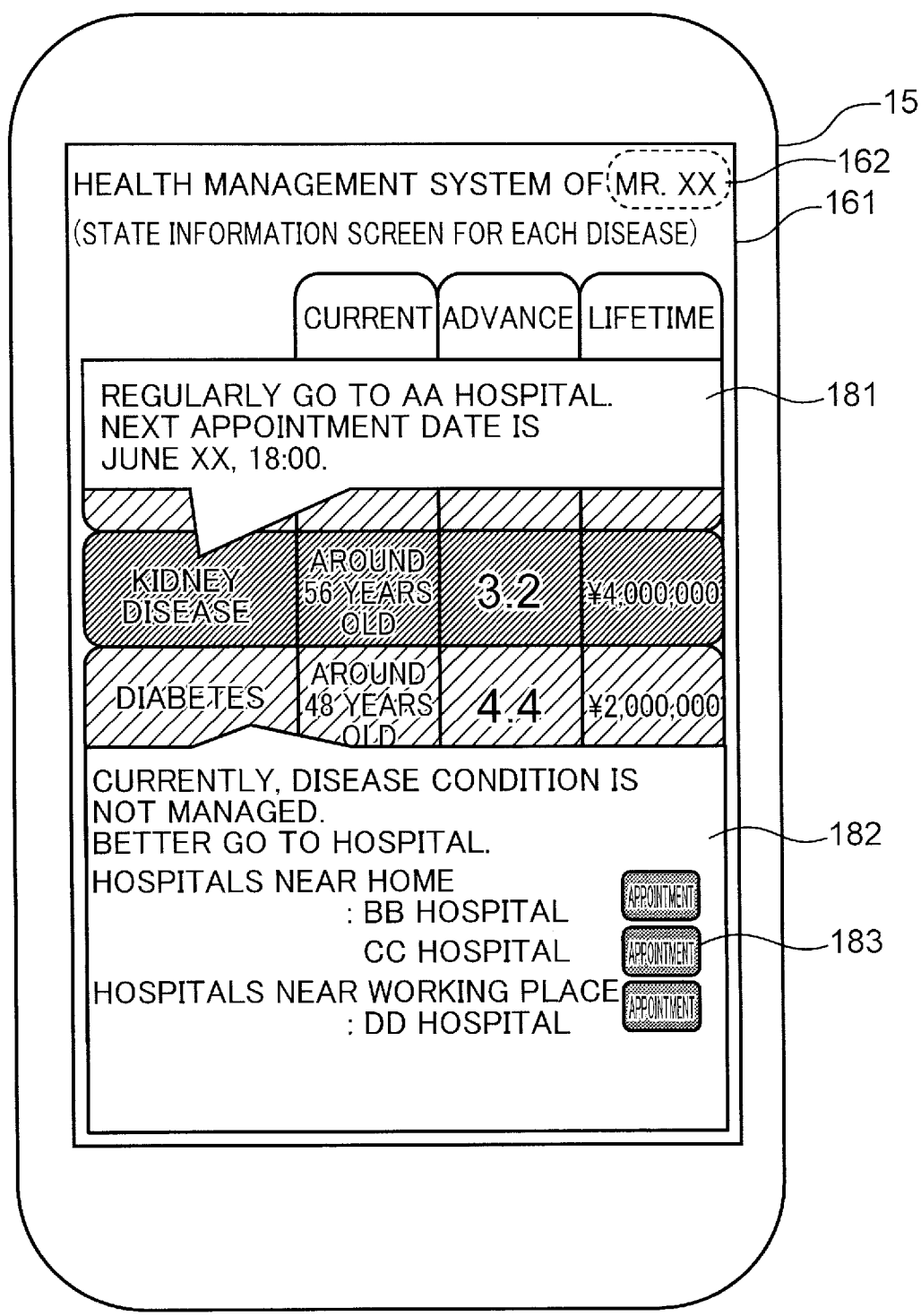
FIG. 14 is a diagram illustrating an example of a third display screen to be displayed on the information input terminal.

FIG. 14 is a diagram illustrating an example of a third display screen to be displayed on the information display terminal. The information display terminal 15 is provided with the display unit 161.

Referring to FIG. 14, the information display terminal 15 is configured to display hospital attending information 181 relating to a schedule on attending to hospital and hospital information 182 relating to the hospitals nearby, which are created based on bio-information acquired from a plurality of bio-information acquiring terminals 11, and based on a user's history on attending to hospital, which is managed by the service provider 120. In FIG. 14, the hospital attending information 181 and the hospital information 182 are displayed in an overlapped state with the information relating to each of the diseases displayed in FIG. 13.

The method for acquiring the hospital attending information 181 and the hospital information 182 by the service provider 120 is not limited. The hospital attending information 181 and the hospital information 182 may be notified to the service provider 120 by allowing the user to input the hospital attending information 181 and the hospital information 182 on the information display terminal 15. Alternatively, the service provider 120 may be configured to automatically create the hospital attending information 181 and the hospital information 182, with use of position information acquired from a GPS (not illustrated) built in the information display terminal 15. Further alternatively, the processing server 14 of the service provider 120 may be configured to create the hospital attending information 181 and the hospital information 182 by linking to a server device installed in each of the hospitals. In FIG. 14, there is displayed the hospital attending information 181 including the information relating to the hospital to which the user currently attends, and appointment information relating to attending to hospital next time.

Further, referring to FIG. 14, there is displayed the hospital information 182 relating to the hospitals nearby, based on the user's history on attending to hospital. The hospital information 182 is displayed when the user does not attend to hospital for a predetermined period or longer. Further, in the case where attending to hospital is not managed with respect to a selected disease, the hospital information 182 may include a message encouraging the user to take first medical examination. Further, the processing server 14 may be configured to search the hospitals nearby, based on the user's residential address which is registered in advance, or based on position information of the user acquired by GPS.

As described above, according to the health management system of the embodiment, it is possible to display the hospital information 182 relating to the hospitals nearby. Thus, the user is encouraged to attend to hospital. This is advantageous in encouraging the service provider 120 such as the hospitals and the companies to advertise for themselves.

Further, the display unit 161 is configured to display appointment buttons 183 corresponding to the displayed hospital information 182. The user can make appointment for medical examination in a hospital nearby by pressing (clicking or touching) the appointment button 183 corresponding to the displayed hospital information 182.

Figure 15:
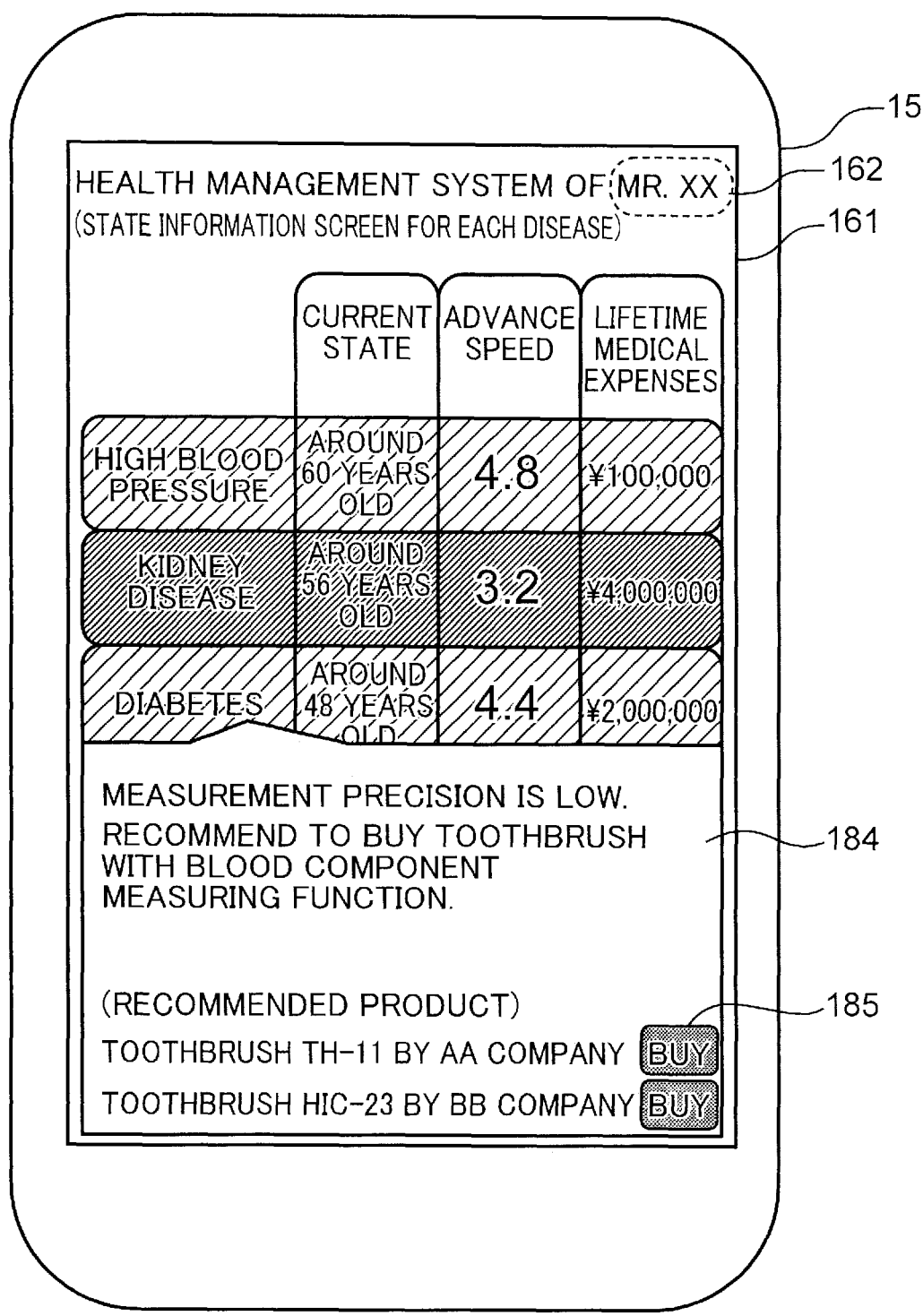
FIG. 15 is a diagram illustrating an example of a fourth display screen to be displayed on the information input terminal.

FIG. 15 is a diagram illustrating an example of a fourth display screen to be displayed on the information display terminal. The information display terminal 15 is provided with the display unit 161.

Referring to FIG. 15, the information display terminal 15 is configured to display advertisement information 184 selected based on bio-information acquired from a plurality of bio-information acquiring terminals 11, and based on advertisement information managed by the service provider 120. In FIG. 15, the advertisement information 184 is displayed in an overlapped state with the information relating to each of the diseases displayed in FIG. 13. Referring to FIG. 15, the processing server 14 is configured to acquire information relating to measurement precision of the bio-information acquiring terminals 11, to select the advertisement information 184 of providing the corresponding bio-information acquiring terminal 11 from the acquired information, and to display the selected advertisement information 184.

Further, the display unit 161 is configured to display buy buttons 185 corresponding to the displayed advertisement information. The user can purchase an advertised product by pressing (clicking or touching) the buy button 185 corresponding to the displayed advertisement information 184 with use of the information display terminal 15. In this way, in the case where measurement precision of bio-information is low, the health management system suggests the user to buy a bio-information acquiring terminal having a larger number of measurement functions in order to enhance the measurement precision.

Figure 16:
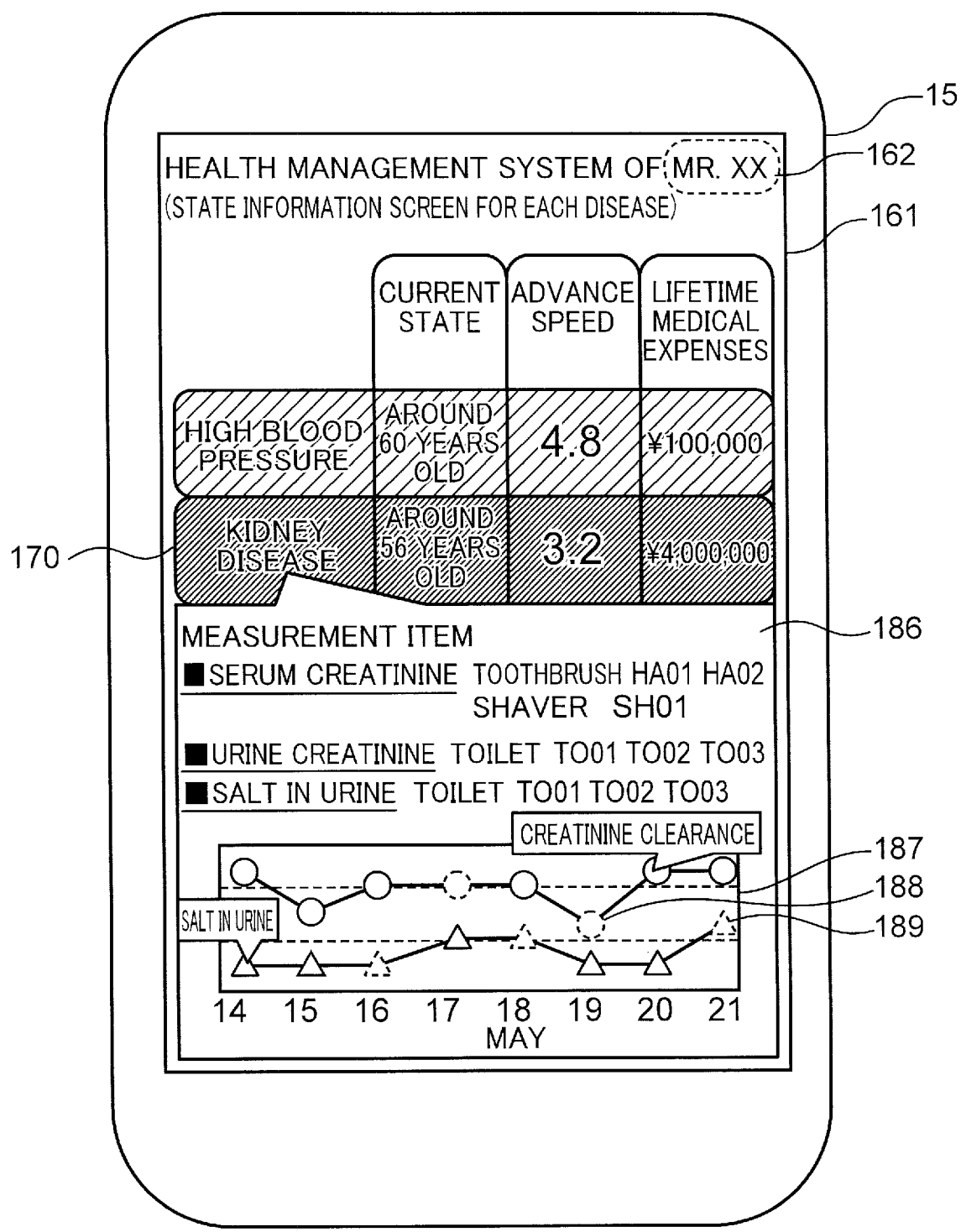
FIG. 16 is a diagram illustrating an example of a fifth display screen to be displayed on the information input terminal.

FIG. 16 is a diagram illustrating an example of a fifth display screen to be displayed on the information display terminal. The information display terminal 15 is provided with the display unit 161.

Referring to FIG. 16, the information display terminal 15 is configured to display detail information 186 relating to the diseases of the user, which are predicted based on bio-information acquired from a plurality of bio-information acquiring terminals 11. In FIG. 16, the detail information 186 is displayed in an overlapped state with the information relating to each of the diseases displayed in FIG. 13. In FIG. 16, in response to user's pressing (clicking or touching) the displayed disease name 170, the detail information 186 is displayed. The detail information 186 includes details of bio-information acquired from each of the bio-information acquiring terminals 11, based on which the corresponding disease information is created. This allows for the user to check, from which one of the bio-information acquiring terminals 11, the bio-information is acquired.

Further, in the detail information 186 in FIG. 16, the bio-information acquired from the bio-information acquiring terminals 11 is displayed in a graph with respect to each of the acquisition dates. Referring to a graph 187 displayed in FIG. 16, data 188 on a day when data which is deviated from average acquisition data of the user by a predetermined value or more is displayed in a display mode different from the ordinary display mode representing a reference value. Further, in the case where bio-information is input by the user, without being acquired from the bio-information acquiring terminal 11, data 189 on a day when the user has input the data is displayed in a display mode different from the ordinary display mode representing a reference value.

Figure 17:
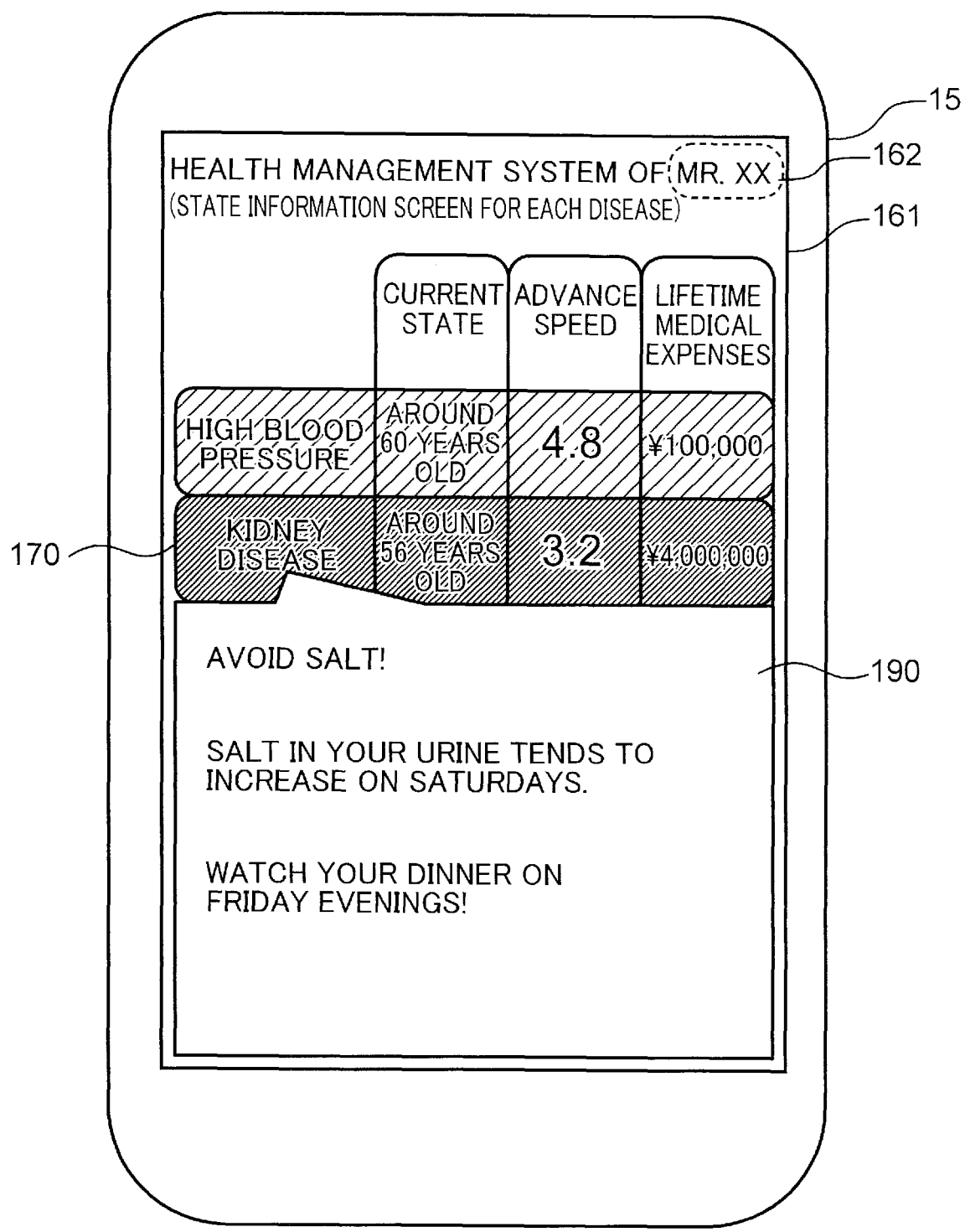
FIG. 17 is a diagram illustrating an example of a sixth display screen to be displayed on the information input terminal.

FIG. 17 is a diagram illustrating an example of a sixth display screen to be displayed on the information display terminal. The information display terminal 15 is provided with the display unit 161.

Referring to FIG. 17, the information display terminal 15 is configured to display suggestion information 190 to be presented to the user, based on bio-information acquired from a plurality of bio-information acquiring terminals 11. In FIG. 17, the suggestion information 190 is displayed in an overlapped state with the information relating to each of the diseases displayed in FIG. 13. In FIG. 17, in response to user's pressing (clicking or touching) the displayed disease name 170, there is displayed the suggestion information 190 indicating a countermeasure method to be implemented with respect to the disease corresponding to the disease name 170. As illustrated in FIG. 17, for instance, the suggestion information 190 includes a variety of information leading to health improvement of the user, which are creatable based on acquired bio-information.

The processing server 14 may be configured to monitor the contents of meals of the user, and to present the suggestion information 190 including meal menus which may worsen the current disease of the user, out of the meal menus of the user. Further, regarding the meal menus which may worsen the current disease of the user, it is possible to display how much the lifetime medical expenses will increase, or how many years the life expectancy will be shortened by the meal menus. Furthermore, the display unit 161 may be configured to display the suggestion information 190 including meal menus which may improve the current disease of the user.

Figure 18:
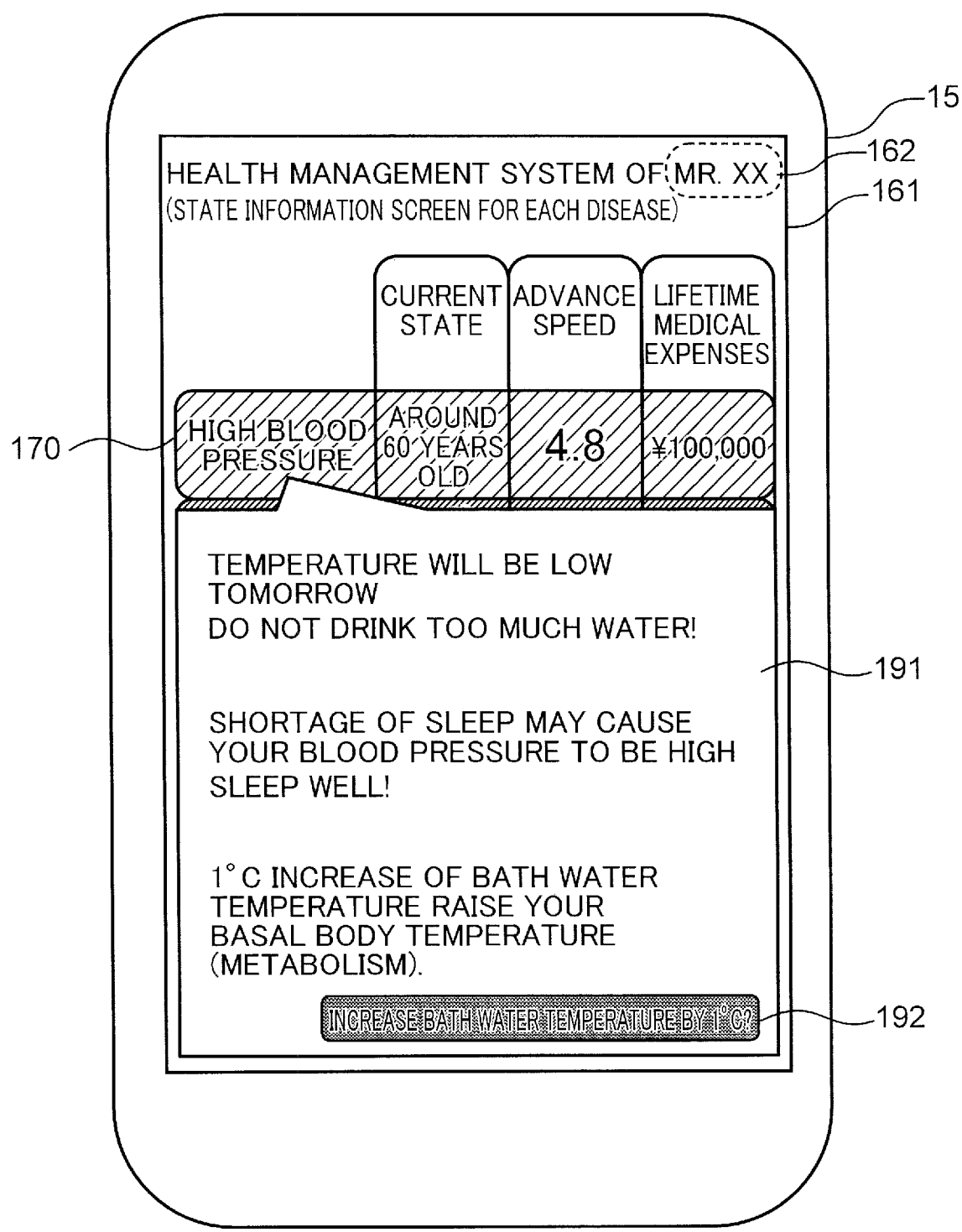
FIG. 18 is a diagram illustrating an example of a seventh display screen to be displayed on the information input terminal.

FIG. 18 is a diagram illustrating an example of a seventh display screen to be displayed on the information display terminal. The information display terminal 15 is provided with the display unit 161.

Referring to FIG. 18, as well as FIG. 17, the information display terminal 15 is configured to display suggestion information 191 to be presented to the user, based on bio-information acquired from a plurality of bio-information acquiring terminals 11. In FIG. 18, in response to user's pressing (clicking or touching) the displayed disease name 170, there is displayed the suggestion information 191 indicating countermeasure methods to be implemented with respect to the disease corresponding to the disease name 170.

Referring to FIG. 18, a control button 192 is displayed for controlling a device based on the displayed suggestion information 191. The user can control each of the devices (including the other bio-information acquiring terminals 11) connected to the processing server 14 by pressing (clicking or touching) the control button 192. For instance, in FIG. 18, there is displayed the control button 192 indicating "INCREASE BATH WATER TEMPERATURE BY 1° C.?". In response to user's pressing (clicking or touching) the control button 192, the bath device 300 (the water temperature in the bathtub 330) connected to the processing server 14 is controlled.

Further, the suggestion information 191 may be created based on bio-information acquired from the bio-information acquiring terminal 11, and based on a variety of information acquired from the other devices (including the other bio-information acquiring terminals 11). For instance, as illustrated in FIG. 18, in the case where the disease name 170 is a high blood pressure, the suggestion information 191 encouraging the user to make improvement on shortage of sleep, which is one of the causes of the disease, is created and displayed based on information relating to the sleeping hours acquired from other device. In addition to the above, information relating to the outdoor temperature or weather may be included in the variety of information acquired from the other devices (including the other bio-information acquiring terminals 11).

Figure 19:
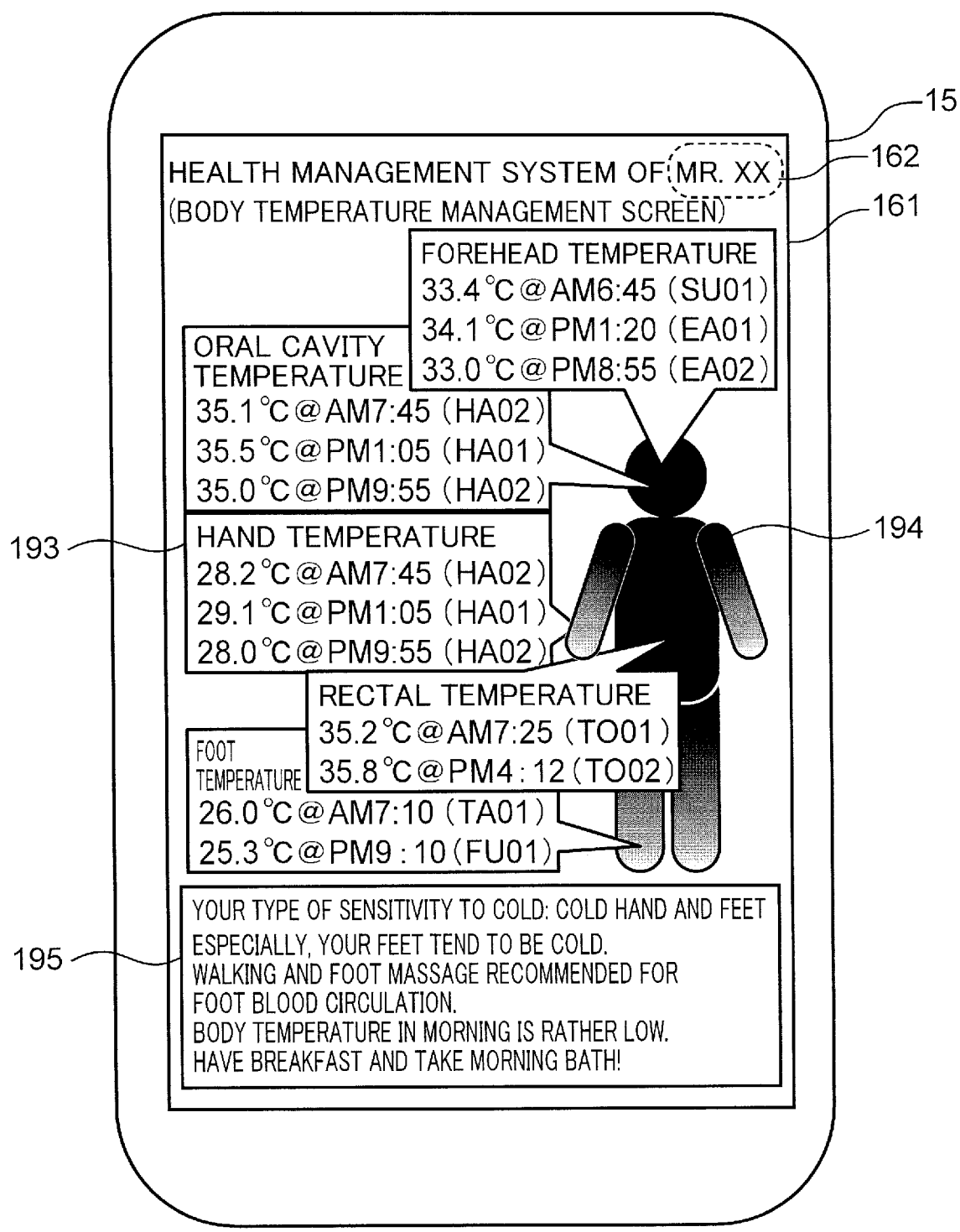
FIG. 19 is a diagram illustrating an example of an eighth display screen to be displayed on the information input terminal.

FIG. 19 is a diagram illustrating an example of an eighth display screen to be displayed on the information display terminal. The information display terminal is provided with the display unit 161.

Referring to FIG. 19, the information display terminal 15 is configured to display bio-information 193 acquired from a plurality of bio-information acquiring terminals 11 with respect to each of the body parts of the user. In FIG. 19, there are displayed bio-information representing the temperature, the date and time when the bio-information has been acquired, and information for specifying the bio-information acquiring terminal 11 that has acquired the bio-information with respect to each of the body parts. For instance, a forehead temperature, an oral cavity temperature, a hand temperature, a rectal temperature, and a foot temperature are acquired from a plurality of bio-information acquiring terminals 11, and are displayed together with the acquired date and time and the bio-information acquiring terminals 11 that have acquired the bio-information.

In FIG. 19, "SU01" indicates a sleep meter disposed on the bedside, "EA01" indicates an air-conditioner installed in the user's working place, "EA02" indicates an air-conditioner installed in the user's house, "HA01" indicates a toothbrush (oral cavity inspection terminal) disposed in the user's working place, "HA02" indicates a toothbrush (oral cavity inspection terminal) disposed in the user's house, "TO01" indicates a toilet device installed in the user's working place, "TO02" indicates a toilet device installed in the user's house, "TA01" indicates a body composition meter disposed in the user's house, and "FU01" indicates a bath device installed in the user's house.

Further, the display unit 161 may be configured to display a human image 194 representing a human body. The display unit 161 is configured to display a temperature distribution of the body temperature of the user by changing the color or the gradation of each of the body parts on the human image 194 in accordance with the temperature measured with respect to each of the body parts. For instance, the human image 194 is displayed such that a body part having a low body temperature is displayed in a light color, and a body part having a high body temperature is displayed in a dark color.

Further, there is displayed a diagnosis result 195 indicating the health condition (e.g. the degree of sensitivity to the cold) relating to the body temperature, based on the plurality of bio-information. Further, the diagnosis result 195 includes an improvement advice on the health condition. The improvement advice may be created based on bio-information acquired from the bio-information acquiring terminal 11, and based on all the information acquired from the other devices (including the other bio-information acquiring terminals 11). For instance, an improvement advice "do not sit up late at night on Saturdays and Sundays!" may be created, based on information relating to temperatures or days of the week, and based on information relating to the sleeping hours calculated from the hours when the indoor lighting is turned on.

Further, the health management system 1 according to the embodiment may be provided with the correction information acquiring terminal 17. The processing server 14 is capable of accurately monitoring the health condition by correcting bio-information to be obtained from the bio-information acquiring terminal 11a, with use of correction information to be obtained from the correction information acquiring terminal 17.

For instance, let it be assumed that the bio-information acquiring terminal 11a is a blood component measuring unit, the bio-information acquiring terminal 11b is a waste component measuring terminal, and the processing server 14 monitors creatinine clearance. In this case, the serum creatinine concentration depends on the quantity of activity of muscle. In view of the above, the correction information acquiring terminal 17 is constituted of e.g. an activity meter or a pedometer, and is configured to measure the quantity of activity of muscle as correction information. The correction information to be obtained from the correction information acquiring terminal 17 may be used as correction information in calculating the health condition (the condition of the kidneys) from creatinine clearance.

Further, the correction information acquiring terminal 17 may be desirably connected to the processing server 14 via the network 13. The correction information acquiring terminal 17 may be configured to acquire personal authentication information together with correction information, and to transmit the acquired correction information and personal authentication information to the processing server 14. This makes it possible to easily perform health management with use of correction information.

Further, the correction information acquiring terminal 17 may be a thermometer or a hygrometer, or may be configured to acquire a room temperature, an outdoor temperature, or a humidity as correction information. This makes it possible to correct an influence on bio-information due to a room temperature, an outdoor temperature, or a humidity. This allows for more appropriate health management.

Further, the correction information acquiring terminal 17 may be an illumination device disposed in a bedroom, and may be configured to estimate a wake-up time and a bedtime of the user from a history of use of the illumination device and to acquire the estimated wake-up time and bedtime as correction information. This makes it possible to correct an influence on bio-information due to a bedtime and a wake-up time. This allows for more appropriate health management.

For instance, in the case where a body fat percentage is measured by an impedance method, the body fat percentage is calculated to be high, as the time elapses from the wake-up time. The processing server 14 is capable of correcting the body fat percentage, based on a bedtime and a wake-up time. Further, in measuring and comparing the temperatures of different body parts (such as the oral cavity, the hands, the soles, the core body, or the thighs) with use of a plurality of measuring devices, the processing server 14 is capable of correcting bio-information, taking into consideration of an influence of a temperature variation in a day, based on the time when the temperature of each of the body parts is measured, the bedtime, and the wake-up time.

Further, the correction information acquiring terminal 17 may be an air-conditioner provided with an illuminator installed in a bedroom, and may be configured to estimate a bedtime and a wake-up time of the user from the information relating to the brightness of the bedroom measured by the illuminometer, and to acquire the estimated wake-up time and bedtime as correction information. This makes it possible to correct an influence on bio-information due to a bedtime and a wake-up time. This allows for more appropriate health management.

Further, the correction information acquiring terminal 17 may be a device provided with a position information acquiring unit such as a GPS carried by the user all the time, and may be configured to acquire position information such as a moving area or a moving distance of the user on the daily basis as correction information. This makes it possible to correct an influence on bio-information due to the amount of exercise of the user, the activity environment (such as the temperature, the humidity, or existence of harmful substances in the air in a place where the user resides), or the amount of UV rays irradiated on the user. This allows for more appropriate health management.

Further, the health management system 1 according to the embodiment may be desirably provided with the information input terminal 16 connected to the processing server 14 via the network 13.

For instance, the user may input information relating to reliability of stored bio-information with use of the information input terminal 16. Specifically, the information input terminal 16 is configured to receive user's input of information relating to reliability of stored bio-information. This allows for more appropriate health management.

Further, the other terminals such as the bio-information acquiring terminal 11a, the correction information acquiring terminal 17, and the information display terminal 15 may be provided with the function of the information input terminal 16.

For instance, the bio-information acquiring terminal 11a may be provided with a function capable of inputting information. As a function capable of inputting information, there is used a touch panel, a keyboard, a mouse, or a display configured to display input information thereon.

Let it be assumed that the bio-information acquiring terminal 11a is a blood component measuring unit, the bio-information acquiring terminal 11b is a waste component measuring unit, and the processing server 14 is configured to monitor creatinine clearance. Conventionally, in measuring creatinine clearance, the user has to limit the intake amount of protein in a meal of the day before the measurement. Contrary to the above, in the embodiment, the user may input the intake amount of protein in a meal of the day before the measurement, with use of the information input terminal 16. The processing server 14 is capable of eliminating creatinine clearance data (eliminating the data from health management) on a day when the intake amount of protein is large. This makes it possible to perform more appropriate management of the function of the kidneys of the user.

Further, the processing server 14 may use creatinine clearance data on a day when the intake amount of protein is large as reference information in determining a weight with respect to each data, without eliminating the creatinine clearance data.

As described above, it is desirable to omit error data (noise) of low reliability, with use of the information input from the information input terminal 16. This allows for more appropriate health management.

Further, in the above configuration, the user does not have to limit the meal for health management, and is advantageous in reducing cumbersomeness involved in health management.

Further, in the case where the bio-information acquiring terminal 11a is a blood component measuring unit, the bio-information acquiring terminal 11b is a waste component measuring terminal, and the processing server 14 is configured to monitor creatinine clearance, the information input terminal 16 may be desirably configured to receive user's input of the amount of exercise in a day. This allows for the processing server 14 to correct creatinine clearance data or to apply a weight to data, taking into consideration of an influence of a change in urine creatinine concentration due to a change in the amount of exercise. This makes it possible to perform more appropriate prognostic management of kidney diseases.

In particular, the processing server 14 is capable of omitting creatinine clearance data on a day when the amount of exercise is large, as data of low reliability.

Further, also in the case where the bio-information acquiring terminal 11a is a waste component measuring terminal, the waste component measuring terminal is configured to measure the urine concentration together with the amount of salt in the wastes, and the processing server 14 is configured to estimate the amount of salt in the wastes for 24 hours by a one-time urine component measurement, the information input terminal 16 may be desirably configured to receive user's input of the amount of exercise in a day. This makes it possible to perform more appropriate prognostic management of high blood pressure symptoms.

Further, for instance, the information input terminal 16 may be configured to receive user's selection of blood test information on a day when the reliability is low, out of the blood test information measured by the blood component measuring terminal, and the processing server 14 may be configured to erase the blood test information selected by the information input terminal 16.

For instance, the user may set the health management such that blood test information of low reliability such as blood test information on a day when the user drank alcohol is omitted from the health management. This allows for more appropriate health management by blood component analysis.

Further, in the other cases, the information input terminal 16 may be configured to receive user's selection of bio-information of low reliability, out of the bio-information acquired from the bio-information acquiring terminal, and the processing server 14 may be configured to erase the bio-information selected by the information input terminal 16. This allows for the user to omit bio-information of low reliability by his or her own will. This makes it possible to omit bio-information of low reliability, even in the case where the health management system 1 is not provided with the correction information acquiring terminal 17. This allows for more appropriate health management.

Further, one of a plurality of bio-information acquiring terminals may be configured to automatically detect that the user has drunk alcohol. This makes it possible to eliminate the user's operation, and to accurately detect that the user has drunk alcohol, whereby it is possible to perform more appropriate health management.

For instance, the waste component measuring terminal may be configured to measure a urine-alcohol concentration, the processing server may be configured to erase bio-information such as an electrocardiogram or a heart rate acquired from the other bio-information acquiring terminal (e.g. a bath device) on a day when the urine-alcohol concentration measured by the waste component measuring terminal exceeds a predetermined threshold value, in view of a possibility that the bio-information is affected by drinking alcohol. This makes it possible to omit bio-information of low reliability.

Further, in the case where the user does daily affairs such as using a toilet or taking a bath with use of a toilet device or a bath device on the outside of the health management system 1, the information input terminal 16 may be configured to receive input on a history of doing the daily affairs. This allows for more appropriate health management.

For instance, in the case where the amount of salt contained in the user's urine is measured, and health management is performed based on the discharge amount of salt of the user, it is possible to know an elapsed time after the user has urinated last time. This allows for more appropriate health management. In view of the above, in the case where the user has urinated with use of a toilet device (life terminal) which is not connected to the processing server 14, the information input terminal 16 may be configured to receive input of timestamp information when the user has urinated with use of the toilet device (life terminal) which is not connected to the processing server 14, and to transmit the received timestamp information to the processing server 14. This allows for more appropriate health management.

Further, in the case where the user takes a bath with use of a bath device which is not connected to the processing server 14, the information input terminal 16 may be configured to receive input of information such as timestamp information relating to the point of time when the user takes a bath with use of the bath device which is not connected to the processing server 14, temperature information relating to the hot water temperature at the time when the user takes a bath, and time period information relating to the period of time when the user is taking a bath, and may transmit the received timestamp information, temperature information, and time period information to the processing server 14. This allows for more appropriate health management, taking into consideration of an influence of a change in component concentration in urine or blood by taking a bath, even in the case where the user takes a bath with use of a bath device other than the bath device managed by the health management system 1.

Further, in the case where the user uses a bio-information acquiring terminal such as a blood pressure meter or a waste component measuring terminal (toilet device) which is installed on the outside of the health management system 1 and which is not connected to the processing server 14, the information input terminal 16 may be configured to receive input of acquired bio-information or acquisition timestamp information representing the point of time when the bio-information has been acquired, and to transmit the received bio-information or acquisition timestamp information to the processing server 14. This allows for more appropriate health management.

The information input terminal 16 may be configured to receive e.g. a measurement result by a blood pressure meter which is not connected to the network 13, or input of a blood test result in a medical institution which is not configured to automatically provide information to the health management system 1. This makes it possible to acquire bio-information with enhanced frequency, and to perform more appropriate health management.

Further, the health management system 1 may be provided with the health improving device 12 configured to improve the health condition of the user, based on user's bio-information obtained from the bio-information acquiring terminal 11a, 11b, 11c, the correction information acquiring terminal 17, or the information input terminal 16. This makes it possible to improve the health condition of the user.

For instance, in the case where the health management system 1 is configured to manage the progress of a condition of a disease such as a lifestyle disease by using a toilet device (waste component measuring terminal), an oral cavity inspection terminal, or a bath device as a bio-information acquiring terminal, the health improving device 12 may be configured to present meal menus which are effective in improving the health condition with respect to each of the users. Specifically, the processing server 14 is configured to store bio-information, and information relating to meal menus in accordance with the bio-information in association with each other, to read the meal menu information corresponding to the bio-information acquired from the bio-information acquiring terminal, and to transmit the read meal menu information to the health improving device 12. The health improving device 12 is configured to receive the meal menu information transmitted from the processing server 14, and to display the received meal menu information. This makes it possible to improve the health condition of the user.

Further, the health improving device 12 may be configured to present meal menus, taking into consideration of both of information relating to foodstuff stored in the house or sale information in food stores nearby, and bio-information (health condition) of the user. This is advantageous in improving the health condition of the user.

Further, the health management system 1 may be configured to apply foodstuff necessary for presented meal menus to a delivery service with the user's permission. This allows for the user to reduce cumbersomeness in improving the health condition. Further, in providing the above service, it is possible to record both of the meal menus taken by the user, and the bio-information. This makes it possible to suggest an optimum meal menu with respect to each of the users. This is advantageous in providing a health management system with a prospect of improving the health condition of the user.

Further, as also described in the first embodiment, in the case where the bio-information acquiring terminal 11a is a bath device, measuring bio-information such as the heat capacity, the thermal conductivity, the skin surface temperature, the internal body temperature, and the sound velocity of each of the body parts makes it possible to grasp the muscular fatigue or the blood flow rate of each of the body parts of the user. Thus, the information relating to the muscular fatigue or the blood flow rate of the user is transmitted to the health improving device 12 such as a massage chair via the network 13 after the user takes a bath, and the health improving device 12 is capable of performing a massage operation suitable for the degree of fatigue. This is advantageous in efficiently relieving fatigue of the user.

Further, the information input terminal 16 may be configured to receive input of information relating to the weather, the humidity, or the room temperature together with the information relating to meal menus taken by the user, and the bio-information. This allows for the health improving device 12 to present meal menus suitable for the weather or humidity of each day of the week with respect to each of the users. This is advantageous in providing a health management system with a prospect of improving the health condition of the user.

Further, allowing the processing server 14 to record the wake-up time and the bedtime of the user acquired as described above in association with the information relating to meal menus taken by the user and the bio-information allows for the health improving device 12 to provide an optimum improvement measure, taking into consideration of the wake-up time and the bedtime of the user.

Further, the health improving device 12 may be configured to adjust the house environment (such as the room temperature, the humidity, the brightness of the illumination device, or the luminescent color of the illumination device) in accordance with the health condition of the user. This is advantageous in improving the health condition of the user.

Further, the health improving device 12 may be a bath device. For instance, in the case where the bio-information acquiring terminal is an activity meter, and the health improving device 12 is a bath device, the bath device is configured to adjust the temperature of hot water, based on the amount of activity in a day, which is measured by the activity meter. This is advantageous in effectively relieving fatigue of the user.

Further, the health improving device 12 may be desirably configured to adjust the temperature of hot water, based on a period of time from the mealtime before taking a bath or from the current point of time to the bedtime. This is advantageous in effectively relieving fatigue of the user. It is possible to estimate the mealtime before taking a bath, from a use state of cooking household appliances. Further, it is possible to predict the bedtime, based on the daily bedtimes which are stored in advance. However, the information input terminal 16 may be desirably configured to receive user's input of a mealtime or a bedtime. This makes it possible for the user to take a bath with an optimum hot water temperature, particularly in a case that the bedtime is different from the ordinary bedtime. This is advantageous in effectively relieving fatigue of the user.

Further, in the health management system 1, the processing server 14 may be provided in any one of the bio-information acquiring terminals 11a, 11b, 11c, the information display terminal 15, the information input terminal 16, and the correction information acquiring terminal 17 connected to the network 13 in the health management system 1.

Further, the processing server 14 may be desirably installed in the user's house. This makes it possible to continuously utilize the health management system 1 constituted of the bio-information acquiring terminals in the house and the processing server in the house via a network in the house, even in the case where the health management system 1 is cut off from the network on the outside of the house by a large-scale disaster or the like.

Further, the bio-information acquiring terminals 11a, 11b, 11c, the information display terminal 15, the information input terminal 16, and the correction information acquiring terminal 17 of the health management system 1 may be configured to change the setting against network connection interruption in response to receiving an alert from an information source such as an earthquake warning system indicating that the bio-information acquiring terminals 11a, 11b, 11c, the information display terminal 15, the information input terminal 16, and the correction information acquiring terminal 17 of the health management system 1 may be cut off from the network on the outside of the house. This makes it easy to continuously utilize the health management system 1, even in the case where the bio-information acquiring terminals 11a, 11b, 11c, the information display terminal 15, the information input terminal 16, and the correction information acquiring terminal 17 of the health management system 1 may be cut off from the network on the outside of the house.

Further, each of the bio-information acquiring terminals 11a, 11b, 11c, the information display terminal 15, the information input terminal 16, and the correction information acquiring terminal 17 of the health management system 1 may be desirably provided with an electric power supply source so that each of the bio-information acquiring terminals 11a, 11b, 11c, the information display terminal 15, the information input terminal 16, and the correction information acquiring terminal 17 is usable, even in the case where electric power supply from the outside of the house is cut off. This makes it possible to continuously utilize the health management system 1, even in the case where electric power supply from the outside of the house is cut off.

As described above, in the case where health management is performed with use of a plurality of bio-information acquiring terminals connected via the network 13, it is desirable to standardize and unify personal authentication units provided in the respective bio-information acquiring terminals. This allows for the processing server 14 to easily record bio-information acquired from a toilet device installed in a place where the user has visited for the first time, or from a blood pressure meter the user has used for the first time.

Further, the personal authentication unit may be a non-contact personal authentication unit configured to perform personal authentication such as iris authentication, retinal authentication, or face authentication. This makes it possible to perform personal authentication without annoying users, even in the case where a plurality of users utilize the bio-information acquiring terminal. In particular, the personal authentication unit may be desirably configured to perform personal authentication by iris authentication, because iris authentication makes it possible to accurately authenticate the users.

Further, the bio-information acquiring terminals 11a, 11b, 11c, the information display terminal 15, the information input terminal 16, and the correction information acquiring terminal 17 of the health management system 1 are configured to acquire personal authentication information as described above, and to transmit the acquired personal authentication information to the processing server 14. For instance, in the case where personal authentication is performed by fingerprint authentication, the bio-information acquiring terminals 11a, 11 b, 11c, the information display terminal 15, the information input terminal 16, and the correction information acquiring terminal 17 may transmit, to the processing server 14, a fingerprint image, or a fingerprint image obtained by encryption or compression based on a certain rule. The processing server 14 is configured to specify the user from the received fingerprint image, whereby it is possible to omit processing of registering fingerprint images of all the users in the bio-information acquiring terminals 11a, 11b, 11c, the information display terminal 15, the information input terminal 16, and the correction information acquiring terminal 17, and to omit the user's cumbersome operation of carrying an ID card storing a template for personal authentication (information in which the user and the fingerprint image are correlated to each other).

Further, the information display terminal 15 may be configured to perform processing of specifying the user from the aforementioned fingerprint image. This eliminates the need of storing a database of fingerprint information with respect to each of the users. Accordingly, the above configuration is advantageous in accurately and easily protecting personal information. In view of the above, the information display terminal 15 may be configured to store a database, in which information relating to the user, and personal authentication information for reference are correlated to each other.

Further, in the specification, the health management system 1 is configured to grasp the health condition of the user, to maintain the health of the user, and to perform health management, early detection of a disease, or prognostic management of a disease. The health management system 1 may be configured to carry out a business (service) of providing obtained bio-information and personal authentication information to a third party. In carrying out the business, the health management system 1 may be desirably configured to provide bio-information in a state that personal authentication information is omitted. This is advantageous in securely protecting personal information of the user.

For instance, as described above, the processing server 14 is capable of predicting an epidemic of influenza, based on a change in internal body temperature of users with respect to each area acquired from the bath devices.

Further, the processing server 14 may be configured to collect supplementary information such as the contents of meals of each of the users, together with bio-information of each of the users, and to provide a research institution with the collected supplementary information and bio-information. This makes it possible to collect information which may lead to elucidation of a relationship between meals and health.

Further, the processing server 14 may be configured to collect information relating to medicines administered to each of the users, together with bio-information of each of the users, and to provide pharmaceutical manufacturers with the collected information relating to medicines and bio-information. This makes it easy to elucidate the effects and side-effects of medicines.

Further, the processing server 14 may be configured to collect information relating to health-care equipment used by each of the users, together with bio-information of each of the users, and to provide health-care equipment manufacturers with the collected information relating to health-care equipment and bio-information. This makes it possible to easily demonstrate the health improvement effects of the health-care equipment.

It is desirable to input the information relating to medicines administered to the user or the information relating to health-care equipment used by the user, with use of the information input terminal 16. This makes it easy to collect information useful for improvement of many kinds of medicines or health-care equipment at an early stage.

Further, the user may register in advance information relating to the sex, the age, the health diagnosis result, the DNA information, and the blood relationship in companies to which the bio-information and personal authentication information of the user is provided. This is advantageous in enhancing the value of bio-information to be sold to a third party.

Further, the processing server 14 may be configured to provide information relating to the office hours, the locations, and the discounted services of exercise facilities which may be effective in improving the health of the user, based on bio-information (health condition) of the user obtained with use of the health management system 1 according to the embodiment. This is advantageous in improving the health condition of the user.

Further, in the case where the bio-information acquiring terminal 11*a* is an oral cavity inspection terminal, the processing server 14 may be configured to provide information relating to the names, the office hours, and the locations of dental clinics near the user's house. This is advantageous in improving the health condition of the user.

Further, in the case where the bio-information acquiring terminal 11*a* is a toilet device (waste component measuring terminal), it is needless to say that the toilet device is desirably installed in a stall. Further, the toilet device may be provided with a user number detecting unit configured to detect the number of users in a stall, in which the toilet device is installed. This makes it possible to prevent a possibility that bio-information of a user other than the authenticated users is erroneously collected.

Further, the bio-information acquiring terminal used by a plurality of users may be provided with a bio-information erasing unit configured to erase the bio-information after use. This makes it possible to prevent a possibility that the bio-information of the user is leaked to the other users.

Further, "more appropriate health management" in the specification means a state such that the progress of the condition of a disease can be more accurately grasped. This makes it possible to perform early detection and prognostic management of the condition of a disease.

The health management system according to the embodiment has been described as above. The configuration described in the specification is merely an example, and it is needless to say that various modifications are applicable as far as such modifications do not depart from the gist of the invention.

The technology described in the foregoing aspects can be implemented in the following types of cloud services. However, the types of cloud services in which the technology described in the foregoing aspects can be implemented are not limited to the above.

(Service Type 1: A Cloud Service Provided by a Datacenter of the Applicant's Company)

Figure 20:
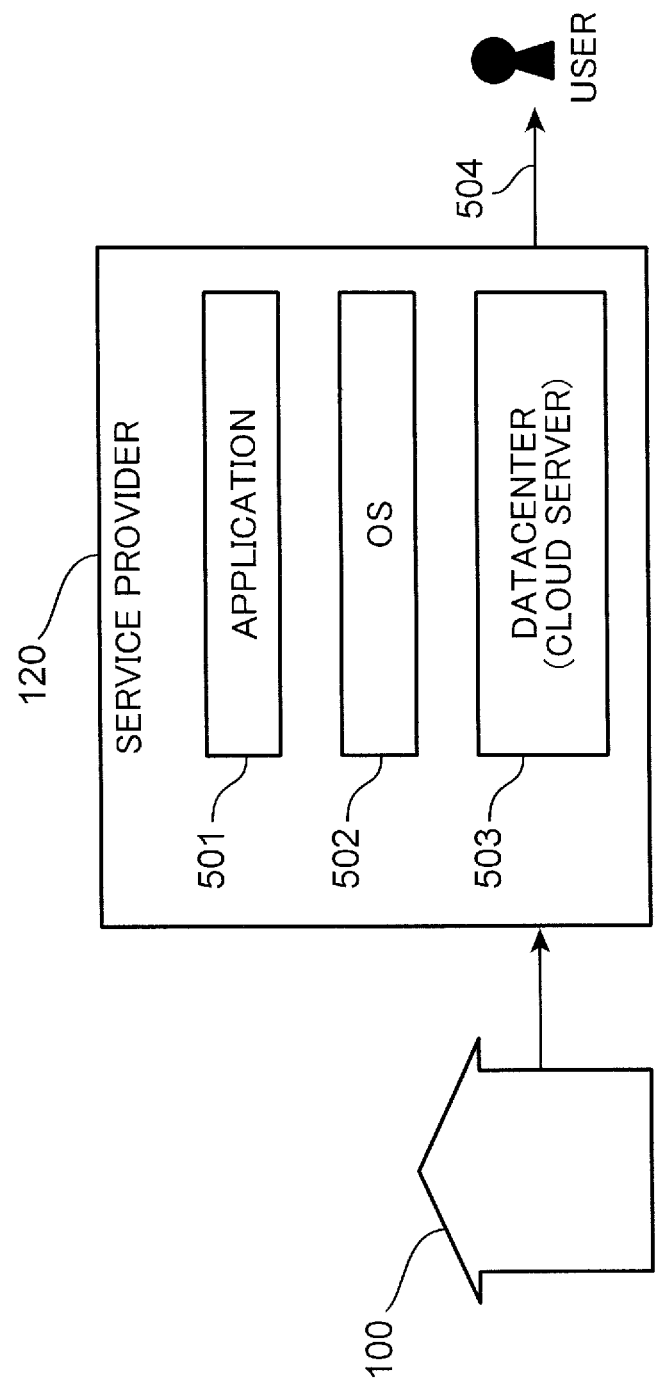
FIG. 20 is a diagram illustrating an overview of services to be provided by an information managing system of service type 1 (a cloud service provided by a datacenter of the applicant's company)

FIG. 20 is a diagram illustrating an overview of services to be provided by an information managing system of service type 1 (a cloud service provided by a datacenter of the applicant's company). In this type, a service provider 120 is configured to acquire information from a group 100, and to provide services to the user. In this type, the service provider 120 has a function of a datacenter operating company. Specifically, the service provider 120 owns a cloud server 111 which manages big data. Therefore, actually, a datacenter operating company does not exist.

In this type, the service provider 120 is configured to operate and manage a datacenter (cloud server) 503. Further, the service provider 120 is configured to manage an operating system (OS) 502 and an application 501. The service provider 120 is configured to provide services with use of the OS 502 and the application 501 to be managed by the service provider 120 (see the arrow 504)

(Service Type 2: A Cloud Service Utilizing IaaS)

Figure 21:
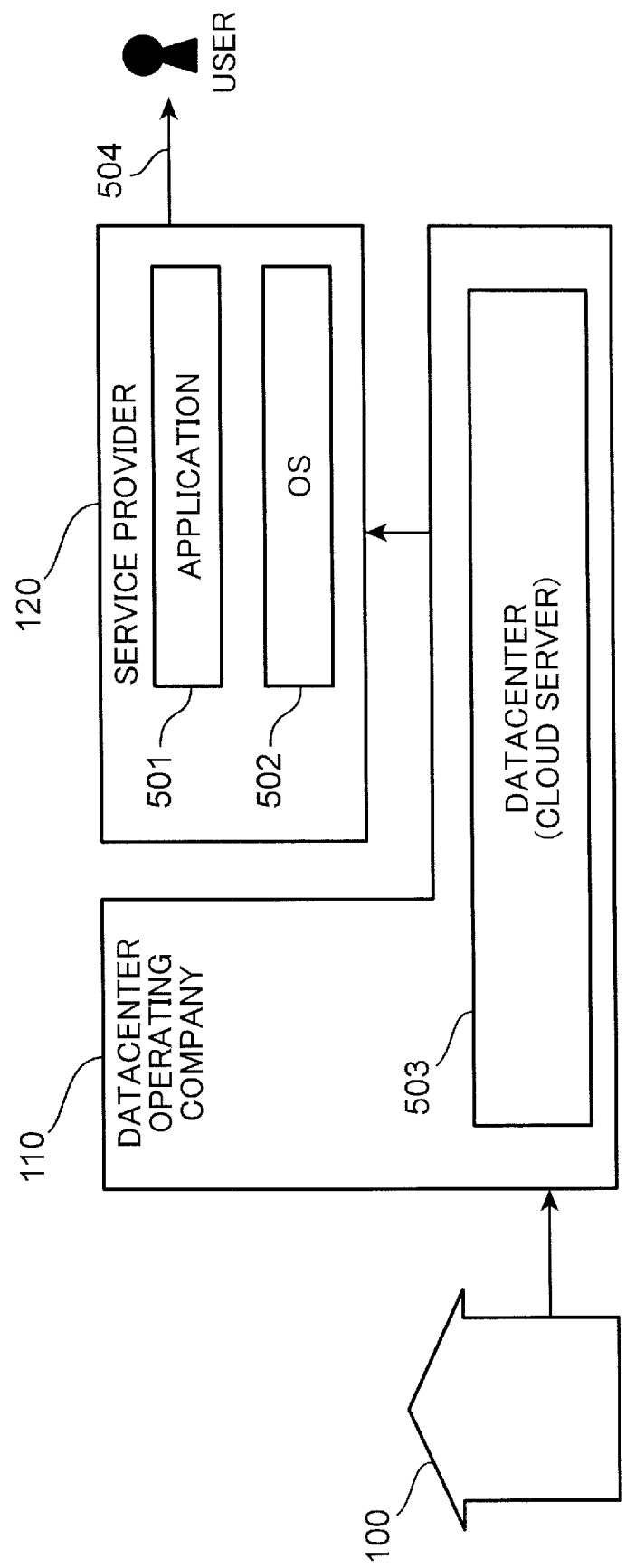
FIG. 21 is a diagram illustrating an overview of services to be provided by an information managing system of service type 2 (a cloud service utilizing IaaS)

FIG. 21 is a diagram illustrating an overview of services to be provided by an information managing system of service type 2 (a cloud service utilizing IaaS). IaaS stands for Infrastructure as a Service. IaaS is a cloud service providing model configured to provide a foundation, based on which a computer system is constructed and operated, as services via the Internet.

In this type, a datacenter operating company 110 is configured to operate and manage a datacenter (cloud server) 503. Further, a service provider 120 is configured to manage an OS 502 and an application 501. The service provider 120 is configured to provide services with use of the OS 502 and the application 501 to be managed by the service provider 120 (see the arrow 504).

(Service Type 3: A Cloud Service Utilizing PaaS)

Figure 22:
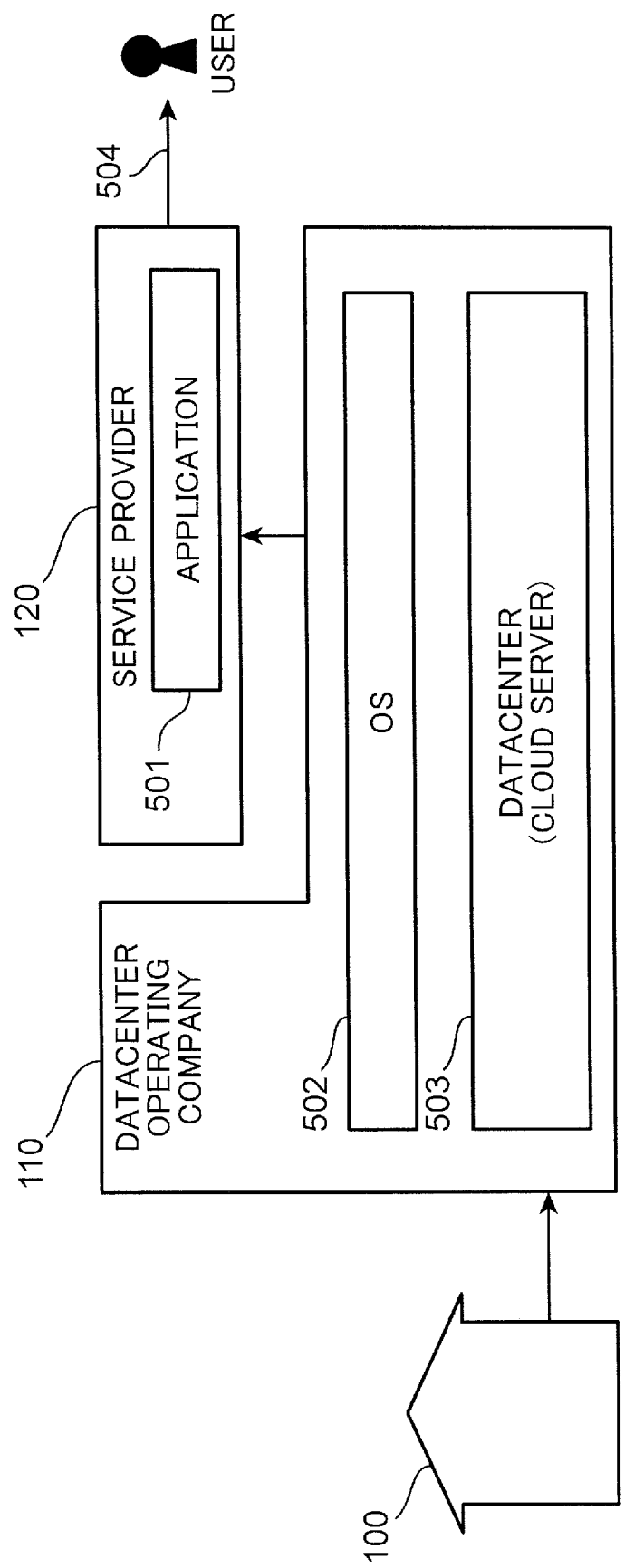
FIG. 22 is a diagram illustrating an overview of services to be provided by an information managing system of service type 3 (a cloud service utilizing PaaS)

FIG. 22 is a diagram illustrating an overview of services to be provided by an information managing system of service type 3 (a cloud service utilizing PaaS). PaaS stands for Platform as a Service. PaaS is a cloud service providing model configured to provide a platform, based on which a software is constructed and operated, as services via the Internet.

In this type, a datacenter operating company 110 is configured to manage an OS 502, and to operate and manage a datacenter (cloud server) 503. Further, a service provider 120 is configured to manage an application 501. The service provider 120 is configured to provide services with use of the OS 502 to be managed by the datacenter operating company 110 and the application 501 to be managed by the service provider 120 (see the arrow 504).

(Service Type 4: A Cloud Service Utilizing SaaS)

Figure 23:
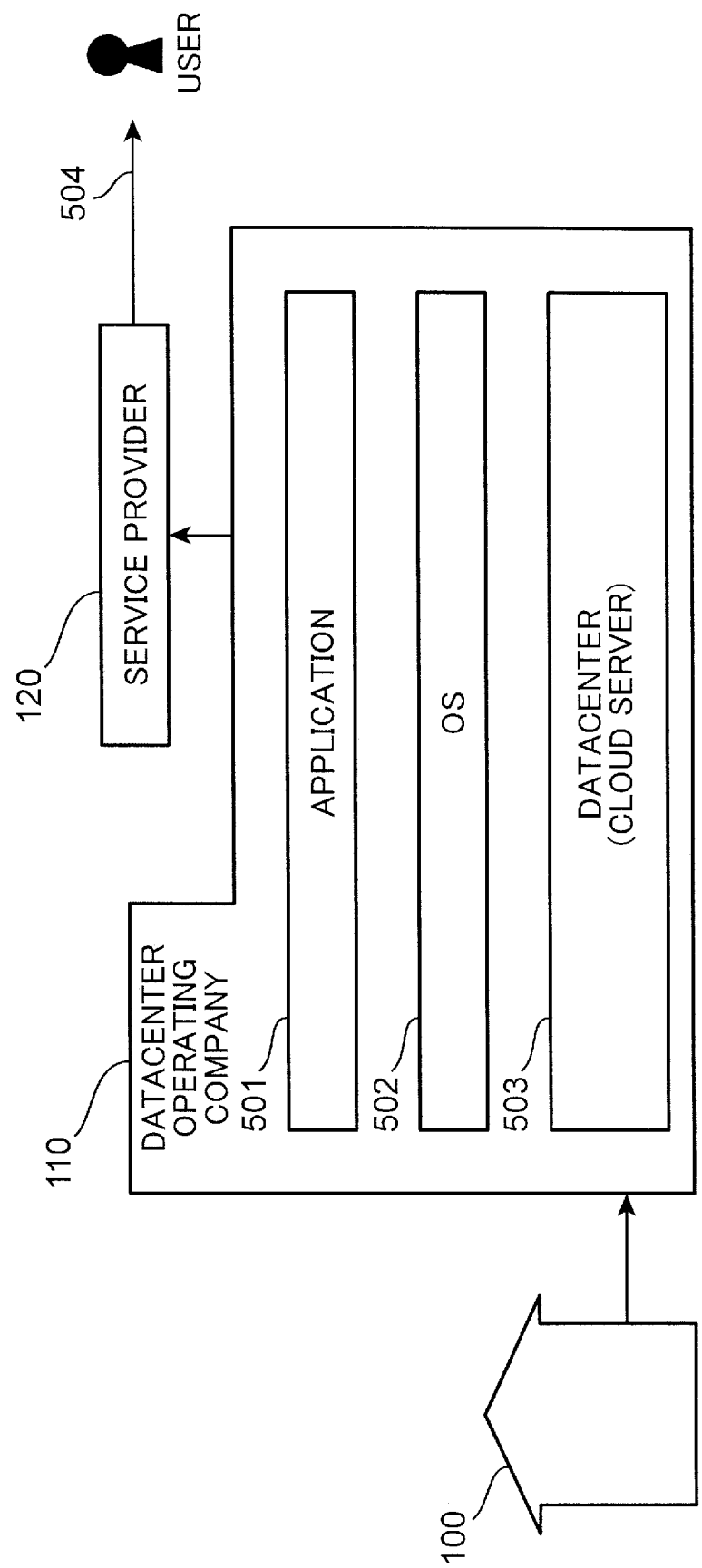
FIG. 23 is a diagram illustrating an overview of services to be provided by an information managing system of service type 4 (a cloud service utilizing SaaS).

FIG. 23 is a diagram illustrating an overview of services to be provided by an information managing system of service type 4 (a cloud service utilizing SaaS). SaaS stands for Software as a Service. A cloud service utilizing SaaS is e.g. a cloud service providing model having a function, with which the user such as a company or a person who does not own a datacenter (a cloud server) is allowed to use an application provided by a platform provider who owns the datacenter (a cloud server) via a network such as the Internet.

In this type, a datacenter operating company 110 is configured to manage an application 501, to manage an OS 502, and to operate and mange a datacenter (a cloud server) 503. Further, a service provider 120 is configured to provide services, with use of the OS 502 and the application 501 to be managed by the datacenter operating company 110 (see the arrow 504).

As described above, in any of the cloud service types, the service provider 120 is configured to provide services. Further, for instance, a service provider or a datacenter operating company may develop an application or a database for big data by themselves, or may outsource the development to a third party.

The foregoing embodiments mainly include the invention having the following configurations.

A bio-information acquiring terminal according to an aspect of the invention is a bio-information acquiring terminal for acquiring bio-information. The bio-information acquiring terminal includes a bath device. The bio-information acquiring terminal is provided with a bio-information measuring unit configured to measure bio-information of a user taking a bath, and a user specifying unit configured to specify the user.

According to the above configuration, the bio-information acquiring terminal includes a bath device. Bio-information of the user taking a bath is measured by the bio-information measuring unit, and the user is specified by the user specifying unit.

As described above, bio-information of the user taking a bath is measured. Accordingly, it is possible to easily manage daily changes of the health condition of the user in his or her daily life, using the measured bio-information.

Further, in the bio-information acquiring terminal, preferably, the bio-information measuring unit may include an electrocardiogram measuring unit disposed in a bathtub and configured to measure an electrocardiogram of the user.

According to the above configuration, an electrocardiogram of the user is measured by the electrocardiogram measuring unit disposed in the bathtub. Accordingly, it is possible to perform a screening test for arteriosclerosis of the user, based on the measured electrocardiogram.

Further, in the bio-information acquiring terminal, preferably, the bio-information measuring unit may include a heart sound measuring unit disposed in a bathtub and configured to measure a heart sound of the user.

According to the above configuration, a heart sound of the user is measured by the heart sound measuring unit disposed in the bathtub. Accordingly it is possible to detect a change in heart rate of the user based on the measured heart sound.

Further, in the bio-information acquiring terminal, preferably, the bio-information measuring unit may include a pulse oximeter disposed in a bathtub and configured to measure an oxygen saturation degree in blood of the user or a pulse rate of the user.

According to the above configuration, an oxygen saturation degree in blood of the user or a pulse rate of the user is measured by the pulse oximeter disposed in the bathtub. Accordingly, it is possible to monitor the fatigue of the user, based on the measured oxygen saturation degree in blood of the user.

Further, in the bio-information acquiring terminal, preferably, the bio-information measuring unit may include a component analyzing unit disposed in a bathtub and configured to analyze a component of sweat of the user contained in water in the bathtub.

According to the above configuration, a component of sweat of the user contained in water in the bathtub is analyzed by the component analyzer disposed in the bathtub. Accordingly, it is possible to acquire bio-information of many kinds, whereby it is possible to grasp the conditions of diseases of many kinds.

Further, in the bio-information acquiring terminal, preferably, the bio-information measuring unit may include a skin surface temperature measuring unit configured to measure a skin surface temperature of the user at a time before the user takes a bath and at a time after the user takes a bath.

According to the above configuration, the skin surface temperature of the user at a time before the user takes a bath and at a time after the user takes a bath is measured by the skin surface temperature measuring unit. Accordingly, it is possible to measure the health condition with high precision, taking into consideration of an influence on other bio-information due to a change in body temperature.

Further, in the bio-information acquiring terminal, preferably, the bio-information measuring unit may include a water temperature measuring unit configured to measure a temperature of water in the bathtub at a time before the user takes a bath and at a time after the user takes a bath; and a core body temperature calculating unit configured to calculate a core body temperature of the user, based on a change in temperature of the water in the bathtub measured by the water temperature measuring unit at the time before the user takes a bath and at the time after the user takes a bath, a heat capacity of the user, and the skin surface temperature measured by the skin surface temperature measuring unit at the time before the user takes a bath.

According to the above configuration, a temperature of water in the bathtub at a time before the user takes a bath and at a time after the user takes a bath is measured by the water temperature measuring unit. Further, a core body temperature of the user is calculated by the core body temperature calculating unit, based on a change in temperature of the water in the bathtub measured by the water temperature measuring unit at the time before the user takes a bath and at the time after the user takes a bath, a heat capacity of the user, and the skin surface temperature measured by the skin surface temperature measuring unit at the time before the user takes a bath.

Thus, it is possible to calculate the core body temperature of the user. Accordingly, it is possible to grasp the health condition of the user with high precision.

Further, in the bio-information acquiring terminal, preferably, the bio-information measuring unit may include a body weight measuring unit configured to measure a weight of the user.

According to the above configuration, a weight of the user is measured by the body weight measuring unit. Accordingly, it is possible to measure a variety of health conditions utilizing the measured body volume of the user.

Further, in the bio-information acquiring terminal, preferably, the bio-information measuring unit may include a body volume measuring unit configured to measure a body volume of the user; and a body fat percentage calculating unit configured to calculate a body density of the user based on the body volume of the user measured by the body volume measuring unit and the weight of the user measured by the body weight measuring unit for calculating a body fat percentage from the body density of the user.

According to the above configuration, a body volume of the user is measured by the body volume measuring unit, and a body density of the user is calculated by the body fat percentage calculating unit based on the body volume of the user measured by the body volume measuring unit and the weight of the user measured by the body weight measuring unit for calculating a body fat percentage of the user.

Thus, it is possible to present the user of the body fat percentage of the user, and to store the body fat percentage of the user on the daily basis, whereby it is possible to manage the health condition of the user.

Further, in the bio-information acquiring terminal, preferably, the bio-information measuring unit may include a water level measuring unit configured to measure a change in water level in a bathtub for a predetermined time in a state that the user is in the bathtub; and a respiration rate calculating unit configured to calculate a respiration rate of the user for the predetermined time, based on the change in water level for the predetermined time measured by the water level measuring unit.

According to the above configuration, a change in water level in the bathtub for a predetermined time in a state that the user is in the bathtub is measured by the water level measuring unit, and a respiration rate of the user for the predetermined time is calculated by the respiration rate calculating unit, based on the change in water level in the bathtub for the predetermined period measured by the water level measuring unit.

Thus, it is possible to easily calculate a respiration rate of the user for a predetermined time by measuring a change in water level for the predetermined period.

An information managing method according to another aspect of the invention is an information managing method in an information managing system for managing bio-information collected from a bio-information acquiring terminal via a network. The bio-information acquiring terminal includes a bath device. The method includes collecting the bio-information of the user taking a bath, and user specifying information for specifying the user from the bio-information acquiring terminal via the network; and storing the bio-information and the user specifying information collected from the bio-information acquiring terminal in association with each other.

According to the above configuration, the bio-information acquiring terminal includes a bath device. Bio-information of the user taking a bath, and user specifying information for specifying the user are collected from the bio-information acquiring terminal via a network, and the bio-information and the user specifying information collected from the bio-information acquiring terminal are stored in association with each other.

Thus, it is possible to measure bio-information of the user taking a bath. Accordingly, it is possible to easily manage daily changes of the health condition of the user in his or her daily life, using the measured bio-information.

A bio-information acquiring terminal according to another aspect of the invention is a bio-information acquiring terminal for acquiring bio-information. The bio-information acquiring terminal includes a toilet device. The bio-information acquiring terminal is provided with a bio-information measuring unit configured to measure bio-information of the user from the wastes of the user, and a user specifying unit configured to specify the user.

According to the above configuration, the bio-information acquiring terminal includes a toilet device. Bio-information of the user is measured from the wastes of the user by the bio-information measuring unit, and the user is specified by the user specifying unit.

Thus, bio-information of the user is measured from the wastes of the user. Accordingly, it is possible to easily measure daily changes of the health condition of the user in his or her daily life, using the measured bio-information.

Further, in the bio-information acquiring terminal, preferably, the bio-information measuring unit may include a waste component measuring unit disposed in a drainage pipe for conveying the wastes received in a toilet bowl and configured to measure a component of the wastes.

According to the above configuration, a component of the wastes is measured by the waste component measuring unit disposed in the drainage pipe for conveying the wastes received in the toilet bowl. Accordingly, it is possible to acquire bio-information of many kinds, whereby it is possible to grasp the conditions of diseases of many kinds.

Further, in the bio-information acquiring terminal, preferably, the waste component measuring unit may be configured to measure urinary sugar or urinary protein contained in the wastes.

According to the above configuration, the urinary sugar or the urinary protein contained in the wastes is measured by the waste component measuring unit. Accordingly, it is possible to enhance the precision of a screening test or prognostic management of diabetes, kidney diseases, or the like.

Further, in the bio-information acquiring terminal, preferably, the waste component measuring unit may be configured to measure a blood component contained in the wastes.

According to the above configuration, a blood component contained in the wastes is measured by the waste component measuring unit. Accordingly, it is possible to acquire bio-information of many kinds, whereby it is possible to grasp the conditions of diseases of many kinds.

Further, in the bio-information acquiring terminal, preferably, the bio-information measuring unit may include a waste temperature measuring unit configured to measure a temperature of the wastes.

According to the above configuration, a temperature of the wastes is measured by the waste temperature measuring unit. Accordingly, it is possible to estimate the rectal temperature of the user from the temperature of the wastes, whereby it is possible to use the estimated rectal temperature of the user for health management.

Further, in the bio-information acquiring terminal, preferably, the bio-information measuring unit may include a blood pressure measuring unit disposed on a toilet seat on which the user is seated, and configured to measure a blood pressure of the user.

According to the above configuration, a blood pressure of the user is measured by the blood pressure measuring unit disposed on the toilet seat on which the user is seated. This makes it possible to easily measure the blood pressure, and makes it easy to manage daily changes of the health condition of the user in his or her daily life, using the information relating to the measured blood pressure.

Further, in the bio-information acquiring terminal, preferably, the bio-information measuring unit may include a body weight measuring unit disposed on a toilet seat on which the user is seated and configured to measure a weight of the user.

According to the above configuration, a weight of the user is measured by the body weight measuring unit disposed on the toilet seat on which the user is seated. Accordingly, this makes it possible to easily measure the body weight, and makes it possible to easily manage daily changes of the health condition of the user in his or her daily life, using the information relating to the measured weight.

An information managing method according to another aspect of the invention is an information managing method in an information managing system for managing bio-information collected from a bio-information acquiring terminal via a network. The bio-information acquiring terminal includes a toilet device. The method includes collecting the bio-information of the user to be obtained from the wastes of the user, and user specifying information for specifying the user from the bio-information acquiring terminal via the network; and storing the bio-information and the user specifying information collected from the bio-information acquiring terminal in association with each other.

According to the above configuration, the bio-information acquiring terminal includes a toilet device. Bio-information of the user to be obtained from the wastes of the user, and user specifying information for specifying the user are collected from the bio-information acquiring terminal via the network, and the bio-information and the user specifying information collected from the bio-information acquiring terminal are stored in association with each other.

Thus, bio-information of the user is measured from the wastes of the user. Accordingly, it is possible to easily manage daily changes of the health condition of the user in his or her daily life, using the measured bio-information.

A bio-information acquiring terminal according to another aspect of the invention is a bio-information acquiring terminal for acquiring bio-information. The bio-information acquiring terminal is provided with a bio-information measuring unit configured to measure bio-information of the user in the oral cavity of the user, and a user specifying unit configured to specify the user.

According to the above configuration, the bio-information acquiring terminal includes a toilet device. Bio-information of the user in the oral cavity of the user is measured by the bio-information measuring unit, and the user is specified by the user specifying unit.

Thus, bio-information of the user in the oral cavity of the user is measured. Accordingly, it is possible to easily mange daily changes of the health condition of the user in his or her daily life, using the measured bio-information.

Further, in the bio-information acquiring terminal, preferably, the bio-information measuring unit may include a body fluid component measuring unit to be inserted in the oral cavity of the user and configured to measure a component of body fluid in the oral cavity.

According to the above configuration, a component of body fluid in the oral cavity is measured by the body fluid component measuring unit to be inserted in the oral cavity of the user. Accordingly, it is possible to acquire bio-information of many kinds, whereby it is possible to grasp the conditions of diseases of many kinds.

Further, in the bio-information acquiring terminal, preferably, the body fluid component measuring unit may be configured to measure a component of saliva in the oral cavity or gingival fluid from the gingival sulcus.

According to the above configuration, a component of saliva in the oral cavity or gingival fluid from the gingival sulcus is measured by the body fluid component measuring unit. This makes it possible to manage the health condition of the user with enhanced precision.

Further, the bio-information acquiring terminal may be preferably formed with a protrusion configured to cause bleeding in the oral cavity, and the body fluid component measuring unit may be configured to measure a component of blood obtained by the protrusion.

According to the above configuration, the oral cavity is caused to bleed by the protrusion, and a component of blood obtained by the protrusion is measured by the body fluid component measuring unit. Accordingly, it is possible to acquire bio-information of many kinds, whereby it is possible to grasp the conditions of diseases of many kinds.

Further, the bio-information acquiring terminal may be preferably provided with a grip part to be held by the user, and the bio-information measuring unit may include a body temperature measuring unit disposed at such a position that the user's finger touches the grip part and configured to measure a temperature of the user's finger.

According to the above configuration, a temperature of the user's finger is measured by the body temperature measuring unit disposed at such a position that the user's finger touches the grip part to be held by the user. This makes it possible to easily measure the body temperature of the user.

Further, in the bio-information acquiring terminal, preferably, the bio-information measuring unit may include an oral cavity temperature measuring unit configured to measure a temperature of the oral cavity.

According to the above configuration, a temperature of the oral cavity is measured by the oral cavity temperature measuring unit. This makes it possible to accurately measure the body temperature of the user.

Further, the bio-information acquiring terminal may be preferably provided with a plurality of protrusions configured to clean the oral cavity.

According to the above configuration, the oral cavity is cleaned by the protrusions. Accordingly, it is possible to easily acquire bio-information, while cleaning the oral cavity.

An information managing method according to another aspect of the invention is an information managing method in an information managing system for managing bio-information collected from a bio-information acquiring terminal via a network. The method includes collecting bio-information of the user in the oral cavity of the user, and user specifying information for specifying the user from the bio-information acquiring terminal via the network; and storing the bio-information and the user specifying information collected from the bio-information acquiring terminal in association with each other.

According to the above configuration, bio-information of the user in the oral cavity of the user, and user specifying information for specifying the user are collected from the bio-information acquiring terminal via the network, and the bio-information and the user specifying information collected from the bio-information acquiring terminal are stored in association with each other.

Thus, bio-information of the user in the oral cavity of the user is measured. Accordingly, it is possible to easily manage daily changes of the health condition of the user in his or her daily life, using the measured bio-information.

The embodiments or the examples described in the section of description of embodiments are provided to clarify the technical contents of the invention. The invention should not be construed to be limited to the embodiments or the examples. The invention may be modified in various ways as far as such modifications do not depart from the spirit and the scope of the invention hereinafter defined.

INDUSTRIAL APPLICABILITY

A bio-information acquiring terminal and an information managing method of the invention are capable of easily managing daily changes of the health condition of the user in his or her daily life, using measured bio-information, and is capable of performing early detection of a cancer or a lifestyle disease or is applicable to prognostic management; and accordingly, are useful as a bio-information acquiring terminal for acquiring bio-information and an information managing method using the bio-information acquiring terminal. Further, it is possible to provide health management with high precision and with less constraints in a daily life.

The invention claimed is:

1. An information displaying method for displaying, on a display device, information to be generated based on bio-information collected in a service providing system configured such that a service provider collects the bio-information from a plurality of bio-information acquiring terminals via a network and provides a service based on the collected bio-information, the method comprising:
    displaying one or more of the bio-information acquiring terminals owned by a user using the display device;
    displaying each of the bio-information collected by the bio-information acquiring terminals in association with each of the bio-information acquiring terminals;
    displaying each of the bio-information by differentiating a first display mode for bio-information permissible to be provided to the service provider from a second display mode for bio-information impermissible to be provided to the service provider; and
    displaying each of the bio-information by differentiating a third display mode for bio-information permissible to be stored in the bio-information acquiring terminal from a fourth display mode for bio-information impermissible to be stored in the bio-information acquiring terminal.

2. A service providing system configured such that a service provider collects bio-information from a plurality of bio-information acquiring terminals via a network and provides a service based on the collected bio-information, the system comprising:
    displaying, on a display device for displaying information to be generated based on the collected bio-information, one or more of the bio-information acquiring terminals owned by a user using the display device;
    displaying each of the bio-information collected by the bio-information acquiring terminals in association with each of the bio-information acquiring terminals;
    displaying, on the display device, each of the bio-information by differentiating a first display mode for bio-information permissible to be provided to the service provider from a second display mode for bio-information impermissible to be provided to the service provider; and
    displaying, on the display device, each of the bio-information by differentiating a third display mode for bio-information permissible to be stored in the bio-information acquiring terminal from a fourth display mode for bio-information impermissible to be stored in the bio-information acquiring terminal.

3. A non-transitory computer readable recording medium which stores therein a program causing a computer to serve as a display device for displaying information to be generated based on bio-information collected from a plurality of bio-information acquiring terminals via a network, the program further causing the computer to execute:
    displaying, on a display of the computer, one or more of the bio-information acquiring terminals owned by a user using the display device;
    displaying, on the display, each of the bio-information collected by the bio-information acquiring terminals in association with each of the bio-information acquiring terminals, and
    displaying, on the display, each of the bio-information by differentiating a first display mode for bio-information permissible to be provided to a service provider which provides a service based on the bio-information from a second display mode for bio-information impermissible to be provided to the service provider; and
    displaying, on the display, each of the bio-information by differentiating a third display mode for bio-information permissible to be stored in the bio-information acquiring terminal from a fourth display mode for bio-information impermissible to be stored in the bio-information acquiring terminal.

4. The information display method according to claim 1, wherein the first display mode displays the bio-information permissible to be provided to the service provider in a first color, and the second display mode displays the bio-information impermissible to be provided to the service provider in a second color different from the first color.

* * * * *